US008999974B2

(12) United States Patent
Morita et al.

(10) Patent No.: US 8,999,974 B2
(45) Date of Patent: Apr. 7, 2015

(54) ACYL PIPERAZINE DERIVATIVES AS TTX-S BLOCKERS

(75) Inventors: Mikiko Morita, Aichi (JP); Shuzo Watanabe, Aichi (JP)

(73) Assignee: Raqualia Pharma Inc., Aichi (JP)

( * ) Notice: Subject to any disclaimer, the term of this patent is extended or adjusted under 35 U.S.C. 154(b) by 0 days.

(21) Appl. No.: 13/814,716

(22) PCT Filed: Aug. 9, 2011

(86) PCT No.: PCT/JP2011/004515
§ 371 (c)(1),
(2), (4) Date: Feb. 26, 2013

(87) PCT Pub. No.: WO2012/020567
PCT Pub. Date: Feb. 16, 2012

(65) Prior Publication Data
US 2013/0150356 A1    Jun. 13, 2013

Related U.S. Application Data

(60) Provisional application No. 61/371,822, filed on Aug. 9, 2010.

(51) Int. Cl.
| C07D 403/12 | (2006.01) |
| A61K 31/506 | (2006.01) |
| C07D 239/47 | (2006.01) |
| A61K 45/06 | (2006.01) |
| C07D 401/14 | (2006.01) |
| C07D 405/12 | (2006.01) |
| C07D 409/12 | (2006.01) |
| C07D 413/12 | (2006.01) |
| C07D 417/12 | (2006.01) |
| A61K 31/517 | (2006.01) |
| A61K 31/538 | (2006.01) |
| C07D 401/12 | (2006.01) |
| C07D 403/04 | (2006.01) |
| C07D 417/14 | (2006.01) |
| C07D 471/04 | (2006.01) |
| C07D 487/08 | (2006.01) |
| C07D 495/04 | (2006.01) |

(52) U.S. Cl.
CPC ............ *C07D 239/47* (2013.01); *A61K 31/506* (2013.01); *A61K 45/06* (2013.01); *C07D 401/14* (2013.01); *C07D 403/12* (2013.01); *C07D 405/12* (2013.01); *C07D 409/12* (2013.01); *C07D 413/12* (2013.01); *C07D 417/12* (2013.01); *A61K 31/517* (2013.01); *A61K 31/538* (2013.01); *C07D 401/12* (2013.01); *C07D 403/04* (2013.01); *C07D 417/14* (2013.01); *C07D 471/04* (2013.01); *C07D 487/08* (2013.01); *C07D 495/04* (2013.01)

(58) Field of Classification Search
USPC ................ 544/295; 514/252.14, 252.19, 218; 540/575
See application file for complete search history.

(56) References Cited

U.S. PATENT DOCUMENTS

2007/0093454 A1    4/2007    Wilson et al.

FOREIGN PATENT DOCUMENTS

| EP | 1645556 A1 | 4/2006 |
| JP | 2008540443 A | 11/2008 |
| WO | WO-2008147864 A2 | 12/2008 |

OTHER PUBLICATIONS

Bundgaard, Design of Prodrugs: Introduction, p. 1, 1985.*
Damasio, Alzheimer's Disease and Related Dementias, Cecil Textbook of Medicine, 20th Edition, vol. 2, pp. 1992-1996 (1996).*
Layzer, Degenerative Diseases of the Nervous System, Cecil Textbook of Medicine, 20th Edition, vol. 2, pp. 2050-2057 (1996).*
Silverman, Prodrugs and Drug Delivery Systems, The Organic Chemistry of Drug Design and Drug Action, pp. 352-400, 1992.*
Kayano et al., "Primary structure of rat brain sodium channel III deduced from the cDNA sequence," *FEBS Letters* 228: 187-194, 1988.
Lu et al., "Isolation of a Human-Brain Sodium-Channel Gene Encoding Two Isoforms of the Subtype III α-Subunit," *Journal of Molecular Neuroscience* 10: 67-70,1998.
Chen et al., "Cloning, distribution and functional analysis of the type III sodium channel from human brain," *European Journal of Neuroscience* 12: 4281-4289, 2000.
Black et al., "Upregulation of a Silent Sodium Channel After Peripheral, but not Central, Nerve Injury in DRG Neurons," *Journal of Neurophysiology* 82: 2776-2785, 1999.
Craner et al., "Changes of Sodium Channel Expression in Experimental Painful Diabetic Neuropathy," *Annals of Neurology* 52: 786-792, 2002.
Dib-Hajj et al., "Plasticity of sodium channel expression in DRG neurons in the chronic constriction injury model of neuropathic pain," *PAIN* 83: 591-600, 1999.
Hong et al., "Early Painful Diabetic Neuropathy Is Associated with Differential Changes in Tetrodotoxin-sensitive and -resistant Sodium Channels in Dorsal Root Ganglion Neurons in the Rat," *The Journal of Biological Chemistry* 279: 29341-29350, 2004.
Kim et al., "The changes in expression of three subtypes of TTX sensitive sodium channels in sensory neurons after spinal nerve litigation," *Molecular Brain Research* 95:153-161, 2001.
Hains et al., "Altered Sodium Channel Expression in Second-Order Spinal Sensory Neurons Contributes to Pain after Peripheral Nerve Injury," *The Journal of Neuroscience* 24: 4832-4839, 2004.

(Continued)

*Primary Examiner* — Deepak Rao
(74) *Attorney, Agent, or Firm* — Marshall, Gerstein & Borun LLP

(57) ABSTRACT

The present invention relates to acyl piperazine derivatives which have blocking activities of voltage gated sodium channels as the TTX-S channels, and which are useful in the treatment or prevention of disorders and diseases in which voltage gated sodium channels are involved. The invention also relates to pharmaceutical compositions comprising these compounds and the use of these compounds and compositions in the prevention or treatment of such diseases in which voltage gated sodium channels are involved.

8 Claims, No Drawings

(56) References Cited

OTHER PUBLICATIONS

Cox et al., "An SCN9A channelopathy causes congenital inability to experience pain," *Nature* 444: 894-898, 2006.

Baker et al., "Involvement of Na+ channels in pain pathways," *TRENDS in Pharmacological Sciences* 22: 27-31, 2001.

Lyu et al., "Low dose of tetrodotoxin reduces neuropathic pain behaviors in an animal model," *Brain Research* 871: 98-103, 2000.

International Search Report in corresponding PCT/JP2011/004515 dated Aug. 26, 2011.

Database Chemcats on STN: AN 0062607277 published Jan. 30, 2012.

* cited by examiner

ACYL PIPERAZINE DERIVATIVES AS TTX-S BLOCKERS

TECHNICAL FIELD

The present invention relates to acyl piperazine derivatives which have blocking activities of voltage gated sodium channels as tetrodotoxin-sensitive (TTX-S) channels, and which are useful in the treatment or prevention of disorders and diseases in which voltage gated sodium channels are involved. The invention also relates to pharmaceutical compositions comprising these compounds and the use of these compounds and compositions in the prevention or treatment of such diseases in which voltage gated sodium channels are involved.

BACKGROUND ART

The rat $Na_{V1.3}$ channel and the human $Na_{V1.3}$ channel have been cloned in 1988 and 1998/2000 respectively (NPL 1; NPL 2; NPL 3). The $Na_{V1.3}$ channel was formerly known as brain type III sodium channel. $Na_{V1.3}$ is present at relatively high levels in the nervous system of rat embryos but is barely detectable in adult rats. $Na_{V1.3}$ is up-regulated following axotomy in the Spinal Nerve Ligation (SNL), Chronic Constriction Injury (CCI), and diabetic neuropathy models (NPL 4; NPL 5; NPL 6; NPL 7; NPL 8) The up-regulation of $Na_{V1.3}$ channel contributes to rapidly repriming sodium current in small dorsal root ganglion (DRG) neurons (NPL 4). These observations suggest that $Na_{V1.3}$ may make a key contribution to neuronal hyperexcitability.

In order to validate the contribution of $Na_{V1.3}$ sodium channel in the pain states, specific antisense oligonucleotides (ASO) were used in animal pain models. $Na_{V1.3}$ sodium channel ASO treatment significantly attenuated pain-related behaviors after CCI operation (NPL 9). These findings suggest that $Na_{V1.3}$ sodium channel antagonist is useful to treat neuropathic pain conditions.

The $Na_{v1.7}$ channel appears to be the best 'validated' pain target. The most exciting findings with respect to $Na_{v1.7}$ have come from human genetic studies. Cox et al. (NPL 10) discovered SCN9A mutations that cause a loss of $Na_{v1.7}$ function in three families from Pakistan. Their observations link loss of $Na_{v1.7}$ function with a congenital inability to experience pain, adding to the evidence indicating $Na_{v1.7}$ channel as an essential participant in human nociception.

By contrast, Gain-of-function mutations have also been described that lead to enhanced pain, for example, Primary Erythermalgia in one case and Paroxysmal Extreme Pain Disorder in another. These gain-of-function mutations in patients led to different types of gating changes in $Na_{v1.7}$ sodium currents and, interestingly, different degrees of effectiveness of specific sodium channel blocking drugs. The implication from these findings is that a selective $Na_{v1.7}$ blocker may be an effective treatment for pain in man.

A local anaesthetic lidocaine and a volatile anaesthetic halothane are known to act on both tetrodotoxin-resistant (TTX-R) and TTX-S sodium channels with poor selectivity and low potency ($IC_{50}$ values range from 50 microM to 10 mM). These anaesthetics at high systemic concentrations could cause devastating side effects, e.g., paralysis and cardiac arrest. However, systemic administration of lidocaine at low concentrations is effective to treat chronic pain (NPL 11). In rats, application of a very low dose of TTX to the DRG of the injured segment of the L5 spinal nerve significantly reduces mechanical allodynic behavior (NPL 12). This suggests that TTX-S subtypes of sodium channels play an important role in maintaining allodynic behaviors in an animal model of neuropathic pain.

The $Na_{V1.5}$ channel is also a member of TTX-resistant sodium channels. The $Na_{V1.5}$ channel is almost exclusively expressed in cardiac tissue and has been shown to underlie a variety of cardiac arrhythmias and conduction disorders.

CITATION LIST

Non Patent Literature

NPL 1: FEBS Lett. 228 (1), 187-194, 1988
NPL 2: J. Mol. Neurosci., 10 (1), 67-70, 1998
NPL 3: Eur. J. Neurosci. 12 (12), 4281-4289, 2000
NPL 4: J Neurophysiol 82, 2776-2785, 1999. J. A. Black et al.
NPL 5: Ann Neurol 52, 786-792, 2002. M. J. Cranner et al.
NPL 6: Pain 83, 591-600, 1999. S. Dib-Hajj et al.
NPL 7: J Biol Chem 279, 29341-29350, 2004. S. Hong et al.
NPL 8: Mol Brain Res 95, 153-161, 2001. C. H. Kim et al.
NPL 9: J. Neurosci. 24, 4832-4839, 2004, Haim, B. C. et al.
NPL 10: Nature 444, 894-898, 2006
NPL 11: Trends in Pharm. Sci 22, 27-31, 2001, Baker, M. D. et al.
NPL 12: Brain Res 871, 98-103, 2000, Lyu, Y. S. et al.

SUMMARY OF INVENTION

Technical Problem

It is an objective of the invention to provide new TTX-S blockers that are good drug candidates. Preferred compounds should bind potently to the TTX-S ($Na_{V1.3}$ and $Na_{V1.7}$) channels whilst showing little affinity for other sodium channels, particularly the $Na_{V1.5}$ channel. They should be well absorbed from the gastrointestinal tract, be metabolically stable and possess favorable pharmacokinetic properties. They should be non-toxic and demonstrate few side-effects. Furthermore, the ideal drug candidate will exist in a physical form that is stable, non-hygroscopic and easily formulated.

Solution to Problem

The compounds of this invention characterized by pyrimidine ring with alkoxy, cycloalkoxy, alkylthio, or cycloalkylthio group and heterocyclylamide group including two nitrogens in the heterocyclyl ring are novel, and are quite different from the prior arts. In addition the compounds of this invention with a heterocyclylamide group greatly contribute improving the selectivity for the $Na_{V1.3}$ or $Na_{V1.7}$ channel as compared with $Na_{V1.5}$ channel.

Structurally close compounds are disclosed in WO 9728128, WO 2010020432, EP 1645 556, and WO 2006034446, which are not for sodium channel blockers of this invention but for quite different biological targets.

For example, although EP 1645 556 discloses arylpiperazine-benzoylamide derivatives, it has tubulin polymerisation inhibitory activity, which never discloses sodium channel blocking activities. The imidazole moiety of the invention is formally included in the said broad formula in claim, but neither actual working examples nor embodiments in the specification.

WO 2008147864 discloses pyrimidin-2-ylpiperazine compounds with no substituent on the pyrimidine ring for sodium channel blocking activities, whereas the compounds of the present invention are pyrimidin-4-ylpiperazine with a substituent such as alkoxy, cycloalkoxy, alkylthio, and cycloalkylthio group on the pyrimidine ring, which contributes advantages against sodium channel blocking activities. We confirmed that the representative compound, 3-(2-phenylethyl)-7-[(4-pyrimidin-2-ylpiperazin-1-yl)carbonyl]quinazoline-2,4(1H,3H)-dione, showed no activity against $Na_{V1.7/1.3}$.

Advantageous Effects of Invention

The acyl piperazine derivatives of the present invention are sodium channel blockers and have a number of therapeutic applications, particularly in the treatment of pain.

More particularly, the acyl piperazine derivatives of the invention are selective TTX-S blockers. In the above discussion, the invention is exemplified by reference to the inhibition of $Na_{V1.3}$ or $Na_{V1.7}$ channel as the TTX-S channels. They show the affinity for $Na_{V1.3}$ or $Na_{V1.7}$ channel which is significantly greater than their affinity for $Na_{V1.5}$ channel as TTX-R sodium channels. Acyl piperazine derivatives of the invention show good selectivity for the $Na_{V1.3}$ or $Na_{V1.7}$ channel as compared with $Na_{V1.5}$ channel.

In particular, the acyl piperazine derivatives of the present invention are selective for the TTX-S channels over the $Na_{V1.5}$ channel, leading to improvements in the side-effect profile.

The acyl piperazine derivatives of the present invention are therefore useful in the treatment of a wide range of disorders, particularly pain, acute pain, chronic pain, neuropathic pain, inflammatory pain, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back and orofacial pain.

Other conditions that may be treated with the acyl piperazine derivatives of the present invention include multiple sclerosis, neurodegenerative disorders, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia.

DESCRIPTION OF EMBODIMENTS

The present invention is directed to acyl piperazine derivative compounds which are TTX-S blockers over the $Na_{V1.5}$ channel, and which are useful in the treatment or prevention of neurological and psychiatric disorders and diseases in which TTX-S channels are involved. The invention is also directed to pharmaceutical compositions comprising these compounds and the use of these compounds and compositions in the prevention or treatment of such diseases in which TTX-S sodium channels are involved.

The present invention provides a compound of formula (I) and a salt thereof:

[Chem. 1]

(I)

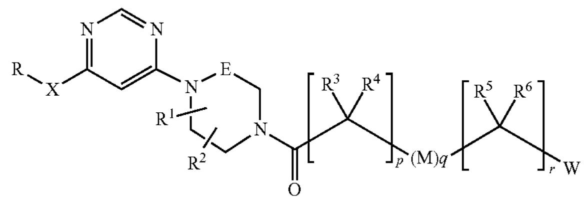

wherein

R is selected from the group consisting of: (1) $C_1$-$C_6$ alkyl and (2) $C_3$-$C_8$ cycloalkyl; which may be optionally substituted with 1 to 3 substituents independently selected from the group consisting of (1) halogen, (2) $C_1$-$C_6$ alkyl, (3) $C_3$-$C_8$ cycloalkyl, (4) hydroxy, (5) $C_1$-$C_6$ alkoxy, (6) amino, (7) $C_1$-$C_6$ alkylamino, (8) di($C_1$-$C_6$ alkyl)amino, (9) hydroxy $C_1$-$C_6$ alkyl, (10) $C_1$-$C_6$ alkoxy $C_1$-$C_6$ alkyl, (11) $C_1$-$C_6$ alkylsulfonyl, (12) aminosulfonyl, (13) $C_1$-$C_6$ alkyl C(═O)—, (14) HO(O═)C—, (15) $C_1$-$C_6$ alkyl-O(O═)C—, (16) $R^AN(R^B)C(═O)$—, (17) $C_1$-$C_6$ alkylsulfonylamino, (18) $R^AC(═O)N(R^B)$—, (19) $NH_2(HN═)C$—, and (20) 5 to 10 membered aryl $C_0$-$C_6$ alkyl; wherein said aryl may be optionally substituted with 1 to 5 substituents independently selected from the group consisting of hydroxy, halogen, $C_1$-$C_6$ alkyl, $C_1$-$C_6$ alkoxy, hydroxy $C_1$-$C_6$ alkyl, amino $C_1$-$C_6$ alkyl, $C_1$-$C_6$ haloalkyl, $C_1$-$C_6$ haloalkoxy, $C_3$-$C_8$ cycloalkyl, amino, $C_1$-$C_6$ alkylamino, di($C_1$-$C_6$ alkyl)amino, $C_1$-$C_6$ alkylthio, and nitro;

Preferably R is selected from the group consisting of: (1) $C_1$-$C_6$ alkyl and (2) $C_3$-$C_8$ cycloalkyl; which may be optionally substituted with 1 to 3 substituents independently selected from the group consisting of (1) halogen, (2) $C_1$-$C_6$ alkyl, (3) $C_3$-$C_8$ cycloalkyl, (4) hydroxy, (5) $C_1$-$C_6$ alkoxy, (6) amino, (7) $C_1$-$C_6$ alkylamino, (8) di($C_1$-$C_6$ alkyl)amino, (9) hydroxy $C_1$-$C_6$ alkyl, (10) $C_1$-$C_6$ alkylsulfonyl, (11) aminosulfonyl, (12) $C_1$-$C_6$ alkyl C(═O)—, (13) $R^AN(R^B)C(═O)$—, (14) $C_1$-$C_6$ alkylsulfonylamino, (15) $C_3$-$C_8$ cycloalkyl, (16) $R^AC(═O)N(R^B)$—, and (17) 5 to 10 membered aryl $C_0$-$C_6$ alkyl; wherein said aryl may be optionally substituted with 1 to 5 substituents independently selected from the group consisting of hydroxy, halogen, $C_1$-$C_6$ alkyl, $C_1$-$C_6$ alkoxy, hydroxy $C_1$-$C_6$ alkyl, amino $C_1$-$C_6$ alkyl, $C_1$-$C_6$ haloalkyl, $C_1$-$C_6$ haloalkoxy, $C_3$-$C_8$ cycloalkyl, amino, $C_1$-$C_6$ alkylamino, di($C_1$-$C_6$ alkyl)amino, $C_1$-$C_6$ alkylthio, and nitro;

More preferably R is selected from the group consisting of: (1) $C_1$-$C_6$ alkyl and (2) $C_3$-$C_8$ cycloalkyl; which may be optionally substituted with 1 to 3 substituents independently selected from the group consisting of (1) halogen, (2) $C_1$-$C_6$ alkyl, (3) $C_3$-$C_8$ cycloalkyl, (4) hydroxy, (5) $C_1$-$C_6$ alkoxy, (6) amino, (7) $C_1$-$C_6$ alkylamino, (8) di($C_1$-$C_6$ alkyl)amino, (9) hydroxy $C_1$-$C_6$ alkyl, and (10) 5 to 10 membered aryl $C_0$-$C_6$ alkyl; wherein said aryl may be optionally substituted with 1 to 5 substituents independently selected from the group consisting of hydroxy, halogen, $C_1$-$C_6$ alkyl, $C_1$-$C_6$ alkoxy, hydroxy $C_1$-$C_6$ alkyl, amino $C_1$-$C_6$ alkyl, $C_1$-$C_6$ haloalkyl, $C_1$-$C_6$ haloalkoxy, $C_3$-$C_8$ cycloalkyl, amino, $C_1$-$C_6$ alkylamino, di($C_1$-$C_6$ alkyl)amino, $C_1$-$C_6$ alkylthio, and nitro;

W is aryl which may be optionally substituted with 1 to 5 substituents independently selected from the group consisting of
(1) halogen, (2) $C_1$-$C_6$ alkyl, (3) $C_3$-$C_8$ cycloalkyl, (4) $C_1$-$C_6$ haloalkyl, (5) hydroxy, (6) $C_1$-$C_6$ alkoxy, (7) $C_1$-$C_6$ haloalkoxy, (8) $C_1$-$C_6$ alkylthio, (9) nitro, (10) amino, (11) $C_1$-$C_6$ alkylamino, (12) di($C_1$-$C_6$ alkyl)amino, (13) cyano, (14) hydroxy $C_1$-$C_6$ alkyl, (15) $C_1$-$C_6$ alkoxy $C_1$-$C_6$ alkyl, (16) $C_1$-$C_6$ alkylsulfonyl, (17) $R^A N(R^B)SO_2$—, (18) $C_1$-$C_6$ alkyl C(=O)—, (19) HO(O=)C—, (20) $C_1$-$C_6$ alkyl-O(O=)C—, (21) $R^A N(R^B)C(=O)$—, (22) $C_1$-$C_6$ alkylsulfonylamino, (23) $C_3$-$C_8$ cycloalkyl, (24) $R^A C(=O)N(R^B)$—, (25) $NH_2(HN=)C$—, and (26) 5 to 10 membered aryl $C_0$-$C_6$ alkyl-$O_{0-1}$—; wherein said aryl may be optionally substituted with 1 to 5 substituents independently selected from the group consisting of hydroxy, halogen, $C_1$-$C_6$ alkyl, $C_1$-$C_6$ alkoxy, hydroxy $C_1$-$C_6$ alkyl, amino $C_1$-$C_6$ alkyl, $C_1$-$C_6$ haloalkyl, $C_1$-$C_6$ haloalkoxy, $C_3$-$C_8$ cycloalkyl $C_0$-$C_6$ alkyl, amino, $C_1$-$C_6$ alkylamino, di($C_1$-$C_6$ alkyl)amino, $C_1$-$C_6$ alkylthio, and nitro;

$R^A$ and $R^B$ are independently selected from the group consisting of:
(1) hydrogen, (2) $C_1$-$C_6$ alkyl, (3) hydroxy $C_1$-$C_6$ alkyl, (4) amino $C_1$-$C_6$ alkyl, (5) $C_1$-$C_6$ haloalkyl, (6) $C_1$-$C_6$ haloalkoxy, (7) $C_3$-$C_6$ alkenyl, (8) $C_3$-$C_8$ cycloalkyl $C_0$-$C_6$ alkyl, and (9) 5 to 10 membered aryl $C_0$-$C_6$ alkyl; wherein said aryl may be optionally substituted with 1 to 5 substituents independently selected from the group consisting of hydroxy, halogen, $C_1$-$C_6$ alkyl, $C_1$-$C_6$ alkoxy, hydroxy $C_1$-$C_6$ alkyl, amino $C_1$-$C_6$ alkyl, $C_1$-$C_6$ haloalkyl, $C_1$-$C_6$ haloalkoxy, $C_3$-$C_8$ cycloalkyl $C_0$-$C_6$ alkyl, amino, $C_1$-$C_6$ alkylamino, di($C_1$-$C_6$ alkyl)amino, $C_1$-$C_6$ alkylthio, and nitro;

$R^1$ and $R^2$ are independently selected from the group consisting of:
(1) hydrogen, (2) hydroxy $C_0$-$C_6$ alkyl, (3) halogen, (4) $C_1$-$C_6$ alkyl, (5) $C_3$-$C_8$ cycloalkyl, and (6) $C_1$-$C_6$ alkoxy;
or $R^1$ and $R^2$ taken together may form a 3 to 8 membered ring, where the ring may contain one to four heteroatom(s) independently selected from nitrogen, oxygen, and sulfur; and the ring may be substituted one or more substituents selected from $R^C$; or $R^1$ and $R^2$ taken together may be an oxo group;

$R^C$ is selected from the group consisting of:
(1) hydrogen, (2) hydroxy $C_0$-$C_6$ alkyl, (3) halogen, (4) $C_1$-$C_6$ alkyl, (5) $C_3$-$C_8$ cycloalkyl, and (6) $C_1$-$C_6$ alkoxy;

$R^3$, $R^4$, $R^5$, and $R^6$ are each independently selected from the group consisting of:
(1) hydrogen, (2) hydroxy, (3) $C_1$-$C_6$ alkyl, (4) $C_3$-$C_8$ cycloalkyl, (5) $C_1$-$C_6$ alkoxy, (6) $R^A N(R^B)$—, (7) $R^A C(=O)N(R^B)$—, and (8) $R^A O$—$C(=O)N(R^B)$—; or $R^3$ and $R^4$ together may be an oxo group; or $R^5$ and $R^6$ together may be an oxo group;

E is —CHR$^1$—, —CHR$^1$CH$_2$—, —CO—CH$_2$—, or —CO—;

p is 0, 1, or 2; when p is one or more than one, $R^3$ and $R^4$ may be same or different;

q is 0, or 1; preferably when p is 0, then q is 0;

r is 0, 1, or 2; when r is one or more than one, $R^5$ and $R^6$ may be same or different;

X is —O—, or —S—; preferably X is —O—;

M is —O—, —NR$^A$—, —S—, —SO—, SO$_2$—, NR$^A$—SO$_2$—, or —SO$_2$—NR$^A$—;

or a prodrug thereof or a pharmaceutically acceptable salt thereof.

The preferable compounds are selected from:
(3-fluoro-4-methylphenyl)(4-(6-isobutoxypyrimidin-4-yl)piperazin-1-yl)methanone;
(4-(6-((1,3-dimethyl-1H-pyrazol-5-yl)methoxy)pyrimidin-4-yl)piperazin-1-yl)(3-fluoro-4-methylphenyl)methanone;
(R)-2-hydroxy-1-(4-(6-isobutoxypyrimidin-4-yl)piperazin-1-yl)-2-phenylethanone;
(S)-2-hydroxy-1-(4-(6-isobutoxypyrimidin-4-yl)piperazin-1-yl)-3-phenylpropan-1-one;
(R)-2-hydroxy-1-(4-(6-isobutoxypyrimidin-4-yl)piperazin-1-yl)-3-phenylpropan-1-one;
(4-(6-(cyclopropylmethoxy)pyrimidin-4-yl)piperazin-1-yl)(3-fluoro-4-methylphenyl)methanone;
(4-(6-(cyclopentyloxy)pyrimidin-4-yl)piperazin-1-yl)(3-fluoro-4-methylphenyl)methanone;
(3-fluoro-4-methylphenyl)(4-(6-(2,2,2-trifluoroethoxy)pyrimidin-4-yl)piperazin-1-yl)methanone;
(1H-indol-4-yl)(4-(6-isobutoxypyrimidin-4-yl)piperazin-1-yl)methanone;
(S)-tert-butyl(2-(4-(6-isobutoxypyrimidin-4-yl)piperazin-1-yl)-2-oxo-1-phenylethyl)carbamate;
(R)-tert-butyl(2-(4-(6-isobutoxypyrimidin-4-yl)piperazin-1-yl)-2-oxo-1-phenylethyl)carbamate;
(3-fluoro-4-methylphenyl) (4-(6-(isobutylamino)pyrimidin-4-yl)piperazin-1-yl)methanone;
(4-(6-isobutoxypyrimidin-4-yl)piperazin-1-yl)(6-methoxypyridin-2-yl)methanone;
(4-(6-isobutoxypyrimidin-4-yl)piperazin-1-yl)(1-methyl-3-(trifluoromethyl)-1H-pyrazol-5-yl)methanone;
(4-(6-isobutoxypyrimidin-4-yl)piperazin-1-yl)(3-(trifluoromethoxy)phenyl)methanone;
(4-(6-cyclobutoxypyrimidin-4-yl)piperazin-1-yl)(3-fluoro-4-methylphenyl)methanone;
4-(3-fluoro-4-methylbenzoyl)-1-(6-isobutoxypyrimidin-4-yl)piperazin-2-one;
(4-(6-isobutoxypyrimidin-4-yl)piperazin-1-yl)(quinolin-2-yl)methanone;
(4-fluorophenyl)(4-(6-isobutoxypyrimidin-4-yl)piperazin-1-yl)methanone;
(4-(6-isobutoxypyrimidin-4-yl)piperazin-1-yl)(1-methyl-5-(trifluoromethyl)-1H-pyrazol-3-yl)methanone;
(4-(6-isobutoxypyrimidin-4-yl)piperazin-1-yl)(2-methyl-2H-indazol-3-yl)methanone;
(4-(6-isobutoxypyrimidin-4-yl)piperazin-1-yl)(1-methyl-1H-indazol-3-yl)methanone;
(4-(6-isobutoxypyrimidin-4-yl)piperazin-1-yl)(1-methyl-1H-benzo[d]imidazol-2-yl)methanone;
2-(4-fluorophenoxy)-1-(4-(6-isobutoxypyrimidin-4-yl)piperazin-1-yl)ethanone;
(4-chloro-2-hydroxyphenyl) (4-(6-isobutoxypyrimidin-4-yl)piperazin-1-yl)methanone;
2-(2-(4-(6-isobutoxypyrimidin-4-yl)piperazin-1-yl)-2-oxoethyl)isoindolin-1-one;
(S)-2-amino-1-(4-(6-isobutoxypyrimidin-4-yl)piperazin-1-yl)-2-phenylethanone;
(R)-2-amino-1-(4-(6-isobutoxypyrimidin-4-yl)piperazin-1-yl)-2-phenylethanone;
(1-methyl-5-(trifluoromethyl)-1H-pyrazol-3-yl)(4-(6-(2,2,2-trifluoroethoxy)pyrimidin-4-yl)piperazin-1-yl)methanone;
(1-methyl-1H-indazol-3-yl)(4-(6-(2,2,2-trifluoroethoxy)pyrimidin-4-yl)piperazin-1-yl)methanone;
(4-(6-isobutoxypyrimidin-4-yl)piperazin-1-yl)(quinolin-3-yl)methanone;
(8-hydroxyquinolin-2-yl)(4-(6-isobutoxypyrimidin-4-yl)piperazin-1-yl)methanone;
(1H-indazol-3-yl)(4-(6-isobutoxypyrimidin-4-yl)piperazin-1-yl)methanone;

(4-(6-isobutoxypyrimidin-4-yl)piperazin-1-yl)(quinoxalin-2-yl)methanone;
(4-(6-isobutoxypyrimidin-4-yl)piperazin-1-yl)(isoquinolin-3-yl)methanone;
(4-(6-isobutoxypyrimidin-4-yl)piperazin-1-yl)(4-methoxyquinolin-2-yl)methanone;
(4-(6-cyclobutoxypyrimidin-4-yl)piperazin-1-yl)(quinolin-2-yl)methanone;
(4-(6-cyclobutoxypyrimidin-4-yl)piperazin-1-yl)(1-methyl-1H-indazol-3-yl)methanone;
(4-chloro-3-fluorophenyl) (4-(6-isobutoxypyrimidin-4-yl)piperazin-1-yl)methanone;
(4-fluoro-3-methylphenyl)(4-(6-isobutoxypyrimidin-4-yl)piperazin-1-yl)methanone;
(4-(6-isobutoxypyrimidin-4-yl)piperazin-1-yl)(pyrazolo[1,5-a]pyridin-2-yl)methanone;
(2-hydroxy-4-(trifluoromethyl)phenyl)(4-(6-isobutoxypyrimidin-4-yl)piperazin-1-yl)methanone;
(4-(6-isobutoxypyrimidin-4-yl)piperazin-1-yl)(1-methyl-1H-indol-2-yl)methanone;
(1-(2-hydroxyethyl)-1H-indazol-3-yl)(4-(6-isobutoxypyrimidin-4-yl)piperazin-1-yl)methanone;
1-(4-(6-isobutoxypyrimidin-4-yl)piperazin-1-yl)-2-phenoxyethanone;
(R)-1-(4-(6-isobutoxypyrimidin-4-yl)piperazin-1-yl)-2-phenoxypropan-1-one;
1-(4-(6-isobutoxypyrimidin-4-yl)piperazin-1-yl)-2-((6-(trifluoromethyl)pyridin-3-yl)oxy)ethanone;
2-(4-fluorophenoxy)-1-(4-(6-isobutoxypyrimidin-4-yl)piperazin-1-yl)propan-1-one;
(2,3-dihydrobenzofuran-2-yl)(4-(6-isobutoxypyrimidin-4-yl)piperazin-1-yl)methanone;
2-(4-fluorophenoxy)-1-(4-(6-(2,2,2-trifluoroethoxy)pyrimidin-4-yl)piperazin-1-yl)ethanone;
1-(4-(6-cyclobutoxypyrimidin-4-yl)piperazin-1-yl)-2-(4-fluorophenoxy)ethanone;
(4-(6-isobutoxypyrimidin-4-yl)piperazin-1-yl)(6-(pyrrolidin-1-yl)pyridin-2-yl)methanone;
benzyl 4-(6-isobutoxypyrimidin-4-yl)piperazine-1-carboxylate;
(4-(6-isobutoxypyrimidin-4-yl)piperazin-1-yl)(3-(trifluoromethyl)-1H-pyrazol-5-yl)methanone;
quinolin-2-yl(4-(6-(2,2,2-trifluoroethoxy)pyrimidin-4-yl)piperazin-1-yl)methanone;
(4-(6-cyclobutoxypyrimidin-4-yl)piperazin-1-yl)(4-fluorophenyl)methanone;
4-(2-(4-(6-isobutoxypyrimidin-4-yl)piperazin-1-yl)-2-oxoethyl)-2H-benzo[b][1,4]oxazin-3(4H)-one;
2-(benzo[d]isoxazol-3-yl)-1-(4-(6-isobutoxypyrimidin-4-yl)piperazin-1-yl)ethanone;
3-(1H-indol-1-yl)-1-(4-(6-isobutoxypyrimidin-4-yl)piperazin-1-yl)propan-1-one;
2-(5-fluoro-1H-indol-3-yl)-1-(4-(6-isobutoxypyrimidin-4-yl)piperazin-1-yl)ethanone;
2-(3-(4-(6-isobutoxypyrimidin-4-yl)piperazin-1-yl)-3-oxopropyl)isoindolin-1-one;
(4-(6-isobutoxypyrimidin-4-yl)piperazin-1-yl)(1-(2-methoxyethyl)-1H-indol-2-yl)methanone;
(4-methoxyquinolin-2-yl) (4-(6-(2,2,2-trifluoroethoxy)pyrimidin-4-yl)piperazin-1-yl)methanone;
quinoxalin-2-yl(4-(6-(2,2,2-trifluoroethoxy)pyrimidin-4-yl)piperazin-1-yl)methanone;
(8-hydroxyquinolin-2-yl)(4-(6-(2,2,2-trifluoroethoxy)pyrimidin-4-yl)piperazin-1-yl)methanone;
(1H-indol-4-yl)(4-(6-(2,2,2-trifluoroethoxy)pyrimidin-4-yl)piperazin-1-yl)methanone;
(2-methyl-2H-indazol-3-yl)(4-(6-(2,2,2-trifluoroethoxy)pyrimidin-4-yl)piperazin-1-yl)methanone;
(1H-indazol-3-yl)(4-(6-(2,2,2-trifluoroethoxy)pyrimidin-4-yl)piperazin-1-yl)methanone;
1-(4-(6-isobutoxypyrimidin-4-yl)piperazin-1-yl)-2-(phenylsulfonyl)ethanone;
1-(4-(6-isobutoxypyrimidin-4-yl)piperazin-1-yl)-2-(3-methoxyphenoxy)ethanone;
(1-(2-hydroxyethyl)-1H-indol-2-yl)(4-(6-isobutoxypyrimidin-4-yl)piperazin-1-yl)methanone;
4-fluoro-N-(2-(4-(6-isobutoxypyrimidin-4-yl)piperazin-1-yl)-2-oxoethyl)benzamide;
N-(2-(4-(6-isobutoxypyrimidin-4-yl)piperazin-1-yl)-2-oxoethyl)-6-methoxypicolinamide;
N-(2-(4-(6-isobutoxypyrimidin-4-yl)piperazin-1-yl)-2-oxoethyl)-6-(2,2,2-trifluoroethoxy)nicotinamide;
N-(2-(4-(6-isobutoxypyrimidin-4-yl)piperazin-1-yl)-2-oxoethyl)-1H-indole-4-carboxamide;
N-(2-(4-(6-isobutoxypyrimidin-4-yl)piperazin-1-yl)-2-oxoethyl)-1-methyl-1H-indazole-3-carboxamide;
1-(4-(6-isobutoxypyrimidin-4-yl)piperazin-1-yl)-2-(quinolin-8-yloxy)ethanone;
1-(4-(6-isobutoxypyrimidin-4-yl)piperazin-1-yl)-2-(quinolin-5-yloxy)ethanone;
1-(4-(6-isobutoxypyrimidin-4-yl)piperazin-1-yl)-2-((6-methylpyridin-3-yl)oxy)ethanone;
(4-(6-cyclobutoxypyrimidin-4-yl)piperazin-1-yl)(2-methyl-2H-indazol-3-yl)methanone
(4-(6-cyclobutoxypyrimidin-4-yl)piperazin-1-yl)(1H-indazol-3-yl)methanone;
(4-(6-cyclobutoxypyrimidin-4-yl)piperazin-1-yl)(quinoxalin-2-yl)methanone;
(4-(6-cyclobutoxypyrimidin-4-yl)piperazin-1-yl)(8-hydroxyquinolin-2-yl)methanone;
(4-(6-cyclobutoxypyrimidin-4-yl)piperazin-1-yl)(1-methyl-3-(trifluoromethyl)-1H-pyrazol-5-yl)methanone;
N-(2-(4-(6-cyclobutoxypyrimidin-4-yl)piperazin-1-yl)-2-oxoethyl)benzamide; benzo[b]thiophen-2-yl(4-(6-isobutoxypyrimidin-4-yl)piperazin-1-yl)methanone;
(4-(6-isobutoxypyrimidin-4-yl)piperazin-1-yl)(thieno[2,3-b]pyridin-2-yl)methanone;
(4-(6-isobutoxypyrimidin-4-yl)piperazin-1-yl)(thieno[2,3-b]pyrazin-6-yl)methanone;
3-(4-fluorophenoxy)-1-(4-(6-isobutoxypyrimidin-4-yl)piperazin-1-yl)propan-1-one;
(4-(6-isobutoxypyrimidin-4-yl)piperazin-1-yl)(5-phenylisoxazol-3-yl)methanone;
(4-(6-isobutoxypyrimidin-4-yl)piperazin-1-yl)(5-methyl-1-phenyl-1H-pyrazol-3-yl)methanone;
(4-(6-isobutoxypyrimidin-4-yl)piperazin-1-yl)(4-(oxazol-5-yl)phenyl)methanone;
(4-(1H-pyrazol-1-yl)phenyl)(4-(6-isobutoxypyrimidin-4-yl)piperazin-1-yl)methanone;
(3-fluoro-4-methylphenyl)((1S,4S)-5-(6-isobutoxypyrimidin-4-yl)-2,5-diazabicyclo[2.2.1]heptan-2-yl)methanone;
2-(4-fluorophenoxy)-1-((1S,4S)-5-(6-isobutoxypyrimidin-4-yl)-2,5-diazabicyclo[2.2.1]heptan-2-yl)ethanone;
2-(3-fluorophenoxy)-1-(4-(6-isobutoxypyrimidin-4-yl)piperazin-1-yl)ethanone;
2-(3,4-difluorophenoxy)-1-(4-(6-isobutoxypyrimidin-4-yl)piperazin-1-yl)ethanone;
2-(2-(4-(6-isobutoxypyrimidin-4-yl)piperazin-1-yl)-2-oxoethyl)-3,4-dihydroisoquinolin-1(2H)-one;
1-(2-(4-(6-isobutoxypyrimidin-4-yl)piperazin-1-yl)-2-oxoethyl)-3,4-dihydroquinolin-2(1H)-one;
2-(cyclohexylamino)-1-(4-(6-isobutoxypyrimidin-4-yl)piperazin-1-yl)ethanone;

1-(4-(6-isobutoxypyrimidin-4-yl)piperazin-1-yl)-2-(1-methyl-1H-indol-3-yl)ethanone;
2-(1H-indol-3-yl)-1-(4-(6-isobutoxypyrimidin-4-yl)piperazin-1-yl)ethanone;
3-(2-(4-(6-isobutoxypyrimidin-4-yl)piperazin-1-yl)-2-oxoethyl)benzo[d]oxazol-2(3H)-one;
2-(1H-benzo[d]imidazol-2-yl)-1-(4-(6-isobutoxypyrimidin-4-yl)piperazin-1-yl)ethanone;
2-(2H-benzo[d][1,2,3]triazol-2-yl)-1-(4-(6-isobutoxypyrimidin-4-yl)piperazin-1-yl)ethanone;
2-(benzyloxy)-1-(4-(6-isobutoxypyrimidin-4-yl)piperazin-1-yl)ethanone;
2-(benzo[d]isoxazol-3-yl)-1-(4-(6-(2,2,2-trifluoroethoxy)pyrimidin-4-yl)piperazin-1-yl)ethanone;
2-(2-oxo-2-(4-(6-(2,2,2-trifluoroethoxy)pyrimidin-4-yl)piperazin-1-yl)ethyl)isoindolin-1-one;
2-(3-oxo-3-(4-(6-(2,2,2-trifluoroethoxy)pyrimidin-4-yl)piperazin-1-yl)propyl)isoindolin-1-one;
2-(5-fluoro-1H-indol-3-yl)-1-(4-(6-(2,2,2-trifluoroethoxy)pyrimidin-4-yl)piperazin-1-yl)ethanone;
2-(benzo[d]isoxazol-3-yl)-1-(4-(6-cyclobutoxypyrimidin-4-yl)piperazin-1-yl)ethanone;
(4-(6-cyclobutoxypyrimidin-4-yl)piperazin-1-yl)(thieno[2,3-b]pyridin-2-yl)methanone; (4-(6-cyclobutoxypyrimidin-4-yl)piperazin-1-yl)(2,3-dihydrobenzofuran-2-yl)methanone;
(4-(6-cyclobutoxypyrimidin-4-yl)piperazin-1-yl)(4-methoxyquinolin-2-yl)methanone;
(4-(6-cyclobutoxypyrimidin-4-yl)piperazin-1-yl)(isoquinolin-3-yl)methanone;
(5-fluoro-1H-indazol-3-yl)(4-(6-(2,2,2-trifluoroethoxy)pyrimidin-4-yl)piperazin-1-yl)methanone;
(4-(6-isopropoxypyrimidin-4-yl)piperazin-1-yl)(1-methyl-1H-indazol-3-yl)methanone;
4-fluoro-N-(3-(4-(6-isobutoxypyrimidin-4-yl)piperazin-1-yl)-3-oxopropyl)benzamide;
2-(4-fluorophenyl)-1-(4-(6-isobutoxypyrimidin-4-yl)piperazin-1-yl)ethanone;
1-(4-(6-isobutoxypyrimidin-4-yl)piperazin-1-yl)-2-(phenylthio)ethanone;
2-((4-chlorophenyl)sulfonyl)-1-(4-(6-isobutoxypyrimidin-4-yl)piperazin-1-yl)ethanone;
2-((4-fluorophenyl)sulfonyl)-1-(4-(6-isobutoxypyrimidin-4-yl)piperazin-1-yl)ethanone;
(S)— (1-(3-fluoro-4-methylbenzoyl)pyrrolidin-2-yl)(4-(6-isobutoxypyrimidin-4-yl)piperazin-1-yl)methanone;
(1,3-dimethyl-1H-thieno[2,3-c]pyrazol-5-yl)(4-(6-isobutoxypyrimidin-4-yl)piperazin-1-yl)methanone;
(4-(6-isobutoxypyrimidin-4-yl)piperazin-1-yl)(thiophen-2-yl)methanone;
imidazo[2,1-b]thiazol-6-yl(4-(6-isobutoxypyrimidin-4-yl)piperazin-1-yl)methanone;
1-(4-(6-isobutoxypyrimidin-4-yl)piperazin-1-yl)-2-(quinolin-7-yloxy)ethanone;
1-(4-(6-isobutoxypyrimidin-4-yl)piperazin-1-yl)-2-(isoquinolin-8-yloxy)ethanone;
2-((5-fluoroquinolin-8-yl)oxy)-1-(4-(6-isobutoxypyrimidin-4-yl)piperazin-1-yl)ethanone;
(2-(ethylsulfonyl)phenyl) (4-(6-isobutoxypyrimidin-4-yl)piperazin-1-yl)methanone;
1-(4-(6-isobutoxypyrimidin-4-yl)piperazin-1-yl)-3-phenoxypropan-1-one;
1-(4-(6-isobutoxypyrimidin-4-yl)piperazin-1-yl)-3-(m-tolyloxy)propan-1-one;
(4-(6-isobutoxypyrimidin-4-yl)piperazin-1-yl)(1-methyl-5-phenyl-1H-pyrazol-3-yl)methanone;
(4-(6-isobutoxypyrimidin-4-yl)piperazin-1-yl)(1-methyl-3-phenyl-1H-pyrazol-5-yl)methanone;
(4-(6-isobutoxypyrimidin-4-yl)piperazin-1-yl)(5-methyl-1-phenyl-1H-pyrazol-4-yl)methanone;
(4-(6-isobutoxypyrimidin-4-yl)piperazin-1-yl)(5-methyl-1-phenyl-1H-1,2,3-triazol-4-yl)methanone;
2-((1H-indol-4-yl)oxy)-1-(4-(6-isobutoxypyrimidin-4-yl)piperazin-1-yl)ethanone;
2-(benzylsulfonyl)-1-(4-(6-isobutoxypyrimidin-4-yl)piperazin-1-yl)ethanone;
3-(4-fluorophenoxy)-1-(4-(6-(2,2,2-trifluoroethoxy)pyrimidin-4-yl)piperazin-1-yl)propan-1-one;
1-(4-(6-cyclobutoxypyrimidin-4-yl)piperazin-1-yl)-3-(4-fluorophenoxy)propan-1-one;
1-(4-(6-isobutoxypyrimidin-4-yl)piperazin-1-yl)-2-((1-methyl-1H-indol-4-yl)oxy)ethanone;
benzo[d]thiazol-2-yl(4-(6-isobutoxypyrimidin-4-yl)piperazin-1-yl)methanone;
1-(4-(6-isobutoxypyrimidin-4-yl)piperazin-1-yl)-2-(2-(trifluoromethyl)phenoxy)ethanone;
2-((5-chloropyridin-3-yl)oxy)-1-(4-(6-isobutoxypyrimidin-4-yl)piperazin-1-yl)ethanone;
1-(4-(6-isobutoxypyrimidin-4-yl)piperazin-1-yl)-2-(3-(trifluoromethoxy)phenoxy)ethanone;
2-(2H-benzo[d][1,2,3]triazol-2-yl)-1-(4-(6-(2,2,2-trifluoroethoxy)pyrimidin-4-yl)piperazin-1-yl)ethanone;
2-(quinazolin-4-yloxy)-1-(4-(6-(2,2,2-trifluoroethoxy)pyrimidin-4-yl)piperazin-1-yl)ethanone;
(5-methyl-1-phenyl-1H-pyrazol-4-yl)(4-(6-(2,2,2-trifluoroethoxy)pyrimidin-4-yl)piperazin-1-yl)methanone;
1-(benzo[d]oxazol-2-ylmethyl)-4-(6-isobutoxypyrimidin-4-yl)piperazin-2-one;
1-(4-fluorobenzyl)-4-(6-(2,2,2-trifluoroethoxy)pyrimidin-4-yl)piperazin-2-one;
1-(4-(6-isobutoxypyrimidin-4-yl)piperazin-1-yl)-2-methyl-2-(phenylsulfonyl)propan-1-one;
(R)-2-(4-fluorophenoxy)-1-(4-(6-isobutoxypyrimidin-4-yl)piperazin-1-yl)propan-1-one
(R)-1-(4-(6-cyclobutoxypyrimidin-4-yl)piperazin-1-yl)-2-(4-fluorophenoxy)propan-1-one;
2-(benzyloxy)-1-(4-(6-cyclobutoxypyrimidin-4-yl)piperazin-1-yl)ethanone;
2-(3-fluorophenoxy)-1-(4-(6-(2,2,2-trifluoroethoxy)pyrimidin-4-yl)piperazin-1-yl)ethanone;
2-(quinolin-8-yloxy)-1-(4-(6-(2,2,2-trifluoroethoxy)pyrimidin-4-yl)piperazin-1-yl)ethanone;
2-(2-oxo-2-(4-(6-(2,2,2-trifluoroethoxy)pyrimidin-4-yl)piperazin-1-yl)ethyl)-3,4-dihydroisoquinolin-1(2H)-one;
1-(2-oxo-2-(4-(6-(2,2,2-trifluoroethoxy)pyrimidin-4-yl)piperazin-1-yl)ethyl)-3,4-dihydroquinolin-2(1H)-one;
2-(chroman-4-yloxy)-1-(4-(6-isobutoxypyrimidin-4-yl)piperazin-1-yl)ethanone;
1-(4-(6-isobutoxypyrimidin-4-yl)piperazin-1-yl)-2-(quinolin-2-yloxy)ethanone;
2-(chroman-4-yloxy)-1-(4-(6-(2,2,2-trifluoroethoxy)pyrimidin-4-yl)piperazin-1-yl)ethanone;
2-((1H-indol-4-yl)oxy)-1-(4-(6-(2,2,2-trifluoroethoxy)pyrimidin-4-yl)piperazin-1-yl)ethanone;
1-(4-(6-isobutoxypyrimidin-4-yl)piperazin-1-yl)-2-phenylethane-1,2-dione;
(4-(6-isopropoxypyrimidin-4-yl)piperazin-1-yl)(1-methyl-3-phenyl-1H-pyrazol-5-yl)methanone;
(4-(6-isopropoxypyrimidin-4-yl)piperazin-1-yl)(2-phenylthiazol-4-yl)methanone;
(2-phenylthiazol-4-yl)(4-(6-(2,2,2-trifluoroethoxy)pyrimidin-4-yl)piperazin-1-yl)methanone;

(2-benzylthiazol-4-yl)(4-(6-isobutoxypyrimidin-4-yl)piperazin-1-yl)methanone;
2-((4-fluorobenzyl)oxy)-1-(4-(6-isobutoxypyrimidin-4-yl)piperazin-1-yl)ethanone;
(1-(4-fluorophenyl)-5-methyl-1H-pyrazol-4-yl)(4-(6-isobutoxypyrimidin-4-yl)piperazin-1-yl)methanone;
(4-(6-isobutoxypyrimidin-4-yl)piperazin-1-yl)(1-(4-methoxyphenyl)-5-methyl-1H-pyrazol-4-yl)methanone;
(1-benzyl-1H-pyrazol-4-yl)(4-(6-isobutoxypyrimidin-4-yl)piperazin-1-yl)methanone;
(4-(6-isobutoxypyrimidin-4-yl)piperazin-1-yl)(5-methyl-3-phenylisoxazol-4-yl)methanone;
(4-(6-isobutoxypyrimidin-4-yl)piperazin-1-yl)(3-methyl-5-phenylisoxazol-4-yl)methanone;
(5-(2-fluorophenyl)oxazol-4-yl)(4-(6-isobutoxypyrimidin-4-yl)piperazin-1-yl)methanone;
(4-(6-isobutoxypyrimidin-4-yl)piperazin-1-yl)(3-(2-methoxyphenyl)-1H-pyrazol-5-yl)methanone;
2-((3-fluorophenyl)sulfonyl)-1-(4-(6-isobutoxypyrimidin-4-yl)piperazin-1-yl)ethanone;
1-(4-(6-isobutoxypyrimidin-4-yl)piperazin-1-yl)-2-((3-methoxyphenyl)sulfonyl)ethanone;
1-(4-(6-cyclobutoxypyrimidin-4-yl)piperazin-1-yl)-2-((3-fluorophenyl)sulfonyl)ethanone;
1-(4-(6-cyclobutoxypyrimidin-4-yl)piperazin-1-yl)-2-((3-methoxyphenyl)sulfonyl)ethanone;
(2-((2-hydroxyethyl)thio)phenyl)(4-(6-isobutoxypyrimidin-4-yl)piperazin-1-yl)methanone;
(5-methyl-1-phenyl-1H-1,2,3-triazol-4-yl)(4-(6-(2,2,2-trifluoroethoxy)pyrimidin-4-yl)piperazin-1-yl)methanone;
(4-(6-isobutoxypyrimidin-4-yl)piperazin-1-yl)(5-methyl-2-phenyl-2H-1,2,3-triazol-4-yl)methanone;
(4-(6-isobutoxypyrimidin-4-yl)piperazin-1-yl)(1-(2-methoxyphenyl)-1H-pyrazol-4-yl)methanone;
(5-amino-1-phenyl-1H-pyrazol-4-yl)(4-(6-isobutoxypyrimidin-4-yl)piperazin-1-yl)methanone;
(4-(6-isobutoxypyrimidin-4-yl)piperazin-1-yl)(6-phenylpyrimidin-4-yl)methanone;
(3-(1H-pyrazol-1-yl)phenyl)(4-(6-isobutoxypyrimidin-4-yl)piperazin-1-yl)methanone;
(4-(6-isobutoxypyrimidin-4-yl)piperazin-1-yl)(3-(2-methylthiazol-4-yl)phenyl)methanone;
(4-(6-isobutoxypyrimidin-4-yl)piperazin-1-yl)(3-(pyridin-3-yl)-1H-pyrazol-5-yl)methanone;
(4-(6-isobutoxypyrimidin-4-yl)piperazin-1-yl)(1-methyl-3-(pyridin-3-yl)-1H-pyrazol-5-yl)methanone;
(4-(6-isobutoxypyrimidin-4-yl)piperazin-1-yl)(2-(pyridin-3-yl)thiazol-4-yl)methanone;
(4-(6-isobutoxypyrimidin-4-yl)piperazin-1-yl)(2-(pyridin-2-yl)thiazol-4-yl)methanone;
(4-(6-isopropoxypyrimidin-4-yl)piperazin-1-yl)(2-(pyridin-3-yl)thiazol-4-yl)methanone;
(4-(6-isopropoxypyrimidin-4-yl)piperazin-1-yl)(2-(pyridin-2-yl)thiazol-4-yl)methanone;
(4-(6-isobutoxypyrimidin-4-yl)piperazin-1-yl)(1-methyl-1H-pyrazolo[3,4-b]pyridin-3-yl)methanone;
(1-methyl-1H-pyrazolo[3,4-b]pyridin-3-yl)(4-(6-(2,2,2-trifluoroethoxy)pyrimidin-4-yl)piperazin-1-yl)methanone;
benzo[d][1,2,3]thiadiazol-7-yl(4-(6-isobutoxypyrimidin-4-yl)piperazin-1-yl)methanone
1-(4-(6-cyclobutoxypyrimidin-4-yl)piperazin-1-yl)-2-((1-methyl-1H-indol-4-yl)oxy)ethanone;
1-(4-(6-isopropoxypyrimidin-4-yl)piperazin-1-yl)-2-((1-methyl-1H-indol-4-yl)oxy)ethanone;
(5-fluoro-1H-indazol-3-yl)(4-(6-isobutoxypyrimidin-4-yl)piperazin-1-yl)methanone;
(5-fluoro-1H-indazol-3-yl)(4-(6-isopropoxypyrimidin-4-yl)piperazin-1-yl)methanone;
(4-(6-cyclobutoxypyrimidin-4-yl)piperazin-1-yl)(5-fluoro-1H-indazol-3-yl)methanone;
(1-(4-fluorophenyl)-5-methyl-1H-1,2,3-triazol-4-yl)(4-(6-isobutoxypyrimidin-4-yl)piperazin-1-yl)methanone;
(1-(4-fluorophenyl)-5-methyl-1H-1,2,3-triazol-4-yl)(4-(6-isopropoxypyrimidin-4-yl)piperazin-1-yl)methanone;
(4-(6-cyclobutoxypyrimidin-4-yl)piperazin-1-yl)(1-(4-fluorophenyl)-5-methyl-1H-1,2,3-triazol-4-yl)methanone;
(1-(4-fluorophenyl)-5-methyl-1H-1,2,3-triazol-4-yl)(4-(6-(2,2,2-trifluoroethoxy)pyrimidin-4-yl)piperazin-1-yl)methanone;
(4-(6-isobutoxypyrimidin-4-yl)piperazin-1-yl)(1-phenyl-1H-1,2,3-triazol-4-yl)methanone;
(4-(6-isobutoxypyrimidin-4-yl)piperazin-1-yl)(3-(pyridin-2-yl)-1H-pyrazol-5-yl)methanone;
(4-(6-isobutoxypyrimidin-4-yl)piperazin-1-yl)(4-methyl-2-phenyloxazol-5-yl)methanone;
(5-fluoro-1-methyl-1H-indazol-3-yl)(4-(6-isobutoxypyrimidin-4-yl)piperazin-1-yl)methanone;
(5-fluoro-1-methyl-1H-indazol-3-yl)(4-(6-isopropoxypyrimidin-4-yl)piperazin-1-yl)methanone;
(4-(6-cyclobutoxypyrimidin-4-yl)piperazin-1-yl)(5-fluoro-1-methyl-1H-indazol-3-yl)methanone;
(5-fluoro-1-methyl-1H-indazol-3-yl)(4-(6-(2,2,2-trifluoroethoxy)pyrimidin-4-yl)piperazin-1-yl)methanone;
(4-(6-isobutoxypyrimidin-4-yl)piperazin-1-yl)(2-phenylthiazol-4-yl)methanone;
(6-(1H-pyrazol-1-yl)pyridin-3-yl)(4-(6-isobutoxypyrimidin-4-yl)piperazin-1-yl)methanone;
(4-(6-isobutoxypyrimidin-4-yl)piperazin-1-yl)(1-phenyl-1H-pyrazol-4-yl)methanone;
(1-phenyl-1H-pyrazol-4-yl)(4-(6-(2,2,2-trifluoroethoxy)pyrimidin-4-yl)piperazin-1-yl)methanone;
(1-ethyl-3-(trifluoromethyl)-1H-pyrazol-5-yl)(4-(6-isobutoxypyrimidin-4-yl)piperazin-1-yl)methanone;
(1-ethyl-3-(trifluoromethyl)-1H-pyrazol-5-yl)(4-(6-(2,2,2-trifluoroethoxy)pyrimidin-4-yl)piperazin-1-yl)methanone;
(4-(6-cyclobutoxypyrimidin-4-yl)piperazin-1-yl)(5-methyl-1-phenyl-1H-1,2,3-triazol-4-yl)methanone;
2-(2H-benzo[d][1,2,3]triazol-2-yl)-1-(4-(6-cyclobutoxypyrimidin-4-yl)piperazin-1-yl)ethanone; benzo[c]isoxazol-3-yl(4-(6-isobutoxypyrimidin-4-yl)piperazin-1-yl)methanone;
(4-(6-isobutoxypyrimidin-4-yl)piperazin-1-yl)(4,5,6,7-tetrahydro-1H-indazol-3-yl)methanone;
(4-(6-isobutoxypyrimidin-4-yl)piperazin-1-yl)(2-methyl-4,5,6,7-tetrahydro-2H-indazol-3-yl)methanone;
2-(2-(4-(6-cyclobutoxypyrimidin-4-yl)piperazin-1-yl)-2-oxoethyl)-3,4-dihydroisoquinolin-1(2H)-one;
(4-(6-cyclobutoxypyrimidin-4-yl)piperazin-1-yl)(1-methyl-1H-benzo[d]imidazol-2-yl)methanone;
(4-(6-isobutoxypyrimidin-4-yl)piperazin-1-yl)(5-(6-methoxypyridin-3-yl)-1-methyl-1H-pyrazol-3-yl)methanone;
(4-(6-cyclobutoxypyrimidin-4-yl)piperazin-1-yl)(pyrazolo[1,5-a]pyridin-2-yl)methanone;
(1-ethyl-5-(trifluoromethyl)-1H-pyrazol-3-yl)(4-(6-isobutoxypyrimidin-4-yl)piperazin-1-yl)methanone;
(1-ethyl-5-(trifluoromethyl)-1H-pyrazol-3-yl)(4-(6-(2,2,2-trifluoroethoxy)pyrimidin-4-yl)piperazin-1-yl)methanone;
(4-(6-isobutoxypyrimidin-4-yl)piperazin-1-yl)(1-(pyridin-2-yl)-1H-pyrazol-4-yl)methanone;
(6-ethoxypyridin-2-yl) (4-(6-isobutoxypyrimidin-4-yl)piperazin-1-yl)methanone;

(4-(6-isobutoxypyrimidin-4-yl)piperazin-1-yl)(6-(2,2,2-trifluoroethoxy)pyridin-2-yl)methanone;
(4-(6-isobutoxypyrimidin-4-yl)piperazin-1-yl)(2-isopropylthiazol-4-yl)methanone;
(3-cyclopropyl-1-methyl-1H-pyrazol-5-yl)(4-(6-isobutoxypyrimidin-4-yl)piperazin-1-yl)methanone;
(5-cyclopropyl-1-methyl-1H-pyrazol-3-yl)(4-(6-isobutoxypyrimidin-4-yl)piperazin-1-yl)methanone;
2-(2-(4-(6-isobutoxypyrimidin-4-yl)piperazin-1-yl)-2-oxoethyl)isoquinolin-1(2H)-one;
2-(2-oxo-2-(4-(6-(2,2,2-trifluoroethoxy)pyrimidin-4-yl)piperazin-1-yl)ethyl)isoquinolin-1(2H)-one;
(4-(6-isobutoxypyrimidin-4-yl)piperazin-1-yl) (2-(trifluoromethyl)thiazol-4-yl)methanone;
(4-(6-(2,2,2-trifluoroethoxy)pyrimidin-4-yl)piperazin-1-yl) (2-(trifluoromethyl)thiazol-4-yl)methanone;
2-(2H-indazol-2-yl)-1-(4-(6-isobutoxypyrimidin-4-yl)piperazin-1-yl)ethanone;
(4-(6-ethoxypyrimidin-4-yl)piperazin-1-yl) (2-(pyridin-2-yl)thiazol-4-yl)methanone;
(5-(2-fluorophenyl)oxazol-4-yl)(4-(6-(2,2,2-trifluoroethoxy)pyrimidin-4-yl)piperazin-1-yl)methanone;
(4-(6-(2,2,2-trifluoroethoxy)pyrimidin-4-yl)piperazin-1-yl) (1-(2-(trifluoromethyl)phen yl)-1H-imidazol-5-yl)methanone;
(2-(pyridin-2-yl)thiazol-4-yl) (4-(6-(2,2,2-trifluoroethoxy)pyrimidin-4-yl)piperazin-1-yl)methanone;
(5-methyl-3-phenylisoxazol-4-yl)(4-(6-(2,2,2-trifluoroethoxy)pyrimidin-4-yl)piperazin-1-yl)methanone; and
(2-(1H-pyrazol-3-yl)phenyl) (4-(6-(2,2,2-trifluoroethoxy)pyrimidin-4-yl)piperazin-1-yl)methanone; or
a prodrug thereof or a pharmaceutically acceptable salt thereof.

The more preferable compound as described above, which is selected from:
(R)-2-hydroxy-1-(4-(6-isobutoxypyrimidin-4-yl)piperazin-1-yl)-3-phenylpropan-1-one;
(4-(6-(cyclopentyloxy)pyrimidin-4-yl)piperazin-1-yl)(3-fluoro-4-methylphenyl)methanone;
(3-fluoro-4-methylphenyl) (4-(6-(2,2,2-trifluoroethoxy)pyrimidin-4-yl)piperazin-1-yl)methanone;
(1H-indol-4-yl)(4-(6-isobutoxypyrimidin-4-yl)piperazin-1-yl)methanone;
(S)-tert-butyl(2-(4-(6-isobutoxypyrimidin-4-yl)piperazin-1-yl)-2-oxo-1-phenylethyl)carbamate;
(R)-tert-butyl(2-(4-(6-isobutoxypyrimidin-4-yl)piperazin-1-yl)-2-oxo-1-phenylethyl)carbamate;
(4-(6-isobutoxypyrimidin-4-yl)piperazin-1-yl)(1-methyl-3-(trifluoromethyl)-1H-pyrazol-5-yl)methanone;
(4-(6-isobutoxypyrimidin-4-yl)piperazin-1-yl)(3-(trifluoromethoxy)phenyl)methanone;
(4-(6-cyclobutoxypyrimidin-4-yl)piperazin-1-yl)(3-fluoro-4-methylphenyl)methanone;
(4-(6-isobutoxypyrimidin-4-yl)piperazin-1-yl)(quinolin-2-yl)methanone;
(4-(6-isobutoxypyrimidin-4-yl)piperazin-1-yl)(1-methyl-1H-indazol-3-yl)methanone;
(4-(6-isobutoxypyrimidin-4-yl)piperazin-1-yl)(1-methyl-1H-benzo[d]imidazol-2-yl)methanone;
2-(4-fluorophenoxy)-1-(4-(6-isobutoxypyrimidin-4-yl)piperazin-1-yl)ethanone;
(S)-2-amino-1-(4-(6-isobutoxypyrimidin-4-yl)piperazin-1-yl)-2-phenylethanone;
(R)-2-amino-1-(4-(6-isobutoxypyrimidin-4-yl)piperazin-1-yl)-2-phenylethanone;
(1-methyl-5-(trifluoromethyl)-1H-pyrazol-3-yl)(4-(6-(2,2,2-trifluoroethoxy)pyrimidin-4-yl)piperazin-1-yl)methanone;
(1-methyl-1H-indazol-3-yl)(4-(6-(2,2,2-trifluoroethoxy)pyrimidin-4-yl)piperazin-1-yl)methanone;
(8-hydroxyquinolin-2-yl)(4-(6-isobutoxypyrimidin-4-yl)piperazin-1-yl)methanone;
(4-(6-isobutoxypyrimidin-4-yl)piperazin-1-yl)(quinoxalin-2-yl)methanone;
(4-(6-cyclobutoxypyrimidin-4-yl)piperazin-1-yl)(1-methyl-1H-indazol-3-yl)methanone;
(4-chloro-3-fluorophenyl) (4-(6-isobutoxypyrimidin-4-yl)piperazin-1-yl)methanone;
(2-hydroxy-4-(trifluoromethyl)phenyl)(4-(6-isobutoxypyrimidin-4-yl)piperazin-1-yl)methanone;
(4-(6-isobutoxypyrimidin-4-yl)piperazin-1-yl)(1-methyl-1H-indol-2-yl)methanone;
2-(4-fluorophenoxy)-1-(4-(6-isobutoxypyrimidin-4-yl)piperazin-1-yl)propan-1-one;
(4-(6-isobutoxypyrimidin-4-yl)piperazin-1-yl)(6-(pyrrolidin-1-yl)pyridin-2-yl)methanone;
benzyl 4-(6-isobutoxypyrimidin-4-yl)piperazine-1-carboxylate;
4-(2-(4-(6-isobutoxypyrimidin-4-yl)piperazin-1-yl)-2-oxoethyl)-2H-benzo[b][1,4]oxazin-3(4H)-one;
2-(benzo[d]isoxazol-3-yl)-1-(4-(6-isobutoxypyrimidin-4-yl)piperazin-1-yl)ethanone;
3-(1H-indol-1-yl)-1-(4-(6-isobutoxypyrimidin-4-yl)piperazin-1-yl)propan-1-one;
2-(5-fluoro-1H-indol-3-yl)-1-(4-(6-isobutoxypyrimidin-4-yl)piperazin-1-yl)ethanone;
2-(3-(4-(6-isobutoxypyrimidin-4-yl)piperazin-1-yl)-3-oxopropyl)isoindolin-1-one;
(4-(6-isobutoxypyrimidin-4-yl)piperazin-1-yl)(1-(2-methoxyethyl)-1H-indol-2-yl)methanone;
(4-methoxyquinolin-2-yl) (4-(6-(2,2,2-trifluoroethoxy)pyrimidin-4-yl)piperazin-1-yl)methanone;
(8-hydroxyquinolin-2-yl)(4-(6-(2,2,2-trifluoroethoxy)pyrimidin-4-yl)piperazin-1-yl)methanone;
(1H-indazol-3-yl)(4-(6-(2,2,2-trifluoroethoxy)pyrimidin-4-yl)piperazin-1-yl)methanone;
1-(4-(6-isobutoxypyrimidin-4-yl)piperazin-1-yl)-2-(3-methoxyphenoxy)ethanone;
N-(2-(4-(6-isobutoxypyrimidin-4-yl)piperazin-1-yl)-2-oxoethyl)-6-methoxypicolinamide;
N-(2-(4-(6-isobutoxypyrimidin-4-yl)piperazin-1-yl)-2-oxoethyl)-6-(2,2,2-trifluoroethoxy)nicotinamide;
N-(2-(4-(6-isobutoxypyrimidin-4-yl)piperazin-1-yl)-2-oxoethyl)-1H-indole-4-carboxamide;
N-(2-(4-(6-isobutoxypyrimidin-4-yl)piperazin-1-yl)-2-oxoethyl)-1-methyl-1H-indazole-3-carboxamide;
1-(4-(6-isobutoxypyrimidin-4-yl)piperazin-1-yl)-2-(quinolin-8-yloxy)ethanone;
1-(4-(6-isobutoxypyrimidin-4-yl)piperazin-1-yl)-2-(quinolin-5-yloxy)ethanone;
(4-(6-cyclobutoxypyrimidin-4-yl)piperazin-1-yl)(quinoxalin-2-yl)methanone;
(4-(6-cyclobutoxypyrimidin-4-yl)piperazin-1-yl)(8-hydroxyquinolin-2-yl)methanone;
N-(2-(4-(6-cyclobutoxypyrimidin-4-yl)piperazin-1-yl)-2-oxoethyl)benzamide; benzo[b]thiophen-2-yl(4-(6-isobutoxypyrimidin-4-yl)piperazin-1-yl)methanone;
3-(4-fluorophenoxy)-1-(4-(6-isobutoxypyrimidin-4-yl)piperazin-1-yl)propan-1-one;
(4-(6-isobutoxypyrimidin-4-yl)piperazin-1-yl)(5-phenylisoxazol-3-yl)methanone;

(4-(6-isobutoxypyrimidin-4-yl)piperazin-1-yl)(5-methyl-1-phenyl-1H-pyrazol-3-yl)methanone;
(4-(6-isobutoxypyrimidin-4-yl)piperazin-1-yl)(4-(oxazol-5-yl)phenyl)methanone;
(4-(1H-pyrazol-1-yl)phenyl)(4-(6-isobutoxypyrimidin-4-yl)piperazin-1-yl)methanone;
(3-fluoro-4-methylphenyl)((1S,4S)-5-(6-isobutoxypyrimidin-4-yl)-2,5-diazabicyclo[2.2.1]heptan-2-yl)methanone;
2-(3-fluorophenoxy)-1-(4-(6-isobutoxypyrimidin-4-yl)piperazin-1-yl)ethanone;
2-(3,4-difluorophenoxy)-1-(4-(6-isobutoxypyrimidin-4-yl)piperazin-1-yl)ethanone;
2-(2-(4-(6-isobutoxypyrimidin-4-yl)piperazin-1-yl)-2-oxoethyl)-3,4-dihydroisoquinolin-1(2H)-one;
2-(cyclohexylamino)-1-(4-(6-isobutoxypyrimidin-4-yl)piperazin-1-yl)ethanone;
1-(4-(6-isobutoxypyrimidin-4-yl)piperazin-1-yl)-2-(1-methyl-1H-indol-3-yl)ethanone;
2-(1H-indol-3-yl)-1-(4-(6-isobutoxypyrimidin-4-yl)piperazin-1-yl)ethanone;
2-(2H-benzo[d][1,2,3]triazol-2-yl)-1-(4-(6-isobutoxypyrimidin-4-yl)piperazin-1-yl)ethanone;
2-(benzyloxy)-1-(4-(6-isobutoxypyrimidin-4-yl)piperazin-1-yl)ethanone;
2-(benzo[d]isoxazol-3-yl)-1-(4-(6-(2,2,2-trifluoroethoxy)pyrimidin-4-yl)piperazin-1-yl)ethanone;
2-(5-fluoro-1H-indol-3-yl)-1-(4-(6-(2,2,2-trifluoroethoxy)pyrimidin-4-yl)piperazin-1-yl)ethanone;
2-(benzo[d]isoxazol-3-yl)-1-(4-(6-cyclobutoxypyrimidin-4-yl)piperazin-1-yl)ethanone;
2-(4-fluorophenyl)-1-(4-(6-isobutoxypyrimidin-4-yl)piperazin-1-yl)ethanone;
1-(4-(6-isobutoxypyrimidin-4-yl)piperazin-1-yl)-2-(phenylthio)ethanone;
2-((4-chlorophenyl)sulfonyl)-1-(4-(6-isobutoxypyrimidin-4-yl)piperazin-1-yl)ethanone
1-(4-(6-isobutoxypyrimidin-4-yl)piperazin-1-yl)-2-(quinolin-7-yloxy)ethanone;
1-(4-(6-isobutoxypyrimidin-4-yl)piperazin-1-yl)-2-(isoquinolin-8-yloxy)ethanone;
2-((5-fluoroquinolin-8-yl)oxy)-1-(4-(6-isobutoxypyrimidin-4-yl)piperazin-1-yl)ethanone;
1-(4-(6-isobutoxypyrimidin-4-yl)piperazin-1-yl)-3-phenoxypropan-1-one;
1-(4-(6-isobutoxypyrimidin-4-yl)piperazin-1-yl)-3-(m-tolyloxy)propan-1-one;
(4-(6-isobutoxypyrimidin-4-yl)piperazin-1-yl)(1-methyl-5-phenyl-1H-pyrazol-3-yl)methanone;
(4-(6-isobutoxypyrimidin-4-yl)piperazin-1-yl)(1-methyl-3-phenyl-1H-pyrazol-5-yl)methanone;
(4-(6-isobutoxypyrimidin-4-yl)piperazin-1-yl)(5-methyl-1-phenyl-1H-pyrazol-4-yl)methanone;
(4-(6-isobutoxypyrimidin-4-yl)piperazin-1-yl)(5-methyl-1-phenyl-1H-1,2,3-triazol-4-yl)methanone;
2-((1H-indol-4-yl)oxy)-1-(4-(6-isobutoxypyrimidin-4-yl)piperazin-1-yl)ethanone;
3-(4-fluorophenoxy)-1-(4-(6-(2,2,2-trifluoroethoxy)pyrimidin-4-yl)piperazin-1-yl)propan-1-one;
1-(4-(6-cyclobutoxypyrimidin-4-yl)piperazin-1-yl)-3-(4-fluorophenoxy)propan-1-one;
1-(4-(6-isobutoxypyrimidin-4-yl)piperazin-1-yl)-2-((1-methyl-1H-indol-4-yl)oxy)ethanone;
1-(4-(6-isobutoxypyrimidin-4-yl)piperazin-1-yl)-2-(2-(trifluoromethyl)phenoxy)ethanone;
2-((5-chloropyridin-3-yl)oxy)-1-(4-(6-isobutoxypyrimidin-4-yl)piperazin-1-yl)ethanone;
1-(4-(6-isobutoxypyrimidin-4-yl)piperazin-1-yl)-2-(3-(trifluoromethoxy)phenoxy)ethanone;
2-(2H-benzo[d][1,2,3]triazol-2-yl)-1-(4-(6-(2,2,2-trifluoroethoxy)pyrimidin-4-yl)piperazin-1-yl)ethanone;
(5-methyl-1-phenyl-1H-pyrazol-4-yl)(4-(6-(2,2,2-trifluoroethoxy)pyrimidin-4-yl)piperazin-1-yl)methanone;
(R)-2-(4-fluorophenoxy)-1-(4-(6-isobutoxypyrimidin-4-yl)piperazin-1-yl)propan-1-one
2-(quinolin-8-yloxy)-1-(4-(6-(2,2,2-trifluoroethoxy)pyrimidin-4-yl)piperazin-1-yl)ethanone;
2-(2-oxo-2-(4-(6-(2,2,2-trifluoroethoxy)pyrimidin-4-yl)piperazin-1-yl)ethyl)-3,4-dihydroisoquinolin-1(2H)-one;
1-(4-(6-isobutoxypyrimidin-4-yl)piperazin-1-yl)-2-(quinolin-2-yloxy)ethanone;
2-(chroman-4-yloxy)-1-(4-(6-(2,2,2-trifluoroethoxy)pyrimidin-4-yl)piperazin-1-yl)ethanone;
(4-(6-isopropoxypyrimidin-4-yl)piperazin-1-yl)(1-methyl-3-phenyl-1H-pyrazol-5-yl)methanone;
(4-(6-isopropoxypyrimidin-4-yl)piperazin-1-yl)(2-phenylthiazol-4-yl)methanone;
(2-phenylthiazol-4-yl)(4-(6-(2,2,2-trifluoroethoxy)pyrimidin-4-yl)piperazin-1-yl)methanone;
(2-benzylthiazol-4-yl)(4-(6-isobutoxypyrimidin-4-yl)piperazin-1-yl)methanone;
2-((4-fluorobenzyl)oxy)-1-(4-(6-isobutoxypyrimidin-4-yl)piperazin-1-yl)ethanone;
(1-(4-fluorophenyl)-5-methyl-1H-pyrazol-4-yl)(4-(6-isobutoxypyrimidin-4-yl)piperazin-1-yl)methanone;
(1-benzyl-1H-pyrazol-4-yl)(4-(6-isobutoxypyrimidin-4-yl)piperazin-1-yl)methanone;
(4-(6-isobutoxypyrimidin-4-yl)piperazin-1-yl)(3-(2-methoxyphenyl)-1H-pyrazol-5-yl)methanone;
(4-(6-isobutoxypyrimidin-4-yl)piperazin-1-yl)(5-methyl-2-phenyl-2H-1,2,3-triazol-4-yl)methanone;
(4-(6-isobutoxypyrimidin-4-yl)piperazin-1-yl)(1-(2-methoxyphenyl)-1H-pyrazol-4-yl)methanone;
(5-amino-1-phenyl-1H-pyrazol-4-yl)(4-(6-isobutoxypyrimidin-4-yl)piperazin-1-yl)methanone;
(4-(6-isobutoxypyrimidin-4-yl)piperazin-1-yl)(6-phenylpyrimidin-4-yl)methanone;
(4-(6-isobutoxypyrimidin-4-yl)piperazin-1-yl)(3-(2-methylthiazol-4-yl)phenyl)methanone;
(4-(6-isobutoxypyrimidin-4-yl)piperazin-1-yl)(1-methyl-3-(pyridin-3-yl)-1H-pyrazol-5-yl)methanone;
(4-(6-isobutoxypyrimidin-4-yl)piperazin-1-yl)(2-(pyridin-3-yl)thiazol-4-yl)methanone;
(4-(6-isobutoxypyrimidin-4-yl)piperazin-1-yl)(2-(pyridin-2-yl)thiazol-4-yl)methanone;
(4-(6-isopropoxypyrimidin-4-yl)piperazin-1-yl)(2-(pyridin-2-yl)thiazol-4-yl)methanone;
(1-(4-fluorophenyl)-5-methyl-1H-1,2,3-triazol-4-yl)(4-(6-isobutoxypyrimidin-4-yl)piperazin-1-yl)methanone;
(1-(4-fluorophenyl)-5-methyl-1H-1,2,3-triazol-4-yl)(4-(6-isopropoxypyrimidin-4-yl)piperazin-1-yl)methanone;
(4-(6-cyclobutoxypyrimidin-4-yl)piperazin-1-yl)(1-(4-fluorophenyl)-5-methyl-1H-1,2,3-triazol-4-yl)methanone;
(1-(4-fluorophenyl)-5-methyl-1H-1,2,3-triazol-4-yl)(4-(6-(2,2,2-trifluoroethoxy)pyrimidin-4-yl)piperazin-1-yl)methanone;
(4-(6-isobutoxypyrimidin-4-yl)piperazin-1-yl)(1-phenyl-1H-1,2,3-triazol-4-yl)methanone;
(4-(6-isobutoxypyrimidin-4-yl)piperazin-1-yl)(4-methyl-2-phenyloxazol-5-yl)methanone;
(5-fluoro-1-methyl-1H-indazol-3-yl)(4-(6-isobutoxypyrimidin-4-yl)piperazin-1-yl)methanone;
(5-fluoro-1-methyl-1H-indazol-3-yl)(4-(6-isopropoxypyrimidin-4-yl)piperazin-1-yl)methanone;

(5-fluoro-1-methyl-1H-indazol-3-yl)(4-(6-(2,2,2-trifluoroethoxy)pyrimidin-4-yl)piperazin-1-yl)methanone;
(4-(6-isobutoxypyrimidin-4-yl)piperazin-1-yl)(2-phenylthiazol-4-yl)methanone;
(6-(1H-pyrazol-1-yl)pyridin-3-yl)(4-(6-isobutoxypyrimidin-4-yl)piperazin-1-yl)methanone;
(4-(6-isobutoxypyrimidin-4-yl)piperazin-1-yl)(1-phenyl-1H-pyrazol-4-yl)methanone;
(1-ethyl-3-(trifluoromethyl)-1H-pyrazol-5-yl)(4-(6-isobutoxypyrimidin-4-yl)piperazin-1-yl)methanone;
(4-(6-cyclobutoxypyrimidin-4-yl)piperazin-1-yl)(5-methyl-1-phenyl-1H-1,2,3-triazol-4-yl)methanone;
2-(2H-benzo[d][1,2,3]triazol-2-yl)-1-(4-(6-cyclobutoxypyrimidin-4-yl)piperazin-1-yl)ethanone;
(1-ethyl-5-(trifluoromethyl)-1H-pyrazol-3-yl)(4-(6-isobutoxypyrimidin-4-yl)piperazin-1-yl)methanone;
(1-ethyl-5-(trifluoromethyl)-1H-pyrazol-3-yl)(4-(6-(2,2,2-trifluoroethoxy)pyrimidin-4-yl)piperazin-1-yl)methanone;
(6-ethoxypyridin-2-yl) (4-(6-isobutoxypyrimidin-4-yl)piperazin-1-yl)methanone;
(4-(6-isobutoxypyrimidin-4-yl)piperazin-1-yl)(6-(2,2,2-trifluoroethoxy)pyridin-2-yl)methanone;
(4-(6-isobutoxypyrimidin-4-yl)piperazin-1-yl)(2-isopropylthiazol-4-yl)methanone;
(4-(6-ethoxypyrimidin-4-yl)piperazin-1-yl)(2-(pyridin-2-yl)thiazol-4-yl)methanone;
(4-(6-(2,2,2-trifluoroethoxy)pyrimidin-4-yl)piperazin-1-yl)(1-(2-(trifluoromethyl)phen yl)-1H-imidazol-5-yl)methanone;
(2-(pyridin-2-yl)thiazol-4-yl)(4-(6-(2,2,2-trifluoroethoxy)pyrimidin-4-yl)piperazin-1-yl)methanone; and
(5-methyl-3-phenylisoxazol-4-yl)(4-(6-(2,2,2-trifluoroethoxy)pyrimidin-4-yl)piperazin-1-yl)methanone;
or a prodrug thereof or a pharmaceutically acceptable salt thereof.

Also, the present invention provides a pharmaceutical composition comprising a compound of formula (I) or a prodrug thereof or a pharmaceutically acceptable salt thereof, each as described herein, together with a pharmaceutically acceptable carrier for said compound.

Also, the present invention provides a pharmaceutical composition comprising a compound of formula (I) or a prodrug thereof or a pharmaceutically acceptable salt thereof, each as described herein, together with a pharmaceutically acceptable carrier for said compound and another pharmacologically active agent.

Also, the present invention provides a process for preparing a pharmaceutical composition, the process comprising mixing a compound of formula (I) or a prodrug thereof or a pharmaceutically acceptable salt thereof and a pharmaceutically acceptable carrier or excipient.

Further, the present invention provides a method for the treatment of a condition or disorder in which TTX-S channel blockers are involved, in an animal, including a human, which comprises administering to an animal in need of such treatment a therapeutically effective amount of a compound of formula (I) or a prodrug thereof or a pharmaceutically acceptable salt thereof, each as described herein.

The term "animal," as used herein, includes a mammalian subject or a non-mammalian subject. Examples of suitable mammalian subject may include, without limit, human, rodents, companion animals, livestock, and primates. Suitable rodents may include, but are not limited to, mice, rats, hamsters, gerbils, and guinea pigs. Suitable companion animals may include, but are not limited to, cats, dogs, rabbits, and ferrets. Suitable livestock may include, but are not limited to, horses, goats, sheep, swine, cattle, llamas, and alpacas. Suitable primates may include, but are not limited to, chimpanzees, lemurs, macaques, marmosets, spider monkeys, squirrel monkeys, and vervet monkeys. Examples of suitable non-mammalian subject may include, without limit, birds, reptiles, amphibians, and fish. Non-limiting examples of birds include chickens, turkeys, ducks, and geese.

In a further aspect, the present invention provides a process for preparing a pharmaceutical composition, the process comprising mixing a compound of formula (I) or a pharmaceutically acceptable salt thereof and a pharmaceutically acceptable carrier or excipient.

Examples of conditions or disorders mediated by TTX-S channels blocking activity include, but are not limited to, TTX-S channels related diseases. The compounds of the present invention show the TTX-S channels blocking activity. The compounds of the present invention may show less toxicity, good absorption, distribution, good solubility, less protein binding affinity other than TTX-S channels, less drug-drug interaction, and good metabolic stability.

As appreciated by those of skill in the art, "halogen" or "halo" as used herein is intended to include fluoro, chloro, bromo and iodo. Similarly, $C_1$-$C_6$, as in $C_1$-$C_6$ alkyl is defined to identify the group as having 1, 2, 3, 4, 5 or 6 carbons in a linear or branched arrangement, such that $C_1$-$C_6$ alkyl specifically includes methyl, ethyl, n-propyl, iso-propyl, n-butyl, iso-butyl, tert-butyl, pentyl, and hexyl. Similarly, $C_{2-6}$ alkenyl is defined to identify the group as having 2, 3, 4, 5 or 6 carbons which incorporates at least one double bond, which may be in a E- or a Z-arrangement. A group which is designated as being independently substituted with substituents may be independently substituted with multiple numbers of such substituents.

The term "$C_1$-$C_6$ haloalkyl", as used herein, means the group as having 1, 2, 3, 4, 5 or 6 carbons which incorporates at least one halogen atom, but not limited to monofluoromethyl, difluoromethyl, trifluoromethyl, 2,2,2-trifluoroethyl, 2,2-difluoroethyl, trichloromethyl, monochloromethyl, 1,2-dibromoethyl, monoiodopropyl, and 1,2-dibromohexyl.

The term "$C_1$-$C_6$ haloalkoxy", as used herein, means the group as having 1, 2, 3, 4, 5 or 6 carbons which incorporates at least one halogen atom, but not limited to monofluoromethoxy, difluoromethoxy, trifluoromethoxy, 2,2,2-trifluoroethoxy, 2,2-difluoroethoxy, trichloromethoxy, monochloromethoxy, and 1,2-dibromoethoxy.

The term "alkenyl", as used herein, means a hydrocarbon radical having at least one double bond including, but not limited to, ethenyl, propenyl, 1-butenyl, 2-butenyl and the like.

The term "cycloalkyl", as used herein, means a mono- or bicyclic ring, but not limited to, cyclopropyl, cyclobutyl, cyclopentyl, cyclohexyl, cycloheptyl, norboranyl, and adamantyl groups and the like.

The term "aryl", as used herein, means mono- or bi-carbocyclic or mono- or bi-heterocyclic group which may contain 0-4 heteroatoms selected from O, N and S, but not limited to, phenyl, naphthyl, benzoimidazolyl, benzimidazolonyl, benzofuranyl, benzofurazanyl, benzoisothiazolyl, 2,3-dihydrobenzofuranyl, benzopyrazolyl, benzotriazolyl, benzothiazolyl, benzothiadiazolyl, benzothiophenyl, benzoxazolyl, benzoisoxazolyl, carbazolyl, carbolinyl, chromanyl, cinnolinyl, 3,4-dihydro-2H-pyridoxazinyl, dioxoindolyl, furanyl, furazanyl, furopyridyl, furopyrrolyl, imidazolyl, imidazopyridinyl, imidazopyrazinyl, imidazopyrimidinyl, imidazothiazolyl, indazolyl, indolinyl, indolyl, indolazinyl, isobenzofuranyl, isochromanyl, isoindolyl, 1-oxo-isoindolyl, isoquinolyl, isothiazolyl, isoxazolopyridyl, isoxazolyl, isoxazolinyl, naphthpyridinyl, oxadiazolyl, oxazolyl, oxazolinyl, oxetanyl, 4-oxo-1,4-dihydroquinolyl, 2-oxo-1,2-dihydroquinolyl, 1-oxo-3,4-dihydroisoquinolinyl, 2-oxo-1,2,3,4-tetrahydroquinolyl, 2-oxo-2,5,6,7-tetrahydro-1H-cyclopentapyridyl, 2-oxo-2,3-dihydro-1H-benzoimidazolyl, oxoindolinyl, pyrazinyl, pyrazolopyridyl, pyrazolopyrimidyl, pyrazolyl, pyridazinyl, pyridopyridinyl, pyridazinyl, pyridyl, pyrimidinyl, pyrrolopyridyl, pyrrolyl, quinazolinyl, quinolyl, quinoxalinyl, tetrazolyl, tetrazolopyridyl, thiadiazolyl, thiazolyl, thienopyridyl, thienopyrrolyl, thienopyrazolyl, thienopyrazyl, thienyl, triazolyl, triazolopyrimidyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof and S-oxides thereof and the said rings which are fully or partially saturated and the like.

The term "heterocyclic group" as used herein includes both unsaturated and saturated heterocyclic moieties, wherein the unsaturated heterocyclic moieties include benzoimidazolyl, benzimidazolonyl, benzofuranyl, benzofurazanyl, benzoisoxazolyl, benzofuranyl, benzopyrazolyl, benzotriazolyl, benzothiazolyl, benzothiophenyl, benzoxazolyl, benzoisoxazolyl, carbazolyl, carbolinyl, cinnolinyl, chromanyl, furanyl, furazanyl, furopyridyl, furopyrrolyl, imidazolyl, imidazopyridinyl, imidazopyrazinyl, imidazopyrimidinyl, imidazothiazolyl, indazolyl, indolinyl, indolyl, indolazinyl, isobenzofuranyl, isochromanyl, isoindolyl, isoquinolyl, isothiazolyl, isoxazolyl, isoxazolinyl, isoxazolopyridyl, naphthpyridinyl, oxadiazolyl, oxazolyl, oxazolinyl, oxetanyl, oxoindolinyl, pyrazinyl, pyrazolyl, pyrazolopyridyl, pyrazolopyrimidyl, pyridazinyl, pyridopyridinyl, pyridazinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, thienopyrrolyl, thienopyrazolyl, thienopyrazyl, thienopyridyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, triazolopyrimidyl, tetrahydrothienyl, 3,4-dihydro-2H-pyridoxazinyl, 4-oxo-1,4-dihydroquinolyl, 2-oxo-1,2-dihydroquinolyl, 2-oxo-1,2,3,4-tetrahydroquinolyl, 2-oxo-2,5,6,7-tetrahydro-1H-cyclopentapyridyl, and 2-oxo-2,3-dihydro-1H-benzoimidazolyl, and N-oxides thereof and S-oxides thereof.

The term "$C_0$", as used herein, means direct bond.

The term "—$O_{0-1}$—", as used herein, means direct bond or —O—.

The term "treating" and "treatment", as used herein, refers to curative, palliative and prophylactic treatment, including reversing, alleviating, inhibiting the progress of, or preventing the disorder or condition to which such term applies, or one or more symptoms of such disorder or condition.

As used herein, the article "a" or "an" refers to both the singular and plural form of the object to which it refers unless indicated otherwise.

Included within the scope of the "compounds of the invention" are all salts, solvates, hydrates, complexes, polymorphs, prodrugs, radiolabeled derivatives, stereoisomers and optical isomers of the compounds of formula (I).

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci, 1977, 66, 1-19, such as acid addition salts formed with inorganic acids e.g. hydrochloric, hydrobromic, sulfuric, nitric or phosphoric acid; and organic acids e.g. succinic, maleic, formic, acetic, trifluoroacetic, propionic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms. In addition, certain compounds containing an acidic function such as a carboxy can be isolated in the form of their inorganic salt in which the counter ion can be selected from sodium, potassium, lithium, calcium, magnesium and the like, as well as from organic bases.

Also within the scope of the invention are so-called "prodrugs" of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T Higuchi and W Stella) and Bioreversible Carriers in Drug Design, Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in Design of Prodrugs by H Bundgaard (Elsevier, 1985). Some examples of prodrugs in accordance with the invention include:

(i) where the compound of formula (I) contains an alcohol functionality (—OH), compounds wherein the hydroxy group is replaced with a moiety convertible in vivo into the hydroxy group. Said moiety convertible in vivo into the hydroxy group means a moiety transformable in vivo into a hydroxyl group by e.g. hydrolysis and/or by an enzyme, e.g. an esterase. Examples of said moiety include, but are not limited to, ester and ether groups which may be hydrolyzed easily in vivo. Preferred are the moieties which are replaced the hydrogen of hydroxy group with acyloxyalkyl, 1-(alkoxycarbonyloxy)alkyl, phthalidyl and acyloxyalkyloxycarbonyl such as pivaloyloxymethyloxycarbonyl.

(ii) where the compound of the formula (I) contains an amino group, an amide derivative prepared by reacting with a suitable acid halide or a suitable acid anhydride is exemplified as a prodrug. A particularly preferred amide derivative as a prodrug is —NHCO(CH$_2$)$_2$OCH$_3$, —NHCOCH(NH$_2$)CH$_3$ or the like.

Further examples of replacement groups in accordance with the foregoing examples and examples of other prodrug types may be found in the aforementioned references.

The compounds of formula (I) and salts thereof may be prepared in crystalline or non-crystalline form, and, if crystalline, may optionally be hydrated or solvated. This invention includes within its scope stoichiometric hydrates or solvates as well as compounds containing variable amounts of water and/or solvent.

Salts and solvates having non-pharmaceutically acceptable counter-ions or associated solvents are within the scope of the present invention, for example, for use as intermediates in the preparation of other compounds of formula (I) and their pharmaceutically acceptable salts.

The compounds of formula (I) may have polymorphs in crystalline form, which are within the scope of the present invention.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

In certain of the compounds of formula (I), there may be some chiral carbon atoms. In such cases, compounds of formula (I) exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

The invention also includes isotopically-labeled compounds, which are identical to those described herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^2H$, $^3H$, $^{11}C$, $^{13}C$, $^{14}C$, $^{18}F$, $^{123}I$ and $^{125}I$. Compounds of the invention that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{123}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances, Isotopically labeled compounds of the invention can generally be prepared by carrying out the procedures disclosed in the Schemes and/or in the Examples below, then substituting a readily available isotopically labeled reagent for a non-isotopically labeled reagent.

With respect to other compounds disclosed in the art, the present compounds exhibit unexpected properties, such as with respect to duration of action and/or metabolism, such as increased metabolic stability, enhanced oral bioavailability or absorption, and/or decreased drug-drug interactions.

The compounds of formula (I), being $Na_{V1.3}$ channel blockers, are potentially useful in the treatment of a range of disorders. The treatment of pain, particularly chronic, inflammatory, neuropathic, nociceptive and visceral pain, is a preferred use.

Physiological pain is an important protective mechanism designed to warn of danger from potentially injurious stimuli from the external environment. The system operates through a specific set of primary sensory neurons and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually in twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardial infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and
orofacial pain, including dental pain, otic pain, burning mouth syndrome and temporomandibular myofascial pain.

The acyl piperazine derivatives of formula (I) are also expected to be useful in the treatment of multiple sclerosis.

The invention also relates to therapeutic use of the acyl piperazine derivatives of formula (I) as agents for treating or relieving the symptoms of neurodegenerative disorders. Such neurodegenerative disorders include, for example, Alzheimer's disease, Huntington's disease, Parkinson's disease, and Amyotrophic Lateral Sclerosis. The present invention also covers treating neurodegenerative disorders termed acute brain injury. These include but are not limited to: stroke, head trauma, and asphyxia. Stroke refers to a cerebral vascular disease and may also be referred to as a cerebral vascular accident (CVA) and includes acute thromboembolic stroke. Stroke includes both focal and global ischemia. Also, included are transient cerebral ischemic attacks and other cerebral vascular problems accompanied by cerebral ischemia. These vascular disorders may occur in a patient undergoing carotid endarterectomy specifically or other cerebrovascular or vascular surgical procedures in general, or diagnostic vascular procedures including cerebral angiography and the like. Other incidents are head trauma, spinal cord trauma, or injury from general anoxia, hypoxia, hypoglycemia, hypotension as well as similar injuries seen during procedures from embole, hyperfusion, and hypoxia. The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

TTX-S sodium channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with TTX-S sodium channels, including one or more of the following conditions or diseases: pain, acute pain, chronic pain, neuropathic pain, inflammatory pain, visceral pain, nociceptive pain, multiple sclerosis, neurodegenerative disorder, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, Crohn's disease, epilepsy or epileptic conditions, bipolar depression, tachyarrhythmias, mood disorder, bipolar disorder, psychiatric disorders such as anxiety and depression, myotonia, arrhythmia, movement disorders, neuroendocrine disorders, ataxia, incontinence, visceral pain, trigeminal neuralgia, herpetic neuralgia, general neuralgia, postherpetic neuralgia, radicular pain, sciatica, back pain, head or neck pain, severe or intractable pain, breakthrough pain, postsurgical pain, stroke, cancer pain, seizure disorder and causalgia.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy.

The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize.

For administration to human patients, the total daily dose of the compounds of the invention is typically in the range 0.1 mg to 1000 mg depending, of course, on the mode of administration. For example, oral administration may require a total daily dose of from 1 mg to 1000 mg, while an intravenous dose may only require from 0.1 mg to 100 mg. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

For the avoidance of doubt, references herein to "treatment" include references to curative, palliative and prophylactic treatment.

In one embodiment, the dosage range will be about 0.5 mg to 500 mg per patient per day; in another embodiment about 0.5 mg to 200 mg per patient per day; in another embodiment about 1 mg to 100 mg per patient per day; and in another embodiment about 5 mg to 50 mg per patient per day; in yet another embodiment about 1 mg to 30 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is envisioned. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is envisioned. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, including about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

A TTX-S sodium channels blocker may be usefully combined with another pharmacologically active compound, or with two or more other pharmacologically active compounds, particularly in the treatment of inflammatory, pain and urological diseases or disorders. For example, a TTX-S sodium channels blocker, particularly a compound of formula (I), or a prodrug thereof or a pharmaceutically acceptable salt or solvate thereof, as defined above, may be administered simultaneously, sequentially or separately in combination with one or more agents selected from an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an H1 antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex(registered trademark), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g. oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion (registered trademark) or sarizotan;

a vanilloid receptor agonist (e.g. resinferatoxin) or antagonist (e.g. capsazepine);

a transient receptor potential cation channel subtype (V1, V2, V3, V4, M8, A1) agonists and antagonists;

a beta-adrenergic such as propranolol;

a local anaesthetic such as mexiletine;

a corticosteroid such as dexamethasone;

a 5-HT receptor agonist or antagonist, particularly a 5-HT1B/1D agonist such as eletriptan, sumatriptan, naratriptan, zolmitriptan or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol (registered trademark);

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5- acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1alpha,3alpha,5alpha)(3-aminomethyl-bicyclo[3.2.0]hept-3-yl)-acetic acid, (3S,5R)-3aminomethyl-5 methyl-heptanoic acid, (3S,5R)-3 amino-5 methyl-heptanoic acid, (3S,5R)-3 amino-5 methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3aminomethyl-5 methyl-octanoic acid, (3S,5R)-3 amino-5 methyl-nonanoic acid, (3S,5R)-3 amino-5 methyl-octanoic acid, (3R,4R,5R)-3-amino-4,5-dimethyl-heptanoic acid and (3R,4R,5R)-3-amino-4,5-dimethyl-octanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, bupropion, buproprion metabolite hydroxybuproprion, nomifensine and viloxazine (Vivalan (registered trademark)), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-car bonyl]-4-methylbenzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-meth yl-2-quinolone (ZD-2138), or 2,3,5-trimethyl-6-(3-pyridylmethyl), 1,4-benzoquinone (CV-6504);

a sodium channel blocker, such as lidocaine;

a 5-HT3 antagonist, such as ondansetron;

a chemotherapy drug such as oxaliplatin, 5-fluorouracil, leukovolin, paclitaxel;

a calcitonin gene related peptide (CGRP) antagonist;

a bradykinin (BK1 and BK2) antagonists;

a voltage-gated sodium-dependent channel blockers ($Na_{v1.3}$, $Na_{v1.7}$, $Na_{v1.8}$);

a voltage dependent calcium channel blockers (N-type, T-type);

a P2X (ion channel type ATP receptor) antagonists;

an acid-sensing ion channel (ASIC1a, ASIC3) antagonists; and the pharmaceutically acceptable salts and solvates thereof.

Such combinations offer significant advantages, including synergistic activity, in therapy.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrate compositions are generally preferred. Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound or pharmaceutically acceptable salt thereof.

For parenteral administration, fluid unit dosage forms are prepared utilising a compound of formula (I) or pharmaceutically acceptable salt thereof and a sterile vehicle. Formulations for injection may be presented in unit dosage form e.g. in ampoules or in multi-dose, utilising a compound of formula (I) or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of formula (I) or pharmaceutically acceptable salts thereof may also be formulated in rectal compositions such as suppositories or retention enemas, e.g. containing conventional suppository bases such as cocoa butter or other glycerides.

The compounds of formula (I) or pharmaceutically acceptable salts may also be formulated as depot preparations. Such long acting formulations may be administered by implantation (for example subcutaneously or intramuscularly) or by intramuscular injection. Thus, for example, the compounds of formula (I) or pharmaceutically acceptable salts may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of formula (I) or pharmaceutically acceptable salts thereof may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, topical (including ophthalmic and nasal), depot or rectal administration or in a form suitable for administration by inhalation or insufflation (either through the mouth or nose). The compounds of formula (I) and pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

General Synthesis

Throughout the instant application, the following abbreviations are used with the following meanings:

DMF N,N-dimethylformamide
DMSO dimethyl sulfoxide
EDC 1-ethyl-3-(3-dimethylaminopropyl)carbodiimide hydrochloride
EtOAc ethyl acetate
HBTU O-(benzotriazol-1-yl)-N,N,N',N'-tetramethyluronium Hexafluorophosphate HOBT 1-hydroxybenztriazole
HPLC high pressure liquid chromatography
LC liquid chromatography
LG leaving group
NMR nuclear magnetic resonance
rt room temperature
THF tetrahydrofuran
TLC thin layer chromatography
tR retention time The term of "base" is likewise no particular restriction on the nature of the bases used, and any base commonly used in reactions of this type may equally be used here. Examples of such bases include: alkali metal hydroxides, such as lithium hydroxide, sodium hydroxide, potassium hydroxide, and barium hydroxide; alkali metal hydrides, such as lithium hydride, sodium hydride, and potassium hydride; alkali metal alkoxides, such as sodium methoxide, sodium ethoxide, and potassium t-butoxide; alkali metal carbonates, such as lithium carbonate, sodium carbonate, potassium carbonate, and cesium carbonate; alkali metal hydrogencarbonates, such as lithium hydrogencarbonate, sodium hydrogencarbonate, and potassium hydrogencarbonate; amines, such as N-methylmorpholine, triethylamine, tripropylamine, tributylamine, diisopropylethylamine, N-methylpiperidine, pyridine, 4-pyrrolidinopyridine, picoline, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), lutidine, and colidine; alkali metal amides, such as lithium amide, sodium amide, potassium amide, lithium diisopropyl amide, potassium diisopropyl amide, sodium diisopropyl amide, lithium bis(trimethylsilyl)amide and potassium bis(trimethylsilyl)amide. Of these, triethylamine, diisopropylethylamine, DBU, DBN, DABCO, pyridine, lutidine, colidine, sodium carbonate, sodium hydrogencarbonate, sodium hydroxide, potassium carbonate, potassium hydrogencarbonate, potassium hydroxide, barium hydroxide, and cesium carbonate are preferred.

The reactions are normally and preferably effected in the presence of inert solvent. There is no particular restriction on the nature of the solvent to be employed, provided that it has no adverse effect on the reaction or the reagents involved and that it can dissolve reagents, at least to some extent. Examples of suitable solvents include, but not limited to: halogenated hydrocarbons, such as dichloromethane, chloroform, carbon tetrachloride, and dichloroethane; ethers, such as diethyl ether, diisopropyl ether, THF, dimethoxyethane, and dioxane; aromatic hydrocarbons, such as benzene, toluene and nitrobenzene; amides, such as, DMF, N,N-dimethylacetamide, and hexamethylphosphoric triamide; amines, such as N-methylmorpholine, triethylamine, tripropylamine, tributylamine, diisopropylethylamine, N-methylpiperidine, pyridine, 4-pyrrolidinopyridine, N,N-dimethylaniline, and N,N-diethylaniline; alcohols, such as methanol, ethanol, propanol, isopropanol, and butanol; nitriles, such as acetonitrile and benzonitrile; sulfoxides, such as DMSO and sulfolane; ketones, such as acetone and di-ethylketone. Of these solvents, DMF, DMSO, acetonitrile, dichloromethane, dichloroethane, chloroform, dioxane, dimethoxyethane and THF are preferred.

The invention is illustrated in the following non-limiting examples in which, unless stated otherwise: all reagents are commercially available, all operations were carried out at room or ambient temperature, that is, in the range of about 18-25° C.; evaporation of solvent was carried out using a rotary evaporator under reduced pressure with a bath temperature of up to about 60° C. reactions were monitored by TLC and reaction times are given for illustration only; the structure and purity of all isolated compounds were assured by at least one of the following techniques: tlc (Merck silica gel 60 $F_{254}$ precoated TLC plates or Merck $NH_2$ $F_{254}$ precoated HPTLC plates), mass spectrometry or NMR. Yields are given for illustrative purposes only. Flash column chromatography was carried out using Merck silica gel 60 (230-400 mesh ASTM) or Fuji Silysia Chromatorex (registered trademark)

DU3050 (Amino Type) or Biotage silica (KP-Sil) or Biotage amino bounded silica (KP-NH) or Wakogel C-300HGT. The purification of compounds using HPLC (preparative LC-MS) was performed by the following apparatus and conditions.

Apparatus; Waters MS-trigger AutoPurification™ system

Column; Waters XTerra C18, 19×50 mm, 5 mm particle

Condition A: Methanol or acetonitrile/0.01% (v/v) ammonia aqueous solution

Condition B: Methanol or acetonitrile/0.05% (v/v) formic acid aqueous solution

Low-resolution mass spectral data (ESI) were obtained by the following apparatus and conditions: Apparatus; Waters Alliance HPLC system on ZQ or ZMD mass spectrometer and UV detector. $^1$H-NMR data was determined at 270 MHz (JEOL JNM-LA 270) or 300 MHz (JEOL JNM-LA300) using deuterated chloroform (99.8% D) or DMSO (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br=broad, etc. Chemical symbols have their usual meanings; μm (micrometer(s)), μL (microliter(s)), μg (microgram(s)), M (mol(s) per liter), L (liter(s)), mL (milliliter(s)), g (gram(s)), mg (milligram(s)), mol (moles), mmol (millimoles).

Conditions for Determining HPLC Retention Time:

Method A

Apparatus: Waters Acquity Ultra Performance LC on TUV Detector and ZQ mass spectrometer Column: XTerra MS C18, 2.1×30 mm, 3.5 micrometer particle Column Temperature: 45° C.

Solvents:

A1: acetonitrile

B1: 5 mM ammonium acetate aqueous solution

| Time (min) | A1 (%) | B1 (%) |
|---|---|---|
| 0 | 4 | 96 |
| 2 | 96 | 4 |
| 4 | 96 | 4 | run time 4.0 min
flow 0.5 mL/min

Method B

Apparatus: Waters Acquity Ultra Performance LC on TUV Detector and ZQ mass spectrometer Column: Waters ACQUITY C18, 2.1×100 mm, 1.7 micrometer particle Column Temperature: 60° C.

Solvents:

A1: 10 mM ammonium acetate aqueous solution

B1: acetonitrile

| Time (min) | A1 (%) | B1 (%) |
|---|---|---|
| 0 | 95 | 5 |
| 0.1 | 95 | 5 |
| 1.8 | 5 | 95 |
| 2.3 | 95 | 5 | run time 3 min
flow 0.7 mL/min

All of the acyl piperazine derivatives of the formula (I) can be prepared by the procedures described in the general methods presented below or by the specific methods described in the Examples section and the Preparations section, or by routine modifications thereof. The present invention also encompasses any one or more of these processes for preparing the acyl piperazine derivatives of formula (I), in addition to any novel intermediates used therein.

In the following general methods, descriptors are as previously defined for acyl piperazine derivatives of the formula (I) unless otherwise stated.

<Scheme-A>

[Chem.2]

-continued

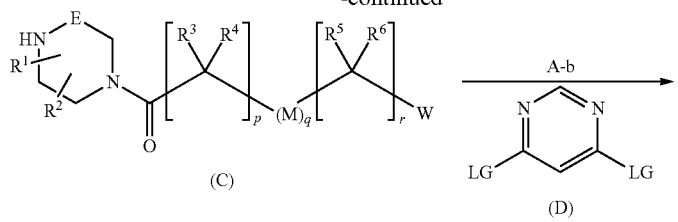

(C)     (D)

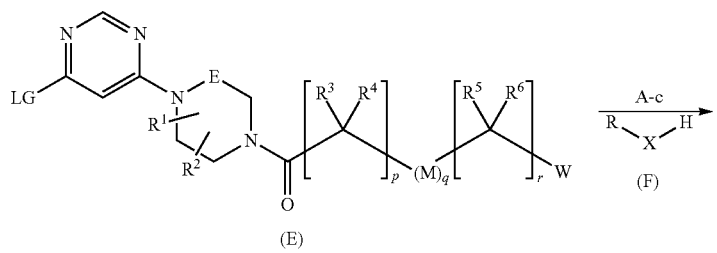

(E)     (F)

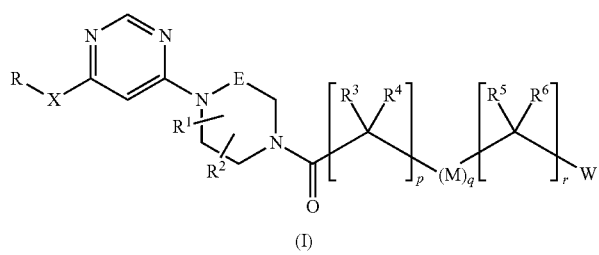

(I)

In Step A-a, a compound of formula (C) can be prepared from a compound of formula (B) by amidation with a compound of formula (A) with using a suitable condensation reagent such as HBTU or EDC-HOBT, preferably under the presence of a base such as triethylamine or diisopropylethylamine in a suitable solvent such as DMF, acetonitrile, or dichloromethane at a temperature of from about 5 to 60° C. for about 1-24 hours. In addition, a compound of formula (C) can be also prepared from a compound of formula (A) by amidation with an acid chloride prepared from a compound of formula (B) using thionyl chloride or oxalyl chloride, preferably under the presence of a base such as triethylamine, pyridine, or N,N-diisopropylethylamine in a suitable solvent such as dichloromethane at a temperature of from about 5 to 40° C. for about 1-24 hours. If necessary, a compound of formula (A) can be protected by suitable protective group such as Boc or Cbz group.

In Step A-b, a compound of formula (E) can be prepared from a compound of formula (D) by SNAr reaction with a compound of formula (C) using a suitable base such as potassium carbonate in a suitable solvent such as DMF or dioxane at a temperature of from about 0 to about 180° C. for about 1-24 hours. Alternatively, a compound of formula (E) can be prepared from a compound of formula (D) by coupling reaction with a compound of formula (C) using a suitable catalyst such as tris(dibenzylideneacetone)dipalladium, a suitable ligand such as Xantphos, a suitable base such as tripotassium phosphate, and a suitable solvent such as dioxane at a temperature of from about 50-250° C. for about 1-48 h.

In Step A-c, a compound of formula (I) can be prepared from a compound of formula (E) by SNAr reaction with a compound of formula (F) using a suitable base such as sodium hydride or potassium tert-butoxide in a suitable solvent such as DMF or THF at a temperature of from about −20 to about 150° C. for about 1-24 hours.

<Scheme-B>

[Chem.3]

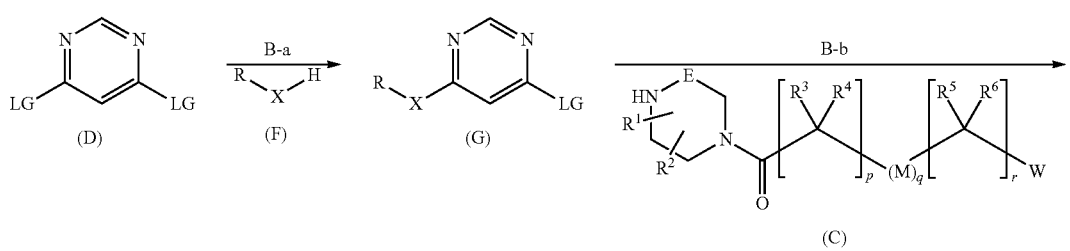

(D)     (F)     (G)     (C)

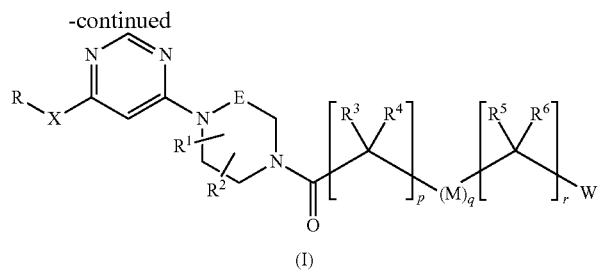

In Step B-a, a compound of formula (G) can be prepared from a compound of formula (D) by SNAr reaction with a compound of formula (F) using a suitable base such as sodium hydride or potassium tert-butoxide in a suitable solvent such as DMF or THF at a temperature of from about −20 to about 100° C. for about 1-24 hours.

In Step B-b, a compound of formula (I) can be prepared from a compound of formula (G) by SNAr reaction with a compound of formula (C) using a suitable base such as potassium carbonate in a suitable solvent such as DMF or dioxane at a temperature of from about 0 to about 180° C. for about 1-24 hours. Alternatively, a compound of formula (I) can be prepared from a compound of formula (G) by coupling reaction with a compound of formula (C) using a suitable catalyst such as tris(dibenzylideneacetone)dipalladium, a suitable ligand such as Xantphos, a suitable base such as tripotassium phosphate, and a suitable solvent such as dioxane at a temperature of from about 50-200° C. for about 1-48 h.

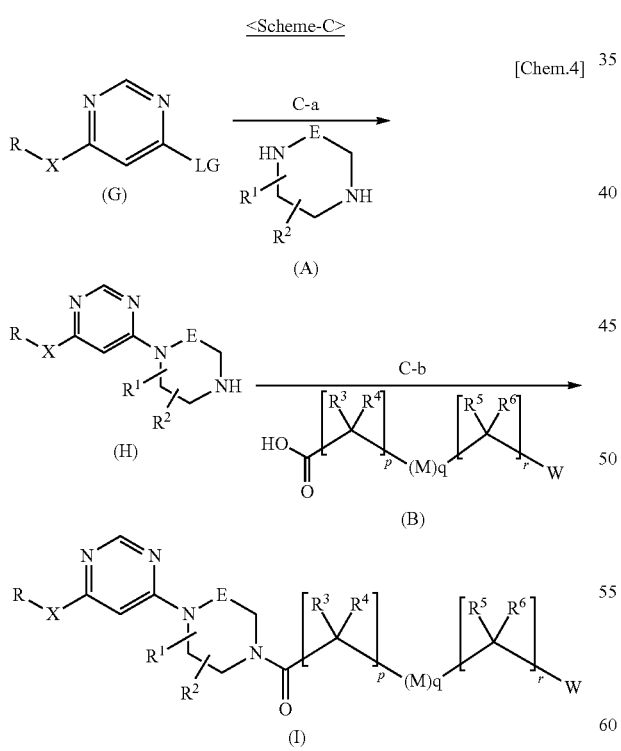

In Step C-a, a compound of formula (H) can be prepared from a compound of formula (G) by SNAr reaction with a compound of formula (A) using a suitable base such as potassium carbonate in a suitable solvent such as DMF or dioxane at a temperature of from about 0 to about 180° C. for about 1-24 hours. Alternatively, a compound of formula (H) can be prepared from a compound of formula (G) by coupling reaction with a compound of formula (A) using a suitable catalyst such as tris(dibenzylideneacetone)dipalladium, a suitable ligand such as Xantphos, a suitable base such as tripotassium phosphate, and a suitable solvent such as dioxane at a temperature of from about 50-200° C. for about 1-48 h. If necessary, a compound of formula (A) can be protected by suitable protective group such as Boc or Cbz group.

In Step C-b, a compound of formula (I) can be prepared from a compound of formula (B) by amidation with a compound of formula (H) with using a suitable condensation reagent such as HBTU or EDC-HOBT, preferably under the presence of a base such as triethylamine or diisopropylethylamine in a suitable solvent such as DMF at a temperature of from about 5 to about 60° C. for about 1-24 hours. In addition, a compound of formula (I) can be also prepared from a compound of formula (H) by amidation with an acid chloride prepared from a compound of formula (B) using thionyl chloride or oxalyl chloride, preferably under the presence of a base such as triethylamine, pyridine, or N,N-diisopropylethylamine in a suitable solvent such as dichloromethane at a temperature of from about 5 to 40° C. for about 1-24 hours.

In order to obtain some other compounds of formula (I), the appropriate conversion reaction of the substituents will be used.

All starting materials in the following general syntheses may be commercially available or obtained by conventional methods known to those skilled in the art, otherwise noted in the synthesis part.

Intermediate Synthesis Part

Intermediate-A:
4-cyclobutoxy-6-(piperazin-1-yl)pyrimidine dihydrochloride

Step-1: tert-butyl 4-(6-cyclobutoxypyrimidin-4-yl)piperazine-1-carboxylate

To a suspension of sodium hydride (60% in mineral oil, 469 mg, 11.7 mmol) in DMF (15 mL) was added cyclobutanol (0.92 ml, 11.7 mmol) at 0° C. After stirring at 0° C. for 30 min, a solution of tert-butyl 4-(6-chloropyrimidin-4-yl)piperazine-1-carboxylate (700 mg, 2.34 mmol) in DMF (0.5 mL) was slowly added, and the mixture was stirred at rt for 12 h. Then, the mixture was poured onto water, and the aqueous layer was extracted with EtOAc (twice). The combined organic layer was dried over sodium sulfate and concentrated in vacuo. The residue was purified by column chromatography on silica gel eluting with hexane/EtOAc (5:1-3:1) to give 687 mg (88% yield) of the title compound as a white solid.

$^1$H-NMR (300 MHz, CDCl$_3$) δ=8.29 (1H, s), 5.77 (1H, s), 5.16 (1H, q, J=9.7 Hz), 3.58-3.50 (8H, m), 2.44-2.39 (2H, m), 2.16-2.09 (2H, m), 1.84-1.64 (2H, m), 1.48 (9H, s), LCMS (Method A) m/z: M+1 obs 335.2, $t_R$=3.25 min.

Step-2: 4-cyclobutoxy-6-(piperazin-1-yl)pyrimidine dihydrochloride

A mixture of tert-butyl 4-(6-cyclobutoxypyrimidin-4-yl)piperazine-1-carboxylate (687 mg, 2.06 mmol) and 4 M HCl-EtOAc (30 ml) were stirred at rt for 2 h. Then EtOAc was added, and the solvent was removed in vacuo. The residue was suspended in EtOAc, and the white precipitate was collected by filtration to give 525 mg (quant) of the title compound as a white solid. The compound was used for the next step without further purification.
$^1$H-NMR (300 MHz, DMSO-$d_6$) δ=9.21 (2H, brs), 8.29 (1H, s), 6.17 (1H, s), 5.10 (1H, q, J=9.8 Hz), 3.81 (4H, t, J=5.9), 3.12 (4H, s), 2.33-2.41 (2H, m), 1.98-2.05 (2H, m), 1.58-1.77 (2H, m) (a signal due to NH was not observed), LCMS (Method A) m/z: M+1 obs 235.3, $t_R$=2.07 min.

Intermediate B:
4-isobutoxy-6-(piperazin-1-yl)pyrimidine dihydrochloride

Step-1: tert-butyl 4-(6-isobutoxypyrimidin-4-yl)piperazine-1-carboxylate

The title compound was prepared according to the procedure described in Step-1 of Intermediate A using 2-methyl-propan-1-ol.
$^1$H-NMR (300 MHz, CDCl$_3$) δ 8.31 (1H, s), 5.82 (1H, s), 4.05 (2H, d, J=6.6 Hz), 3.62-3.48 (8H, m), 2.12-1.98 (1H, m), 1.48 (9H, s), 0.99 (6H, d, J=6.6 Hz), LCMS (Method A) m/z: M+1 obs 337.2, $t_R$=3.32 min.

Step-2: 4-isobutoxy-6-(piperazin-1-yl)pyrimidine dihydrochloride

The title compound was prepared according to the procedure described in Step-2 of Example 1 using tert-butyl 4-(6-isobutoxypyrimidin-4-yl)piperazine-1-carboxylate.
$^1$H-NMR (300 MHz, DMSO-$d_6$) δ 9.37 (2H, br), 8.34 (1H, s), 6.28 (1H, s), 4.05 (2H, d, J=6.6 Hz), 3.89-3.82 (4H, m), 3.18-3.09 (4H, m), 2.08-1.94 (1H, m), 0.95 (6H, d, J=6.6 Hz) (a signal due to NH was not observed), LCMS (Method A) m/z: M+1 obs 237.4, $t_R$=2.25 min.

Intermediate C: 4-(piperazin-1-yl)-6-(2.2.2-trifluoroethoxy)pyrimidine dihydrochloride Step-1: tert-butyl 4-(6-(2,2,2-trifluoroethoxy)pyrimidin-4-yl)piperazine-1-carboxylate A mixture of 4-chloro-6-(2,2,2-trifluoroethoxy)pyrimidine (2.19 g, 10.3 mmol), tert-butyl piperazine-1-carboxylate (2.30 g, 12.4 mmol), and potassium carbonate (2.85 g, 20.6 mmol) in DMF was stirred at 100° C. for 1 h. After cooling to rt, the mixture was poured onto water (100 mL), and the aqueous layer was extracted with EtOAc (twice).
The combined organic layers were dried over sodium sulfate and concentrated in vacuo. The residue was purified by column chromatography on silica gel eluting with hexane/EtOAc (5:1-3:1) to give 3.37 g (90% yield) of the title compound as a white solid.
$^1$H-NMR (300 MHz, CDCl$_3$) δ 8.29 (1H, s), 5.93 (1H, s), 4.75 (2H, q, J=8.1 Hz), 3.64-3.58 (4H, m), 3.55-3.49 (4H, m), 1.49 (9H, s), LCMS (Method A) m/z: M+1 obs 363.2, $t_R$=3.29 min.

Step-2: 4-(piperazin-1-yl)-6-(2,2,2-trifluoroethoxy)pyrimidine dihydrochloride

The title compound was prepared according to the procedure described in Step-2 of Example 1 using tert-butyl 4-(6-(2,2,2-trifluoroethoxy)pyrimidin-4-yl)piperazine-1-carboxylate.
$^1$H-NMR (300 MHz, DMSO-$d_6$) δ 9.5-9.2 (2H, br), 8.36 (1H, s), 6.42 (1H, s), 5.01 (2H, q, J=8.8 Hz), 3.9-3.7 (4H, m), 3.2-3.05 (4H, m) (a signal due to NH was not observed), LCMS (Method A) m/z: M+1 obs 263.2, $t_R$=2.12 min.

Intermediate D:
4-isopropoxy-6-(piperazin-1-yl)pyrimidine dihydrochloride

Step-1: tert-butyl 4-(6-isopropoxypyrimidin-4-yl)piperazine-1-carboxylate

The title compound was prepared according to the procedure described in Step-1 of Intermediate A using propan-2-ol.
$^1$H-NMR (300 MHz, CDCl$_3$) δ 8.30 (1H, s), 5.77 (1H, s), 5.35-5.27 (1H, m), 3.57-3.50 (8H, m), 1.48 (9H, s), 1.32 (6H, d, J=5.9 Hz), LCMS (Method A) m/z: M+1 obs 323.4, $t_R$=3.18 min.

Step-2: 4-isopropoxy-6-(piperazin-1-yl)pyrimidine dihydrochloride

The title compound was prepared according to the procedure described in Step-2 of Example 1 using tert-butyl 4-(6-isopropoxypyrimidin-4-yl)piperazine-1-carboxylate.
$^1$H-NMR (300 MHz, DMSO-$d_6$) δ 9.67 (2H, brs), 8.40 (1H, s), 6.34 (1H, s), 5.26-5.21 (1H, m), 3.96 (4H, brs), 3.15 (4H, brs), 1.31 (6H, d, J=5.9 Hz) (a signal due to NH was not observed), LCMS (Method A) m/z: M+1 obs 223.4, $t_R$=2.47 min.

Intermediate E: (1S,4S)-2-(6-isobutoxypyrimidin-4-yl)-2,5-diazabicyclo[2.2.1]heptane dihydrochloride Step-1: tert-butyl (1S,4S)-5-(6-isobutoxypyrimidin-4-yl)-2,5-diazabicyclo[2.2.1]heptane-2-carboxylate The title compound was prepared according to the procedure described in Step-1 of Intermediate C using tert-butyl (1S,4S)-2,5-diazabicyclo[2.2.1]heptane-2-carboxylate and 4-chloro-6-isobutoxypyrimidine.
$^1$H-NMR (300 MHz, CDCl$_3$) δ 8.27 (1H, s), 5.56 (1H, s), 4.68 & 4.54 (1H, s), 4.04 (2H, d, J=6.6 Hz), 3.43-3.35 (5H, m), 2.05 (1H, m), 1.91 (2H, s), 1.47 & 1.43 (9H, s), 0.99 (6H, d, J=6.6 Hz), LCMS (Method A) m/z: M+1 obs 349.3, $t_R$=3.21 min.

Step-2: (1S,4S)-2-(6-isobutoxypyrimidin-4-yl)-2,5-diazabicyclo[2.2.1]heptane dihydrochloride The title compound was prepared according to the procedure described in Step-2 of Example 1 using tert-butyl (1S,4S)-5-(6-isobutoxypyrimidin-4-yl)-2,5-diazabicyclo[2.2.1]heptane-2-carboxylate.

¹H-NMR (300 MHz, DMSO-d₆) δ 9.81 (1H, brs), 9.34 (1H, brs), 8.36 (1H, s), 6.08 (1H, brs), 5.03 (1H, brs), 4.51 (1H, s), 4.07 (2H, d, J=6.6 Hz), 3.27-3.18 (2H, m), 2.12-1.91 (3H, m), 0.96 (6H, d, J=6.6 Hz) (signals due to NH and 2×CH was not observed), LCMS (Method A) m/z: M+1 obs 249.4, $t_R$=2.71 min.

Intermediate F: (4-(6-chloropyrimidin-4-yl)piperazin-1-yl)(3-fluoro-4-methylphenyl)methanone Step-1: tert-butyl 4-(3-fluoro-4-methylbenzoyl)piperazine-1-carboxylate To a mixture of tert-butyl piperazine-1-carboxylate (1.81 g, 9.7 mmol), 3-fluoro-4-methylbenzoic acid (1.50 g, 9.7 mmol), and triethylamine (6.8 mL, 49 mmol) in acetonitrile (30 mL), HBTU (4.06 g, 10.7 mmol) was added. After stirring at rt for 1 h, the mixture was poured onto water (150 mL), and the mixture was extracted with EtOAc (twice). The combined organic layers were dried over sodium sulfate and concentrated in vacuo. The residue was purified by column chromatography on silica gel eluting with hexane/EtOAc (4:1-2:1) to give 3.14 g (quant) of the title compound as a white solid.
¹H-NMR (300 MHz, CDCl₃) δ 7.26-7.20 (1H, m), 7.09-7.03 (2H, m), 3.7-3.3 (8H, m), 2.30 (3H, s), 1.47 (9H, s), LCMS (Method A) m/z: M+1 obs 323.3, $t_R$=3.05 min.

Step-2: (3-fluoro-4-methylphenyl)(piperazin-1-yl)methanone hydrochloride

A mixture of tert-butyl 4-(3-fluoro-4-methylbenzoyl)piperazine-1-carboxylate (3.14 g, 9.74 mmol) and 4 M HCl-EtOAc was stirred at rt for 20 h. After removing the solvent, the residue was suspended in EtOAc, and the white precipitate was collected by filtration to give 1.97 g (78% yields) of the title compound as a white solid.
¹H-NMR (300 MHz, DMSO-d₆) δ 9.0 (2H, br), 7.41 (1H, t, J=8.1 Hz), 7.32-7.20 (2H, m), 3.8-3.1 (8H, m), 2.30 (3H, s), LCMS (Method A) m/z: M+1 obs 223.3, $t_R$=0.99 min.

Step-3: (4-(6-chloropyrimidin-4-yl)piperazin-1-yl)(3-fluoro-4-methylphenyl)methanone A mixture of (3-fluoro-4-methylphenyl)(piperazin-1-yl)methanone hydrochloride (434 mg, 1.67 mmol), 4,6-dichloropyrimidine (250 mg, 1.67 mmol), and triethylamine (0.94 mL, 6.71 mmol) in dioxane (10 mL) was refluxed with stirring for 4 h. After cooling to rt, the mixture was poured onto water, and the aqueous phase was extracted with EtOAc (twice). The combined organic layers were dried over sodium sulfate and concentrated in vacuo. The residue was purified by column chromatography on silica gel eluting with hexane/EtOAc (5:1-2:1) to give 400 mg (71% yield) of the title compound as a white solid.
¹H-NMR (300 MHz, CDCl₃) δ 8.41 (1H, s), 7.29-7.23 (1H, m), 7.14-7.08 (2H, m), 6.53 (1H, s), 3.9-3.6 (8H, m), 2.33 (3H, s), LCMS (Method A) m/z: M+1 obs 335.2, $t_R$=2.84 min.

Intermediate G: 4-(3-fluoro-4-methylbenzoyl)piperazin-2-one

The title compound was prepared according to the procedure described in Step-1 of Intermediate F using piperazin-2-one and 3-fluoro-4-methylbenzoic acid.

¹H-NMR (300 MHz, CDCl₃) δ 7.28-7.21 (1H, m), 7.13-7.07 (2H, m), 6.41 (1H, br), 4.25 (2H, br), 3.85 (2H, br), 3.47 (2H, br), 2.31 (3H, s), LCMS (Method A) ink: M+1 obs 237.2, $t_R$=2.15 min.

Intermediate H: 2-(chroman-4-yloxy)acetic acid

Step-1: ethyl 2-(chroman-4-yloxy)acetate

To a suspension of sodium hydride (60% in mineral oil, 173 mg, 4.33 mmol) in THF was added chroman-4-ol (500 mg, 3.33 mmol) at 0° C. After being stirred at the same temperature for 15 min, ethyl bromoacetate (723 mg, 4.33 mmol) was added. After 1 h, the mixture was poured onto water, and the aqueous phase was extracted with EtOAc (twice). The combined organic layer was dried over sodium sulfate and concentrated in vacuo. The residue was purified by column chromatography on silica gel eluting with hexane/EtOAc (7:1-4:1) to give 404 mg (51% yield) of the title compound as a colorless oil.
¹H-NMR (270 MHz, CDCl₃) δ 7.34 (1H, d, J=7.2 Hz), 7.22 (1H, t, J=7.2 Hz), 6.90 (1H, t, J=7.2 Hz), 6.84 (1H, d, J=7.2 Hz), 4.58-4.53 (1H, m), 4.35-4.18 (6H, m), 2.22-1.98 (2H, m), 1.30 (3H, t, J=7.2 Hz), LCMS (Method A) ink: fragment peak obs 133.1, $t_R$=2.80 min.

Step-2: 2-(chroman-4-yloxy)acetic acid

A mixture of ethyl 2-(chroman-4-yloxy)acetate (403 mg, 1.71 mmol) and sodium hydroxide aqueous solution (2 M, 1.71 mL, 3.41 mmol) in methanol (10 mL) was stirred at rt for 3 h. Then, hydrochloric acid (2 M, 1.71 mL, 3.41 mmol) was added, and the solvent was removed in vacuo. The residue was suspended in THF, and the mixture was filtered through a pad of Celite. The filtrate was concentrated in vacuo to give 370 mg (quant) of the title compound as a colorless oil. This was used for the next step without further purification.
LCMS (Method A) m/z: M−1 obs 207.2, $t_R$=2.25 min.

Example Synthesis Part

Example 1

(3-fluoro-4-methylphenyl)(4-(6-isobutoxypyrimidin-4-yl)piperazin-1-yl)methanone

To a suspension of sodium hydride (60% in mineral oil, 20 mg, 0.52 mmol) in DMF was added 2-methylpropan-1-ol (39 mg, 0.52 mmol) at rt. After stirring at rt for 15 min, (4-(6-chloropyrimidin-4-yl)piperazin-1-yl)(3-fluoro-4-methylphenyl)methanone (35 mg, 0.11 mmol) was added to the mixture. After stirring at rt for 12 h, the mixture was poured onto water (5 mL), and the aqueous phase was extracted with dichloromethane (three times). The combined organic layers were dried over sodium sulfate and concentrated in vacuo. The residue was purified by preparative LC-MS to give 14.4 mg (37% yields) of the title compound.

By a method similar to Example 1 except that the reactant is different, the following compounds of Examples 2, 6-8, 12, 16, and 241 were similarly prepared (also see Table 1). The reactants were used commercially available material or obtained by conventional methods known to those skilled in the art.

Example 3

(R)-2-hydroxy-1-(4-(6-isobutoxypyrimidin-4-yl) piperazin-1-yl)-2-phenylethanone

To a mixture of 4-isobutoxy-6-(piperazin-1-yl)pyrimidine dihydrochloride (30 mg, 0.097 mmol), (R)-2-hydroxy-2-phenylacetic acid (15 mg, 0.097 mmol), and triethylamine (0.07 mL, 0.49 mmol) in DMF was added HBTU (48 mg, 0.13 mmol), and the mixture was stirred at rt for 1 h. Then the mixture was poured onto water (3 mL), and the aqueous layer was extracted with dichloromethane (three times). The combined organic layers were dried over sodium sulfate and concentrated in vacuo. The residue was purified by preparative LC-MS to give 7.2 mg (15% yields) of the title compound.

By a method similar to Example 3 except that the reactant is different, the following compounds of Examples 4, 5, 9-11, 13-15, 18-52, 54-71, 77, 80-99, 101-126, 130-142, 146-148, 151-225, 227-240, and 242-246 were similarly prepared (also see Table 1). The reactants were commercially available material or obtained by conventional methods known to those skilled in the art, otherwise noted in the intermediate synthesis parts.

Example 17

4-(3-fluoro-4-methylbenzoyl)-1-(6-isobutoxypyrimidin-4-yl)piperazin-2-one

A mixture of 4-chloro-6-isobutoxypyrimidine (50 mg, 0.27 mmol), 4-(3-fluoro-4-methylbenzoyl)piperazin-2-one (76 mg, 0.32 mmol), tris(dibenzylideneacetone)dipalladium (12 mg, 0.013 mmol), Xantphos (23 mg, 0.040 mmol), and tripotassium phosphate (85 mg, 0.40 mmol) in dioxane (5 mL) was stirred at 100° C. for 12 h. After cooling to rt, the mixture was poured onto water, and the aqueous layer was extracted with dichloromethane (twice). The combined organic layer was dried over sodium sulfate and concentrated in vacuo. The residue was purified by preparative LC-MS to give 4.3 mg (4% yields) of the title compound.

Example 72

4-fluoro N (2 (4 (6 isobutoxypyrimidin-4-yl)piperazin-1-yl)-2-oxoethyl)benzamide

Step-1: tert-butyl (2-(4-(6-isobutoxypyrimidin-4-yl) piperazin-1-yl)-2-oxoethyl)carbamate The title compound was prepared according to the procedure described in Example 3 using 4-isobutoxy-6-(piperazin-1-yl)pyrimidine dihydrochloride and 2-((tert-butoxycarbonyl)amino)acetic acid.

$^1$H-NMR (300 MHz, CDCl$_3$) δ 8.32 (1H, s), 5.84 (1H, s), 5.50 (1H, brs), 4.06 (2H, d, J=6.6 Hz), 4.01 (2H, m), 3.75-3.68 (4H, m), 3.61-3.57 (2H, m), 3.51-3.47 (2H, m), 2.03 (1H, m), 1.46 (9H, s), 1.01 (6H, d, J=6.6 Hz), LCMS (Method A) m/z: M+1 obs 394.3, t$_R$=3.01 min.

Step-2: 2-amino-1-(4-(6-isobutoxypyrimidin-4-yl) piperazin-1-yl)ethanone dihydrochloride The title compound was prepared according to the procedure described in step-2 of Intermediate F using tert-butyl (2-(4-(6-isobutoxypyrimidin-4-yl)piperazin-1-yl)-2-oxoethyl) carbamate.

$^1$H-NMR (300 MHz, DMSO-d$_6$) δ 8.38 (1H, s), 8.24 (2H, brs), 6.31 (1H, s), 4.08 (2H, d, J=6.6 Hz), 3.93 (2H, m), 3.78-3.51 (8H, m), 2.05-2.00 (1H, m), 1.91 (2H, s), 0.97 (6H, d, J=6.6 Hz), LCMS (Method A) m/z: M+1 obs 294.4, t$_R$=2.37 min.

Step-3: 4-fluoro-N-(2-(4-(6-isobutoxypyrimidin-4-yl)piperazin-1-yl)-2-oxoethyl)benzamide The title compound was prepared according to the procedure described in Example 3 using 2-amino-1-(4-(6-isobutoxypyrimidin-4-yl)piperazin-1-yl)ethanone dihydrochloride and 4-fluorobenzoic acid.

By a method similar to Example 72 except that the reactant is different, the following compounds of Examples 73-76 were similarly prepared (also see Table 1). The reactants were commercially available material or obtained by conventional methods known to those skilled in the art.

Example 78

1-(4-(6-isobutoxypyrimidin-4-yl)piperazin-1-yl)-2-(quinolin-5-yloxy)ethanone

Step-1: 2-chloro-1-(4-(6-isobutoxypyrimidin-4-yl) piperazin-1-yl)ethanone

To a mixture of 4-isobutoxy-6-(piperazin-1-yl)pyrimidine hydrochloride (300 mg, 0.97 mmol) and triethylamine (0.68 mL, 4.9 mmol) was added chloroacetyl chloride (121 mg, 1.07 mmol) at 0° C. After being stirred at the same temperature for 30 min, the mixture was poured onto water, and the aqueous layer was extracted with dichloromethane (twice). The combined organic layer was dried over sodium sulfate and concentrated in vacuo. The residue was purified by column chromatography on silica gel eluting with hexane/EtOAc (1.5:1-1:1) to give the title compound (262 mg, 86%) as a colorless oil.

$^1$H-NMR (300 MHz, CDCl$_3$) δ 8.32 (1H, s), 5.85 (1H, s), 4.12 (2H, s), 4.06 (2H, d, J=6.6 Hz), 3.78-3.56 (8H, m), 2.05 (1H, m), 1.00 (6H, d, J=6.6 Hz), LCMS (Method A) m/z: M+1 obs 313.3, t$_R$=2.80 min.

Step-2: 1-(4-(6-isobutoxypyrimidin-4-yl)piperazin-1-yl)-2-(quinolin-5-yloxy)ethanone A mixture of 2-chloro-1-(4-(6-isobutoxypyrimidin-4-yl) piperazin-1-yl)ethanone (20 mg, 0.064 mmol), quinolin-5-ol (10.2 mg, 0.070 mmol), and potassium carbonate (18 mg, 0.13 mmol) in DMF was (0.5 mL) was stirred at 90° C. for 3 h. After cooling to rt, the mixture was poured onto water, and the aqueous later was extracted with dichloromethane (three times). The combined organic layer was dried over sodium sulfate and concentrated in vacuo. The residue was purified by preparative LC-MS to give 9.3 mg (34% yields) of the title compound.

By a method similar to Example 78 except that the reactant is different, the following compounds of Examples 79, 100, 127-129, 143-145 were similarly prepared (also see Table 1). The reactants were commercially available material or obtained by conventional methods known to those skilled in the art.

Example 53 benzyl 4-(6-isobutoxypyrimidin-4-yl)piperazine-1-carboxylate

The title compound was prepared according to the procedure described in Step 1 of Example 78 using benzyl chloroformate.

Example 149

1-(benzo[d]oxazol-2-ylmethyl)-4-(6-isobutoxypyrimidin-4-yl)piperazin-2-one

Step-1: 4-(6-isobutoxypyrimidin-4-yl)piperazin-2-one

The title compound was prepared according to the procedure described in Step 1 of intermediate C using 4-chloro-6-isobutoxypyrimidine and piperazin-2-one.

$^1$H-NMR (300 MHz, CDCl$_3$) δ 8.33 (1H, s), 6.28 (1H, brs), 5.79 (1H, s), 4.12 (2H, s), 4.07 (2H, d, J=6.6 Hz), 3.96-3.93 (2H, m), 3.51-3.47 (2H, m), 2.11-2.02 (1H, m), 0.99 (6H, d, J=7.3 Hz), LCMS (Method A) m/z: M+1 obs 251.4, t$_R$=2.54 min.

Step-2: 1-(benzo[d]oxazol-2-ylmethyl)-4-(6-isobutoxypyrimidin-4-yl)piperazin-2-one To a suspension of sodium hydride (60% in mineral oil, 2.8 mg, 0.07 mmol) in DMF was added 4-(6-isobutoxypyrimidin-4-yl)piperazin-2-one (16 mg, 0.064 mmol). After 5 min, 2-(chloromethyl)benzo[d]oxazole (10.7 mg, 0.064 mmol) was added, and the mixture was stirred at rt for 30 min. The mixture was quenched with water, extracted with EtOAc (twice). The combined organic layer was dried over sodium sulfate and concentrated in vacuo. The residue was purified by preparative LC-MS to give 9.3 mg (38% yields) of the title compound.

By a method similar to Example 149 except that the reactant is different, the following compound of Example 150 was similarly prepared (also see Table 1). The reactants were commercially available material or obtained by conventional methods known to those skilled in the art.

Example 226

(4-(6-isobutoxypyrimidin-4-yl)piperazin-1-yl)(5-(6-methoxypyridin-3-yl)-1-methyl-1H-pyrazol-3-yl)methanone

Step-1: (5-iodo-1-methyl-1H-pyrazol-3-yl)(4-(6-isobutoxypyrimidin-4-yl)piperazin-1-yl)methanone The title compound was prepared according to the procedure described in Example 3 using 4-isobutoxy-6-(piperazin-1-yl)pyrimidine hydrochloride and 5-iodo-1-methyl-1H-pyrazole-3-carboxylic acid.

$^1$H-NMR (300 MHz, CDCl$_3$) δ 8.32 (1H, s), 6.87 (1H, s), 5.84 (1H, s), 4.06 (2H, d, J=6.6 Hz), 4.05 (2H, br), 3.97 (3H, s), 3.85 (2H, brs), 3.69-3.66 (4H, m), 2.07-2.03 (1H, m), 1.00 (6H, d, J=6.6 Hz), LCMS (Method A) m/z: M+1 obs 471.1, t$_R$=3.11 min.

Step-2: (4-(6-isobutoxypyrimidin-4-yl)piperazin-1-yl)(5-(6-methoxypyridin-3-yl)-1-methyl-1H-pyrazol-3-yl)methanone A mixture of (5-iodo-1-methyl-1H-pyrazol-3-yl) (4-(6-isobutoxypyrimidin-4-yl)piperazin-1-yl)methanone (20 mg, 0.043 mmol), (6-methoxypyridin-3-yl)boronic acid (8.5 mg, 0.055 mmol), palladium acetate (1.9 mg), triphenylphosphine (4.5 mg), and sodium carbonate (18 mg, 0.17 mmol) in dioxane-THF-water (1.6 mL, 1:0.3:0.3) was stirred at 150° C. for 10 min under microwave irradiation. After cooling to rt, the mixture was poured onto water, and the aqueous layer was extracted with EtOAc (three times). The combined organic layer was concentrated in vacuo. The residue was purified by preparative LC-MS to give 6.5 mg (34% yields) of the title compound.

Quality control analytical conditions (Method B) used in Table 1-1 to Table 1-13 are described below for Examples 1-246.

TABLE 1-1

| Example | name | Structure |
|---|---|---|
| 1 | (3-fluoro-4-methylphenyl)(4-(6-isobutoxypyrimidin-4-yl)piperazin-1-yl)methanone | 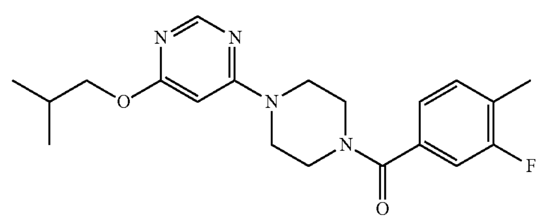 [SMILES: Cc1ccc(C(=O)N2CCN(c3cc(OCC(C)C)ncn3)CC2)cc1F] |
| 2 | (4-(6-((1,3-dimethyl-1H-pyrazol-5-yl)methoxy)pyrimidin-4-yl)piperazin-1-yl)(3-fluoro-4-methylphenyl)methanone | 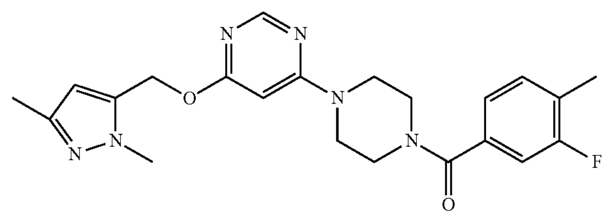 [SMILES: Cc1cc(COc2cc(N3CCN(C(=O)c4ccc(C)c(F)c4)CC3)ncn2)n(C)n1] |

TABLE 1-1-continued

| | | |
|---|---|---|
| 3 | (R)-2-hydroxy-1-(4-(6-isobutoxypyrimidin-4-yl)piperazin-1-yl)-2-phenylethanone | 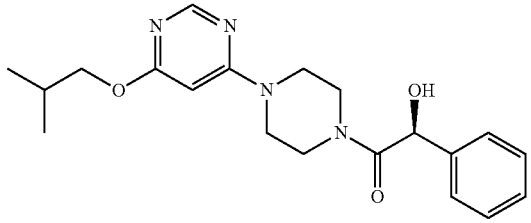 |
| 4 | (S)-2-hydroxy-1-(4-(6-isobutoxypyrimidin-4-yl)piperazin-1-yl)-3-phenylpropan-1-one | 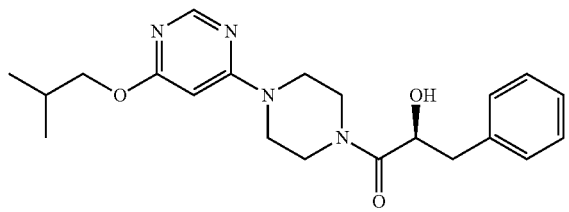 [SMILES: CC(C)COc1cc(N2CCN(C(=O)[C@@H](O)Cc3ccccc3)CC2)ncn1] |
| 5 | (R)-2-hydroxy-1-(4-(6-isobutoxypyrimidin-4-yl)piperazin-1-yl)-3-phenylpropan-1-one | 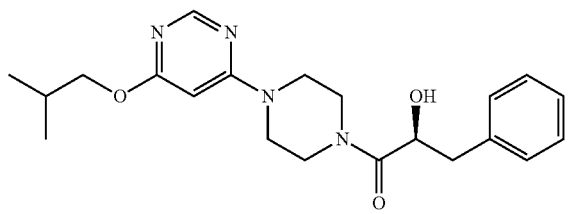 [SMILES: CC(C)COc1cc(N2CCN(C(=O)[C@@H](O)Cc3ccccc3)CC2)ncn1] |
| 6 | (4-(6-(cyclopropylmethoxy)pyrimidin-4-yl)piperazin-1-yl)(3-fluoro-4-methylphenyl)methanone | 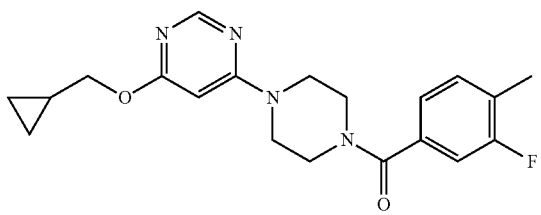 [SMILES: Cc1ccc(C(=O)N2CCN(c3cc(OCC4CC4)ncn3)CC2)cc1F] |
| 7 | 4-(6-(cyclopentyloxy)pyrimidin-4-yl)piperazin-1-yl)(3-fluoro-4-methylphenyl)methanone | 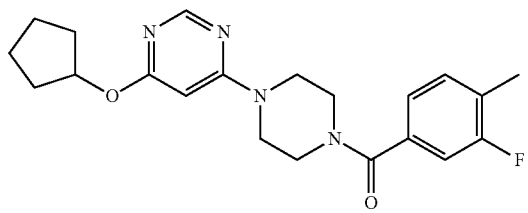 [SMILES: Cc1ccc(C(=O)N2CCN(c3cc(OC4CCCC4)ncn3)CC2)cc1F] |
| 8 | 3-(fluoro-4-methylphenyl)(4-(6-(2,2,2-trifluoroethoxy)pyrimidin-4-yl)piperazin-1-yl)methanone | 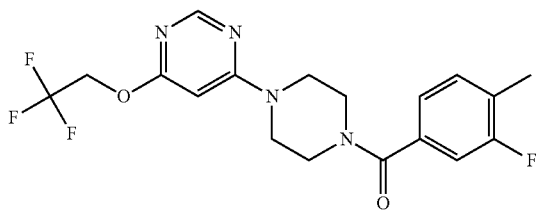 [SMILES: Cc1ccc(C(=O)N2CCN(c3cc(OCC(F)(F)F)ncn3)CC2)cc1F] |
| 9 | (1H-indol-4-yl)(4-(6-isobutoxypyrimidin-4-yl)piperazin-1-yl)methanone | 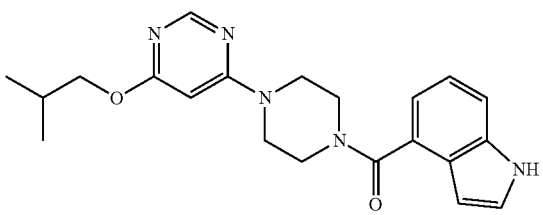 [SMILES: CC(C)COc1cc(N2CCN(C(=O)c3cccc4[nH]ccc34)CC2)ncn1] |

TABLE 1-1-continued

| | | |
|---|---|---|
| 10 | (S)-tert-butyl (2-(4-(6-isobutoxypyrimidin-4-yl)piperazin-1-yl)-2-oxo-1-phenylethyl)carbamate | |
| 11 | (R)-tert-butyl (2-(4-(6-isobutoxypyrimidin-4-yl)piperazin-1-yl)-2-oxo-1-phenylethyl)carbamate | |
| 12 | (3-fluoro-4-methylphenyl)(4-(6-(isobutylamino)pyrimidin-4-yl)piperazin-1-yl)methanone | |
| 13 | (4-(6-isobutoxypyrimidin-4-yl)piperazin-1-yl)(6-methoxypyridin-2-yl)methanone | |
| 14 | (4-(6-isobutoxypyrimidin-4-yl)piperazin-1-yl)(1-methyl-3-(trifluoromethyl)-1H-pyrazol-5-yl)methanone | |
| 15 | (4-(6-isobutoxypyrimidin-4-yl)piperazin-1-yl)(3-(trifluoromethoxy)phenyl)methanone | |
| 16 | 4-(6-cyclobutoxypyrimidin-4-yl)piperazin-1-yl)(3-fluoro-4-methylphenyl)methanone | |

TABLE 1-1-continued
| | | |
|---|---|---|
| 17 | 4-(3-fluoro-4-methylbenzoyl)-1-(6-isobutoxypyrimidin-4-yl)piperazin-2-one | 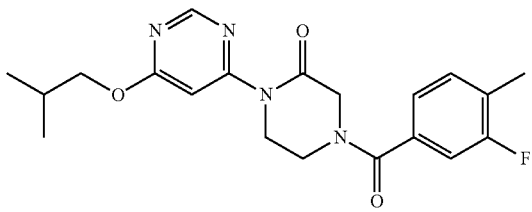 [SMILES: Cc1ccc(C(=O)N2CCN(c3cc(OCC(C)C)ncn3)C(=O)C2)cc1F] |
| 18 | (4-(6-isobutoxypyrimidin-4-yl)piperazin-1-yl)(quinolin-2-yl)methanone | 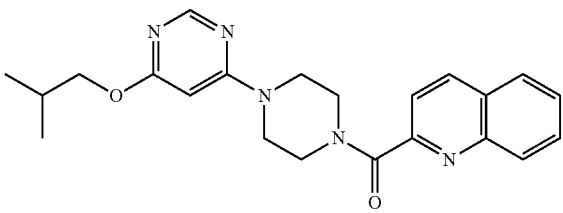 [SMILES: CC(C)COc1cc(N2CCN(C(=O)c3ccc4ccccc4n3)CC2)ncn1] |
| Example | reactant A | reactant B | tR (min) | observed MS |
|---|---|---|---|---|
| 1 | | | 1.87 | 373.3 |
| 2 | | | 1.59 | 424.9 |
| 3 | | | 1.69 | 369.3 |
| 4 | | | 1.72 | 383.2 |
| 5 | | | 1.72 | 383.4 |

TABLE 1-1-continued
| 6 | 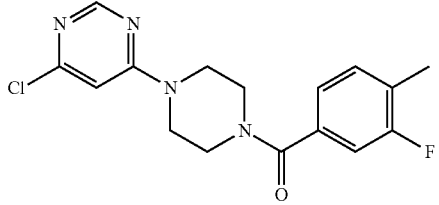 [SMILES: Cc1ccc(C(=O)N2CCN(c3cc(Cl)ncn3)CC2)cc1F] | 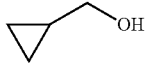 | 1.78 | 368.7 |
| --- | --- | --- | --- | --- |
| 7 | 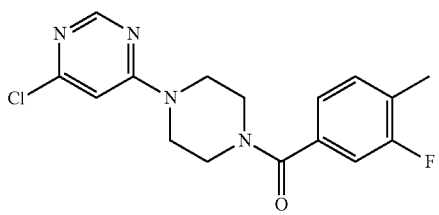 [SMILES: Cc1ccc(C(=O)N2CCN(c3cc(Cl)ncn3)CC2)cc1F] |  | 1.9 | 384.9 |
| 8 | 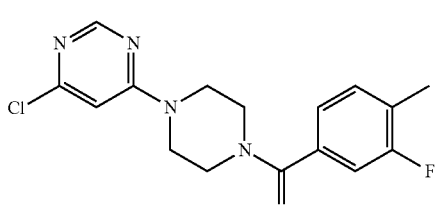 | 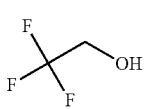 | 1.82 | 398.8 |
| 9 | 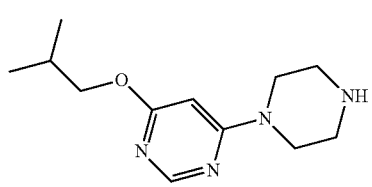 [SMILES: CC(C)COc1cc(N2CCNCC2)ncn1] | 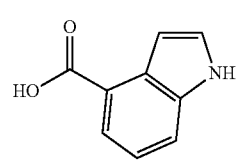 [SMILES: O=C(O)c1cccc2[nH]ccc12] | 1.67 | 378.2 |
| 10 | 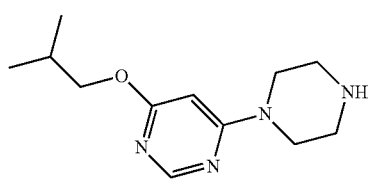 [SMILES: CC(C)COc1cc(N2CCNCC2)ncn1] | 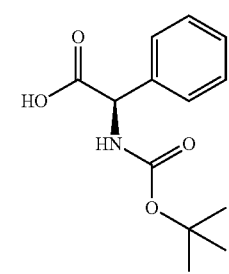 [SMILES: CC(C)(C)OC(=O)N[C@@H](C(=O)O)c1ccccc1] | 2.01 | 469.9 |
| 11 | 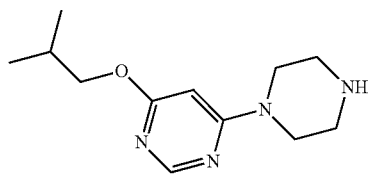 [SMILES: CC(C)COc1cc(N2CCNCC2)ncn1] | 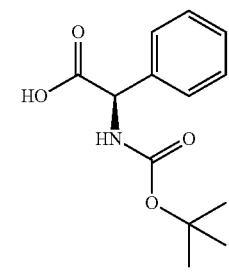 [SMILES: CC(C)(C)OC(=O)N[C@@H](C(=O)O)c1ccccc1] | 2.01 | 468.2 |
| 12 | 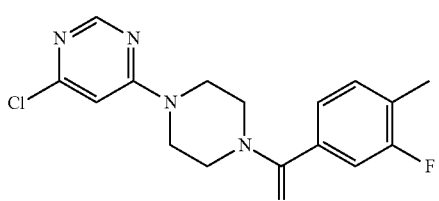 | 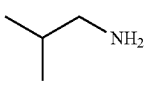 | 1.64 | 370.3 |

TABLE 1-1-continued

| # | Structure 1 | Structure 2 | | |
|---|---|---|---|---|
| 13 | isobutoxy-pyrimidinyl-piperazine | 6-methoxypicolinic acid | 1.76 | 372.0 |
| 14 | isobutoxy-pyrimidinyl-piperazine | 1-methyl-3-(trifluoromethyl)-1H-pyrazole-5-carboxylic acid | 1.86 | 413.0 |
| 15 | isobutoxy-pyrimidinyl-piperazine | 3-(trifluoromethoxy)benzoic acid | 1.94 | 425.0 |
| 16 | 6-chloropyrimidinyl-piperazine-(3-fluoro-4-methylbenzoyl) | cyclobutanol | 1.79 | 371.1 |
| 17 | alternative route | | 1.87 | 385.3 |
| 18 | isobutoxy-pyrimidinyl-piperazine | quinoline-2-carboxylic acid | 1.8 | 392.2 |

TABLE 1-2

| # | Name | Structure 1 | Structure 2 | Structure 3 | RT | MS |
|---|---|---|---|---|---|---|
| 19 | (4-fluorophenyl)(4-(6-isobutoxypyrimidin-4-yl)piperazin-1-yl)methanone | | | | 1.77 | 359.1 |
| 20 | (4-(6-isobutoxypyrimidin-4-yl)piperazin-1-yl)(1-methyl-5-(trifluoromethyl)-1H-pyrazol-3-yl)methanone | | | | 1.83 | 413.1 |
| 21 | (4-(6-isobutoxypyrimidin-4-yl)piperazin-1-yl)(2-methyl-2H-indazol-3-yl)methanone | | | | 1.74 | 395.2 |
| 22 | (4-(6-isobutoxypyrimidin-4-yl)piperazin-1-yl)(1-methyl-1H-indazol-3-yl)methanone | | | | 1.83 | 394.1 |

TABLE 1-2-continued
| | | | | | |
|---|---|---|---|---|---|
| 23 | (4-(6-isobutoxypyrimidin-4-yl) piperazin-1-yl)(1-methyl-1H-benzo[d]imidazol-2-yl)methanone | 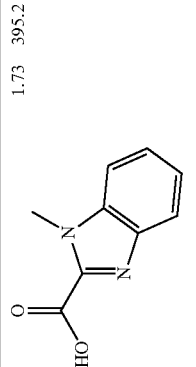 | 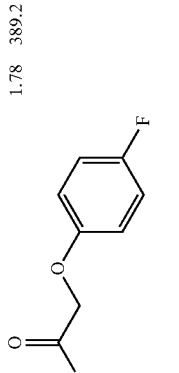 | 1.73 | 395.2 |
| 24 | 2-(4-fluorophenoxy)-1-(4-(6-isobutoxypyrimidin-4-yl)piperazin-1-yl)ethanone | | | 1.78 | 389.2 |
| 25 | (4-chloro-2-hydroxyphenyl)(4-(6-isobutoxypyrimidin-4-yl)piperazin-1-yl)methanone | | | 1.74 | 389.3 |
| 26 | 2-(4-(6-isobutoxypyrimidin-4-yl)piperazin-1-yl)-2-oxoethyl)isoindolin-1-one | 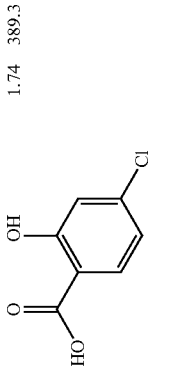 | 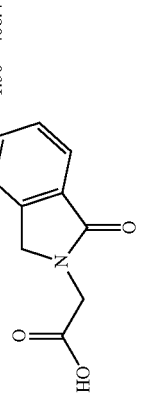 | 1.56 | 408.4 |

TABLE 1-2-continued

| | | | | | |
|---|---|---|---|---|---|
| 27 | (S)-2-amino-1-(4-(6-isobutoxypyrimidin-4-yl)piperazin-1-yl)-2-phenylethanone | | | 1.54 | 370.3 |
| 28 | (R)-2-amino-1-(4-(6-isobutoxypyrimidin-4-yl)piperazin-1-yl)-2-phenylethanone | | | 1.54 | 370.3 |
| 29 | (1-methyl-5-(trifluoromethyl)-1H-pyrazol-3-yl)(4-(6-(2,2,2-trifluoroethoxy)pyrimidin-4-yl)piperazin-1-yl)methanone | | | 1.76 | 439.1 |
| 30 | (1-methyl-1H-indazol-3-yl)(4-(6-(2,2,2-trifluoroethoxy)pyrimidin-4-yl)piperazin-1-yl)methanone | | | 1.77 | 421.2 |

TABLE 1-2-continued

| | | | | | |
|---|---|---|---|---|---|
| 31 | (4-(6-isobutoxypyrimidin-4-yl)piperazin-1-yl)(quinolin-3-yl)methanone | [structure] | [structure] | 1.67 | 392.2 |
| 32 | (8-hydroxyquinolin-2-yl)(4-(6-isobutoxypyrimidin-4-yl)piperazin-1-yl)methanone | [structure] | [structure] | 1.77 | 406.4 |
| 33 | (1H-indazol-3-yl)(4-(6-isobutoxypyrimidin-4-yl)piperazin-1-yl)methanone | [structure] | [structure] | 1.66 | 379.5 |
| 34 | (4-(6-isobutoxypyrimidin-4-yl)piperazin-1-yl)(quinoxalin-2-yl)methanone | [structure] | [structure] | 1.75 | 393.3 |

TABLE 1-2-continued
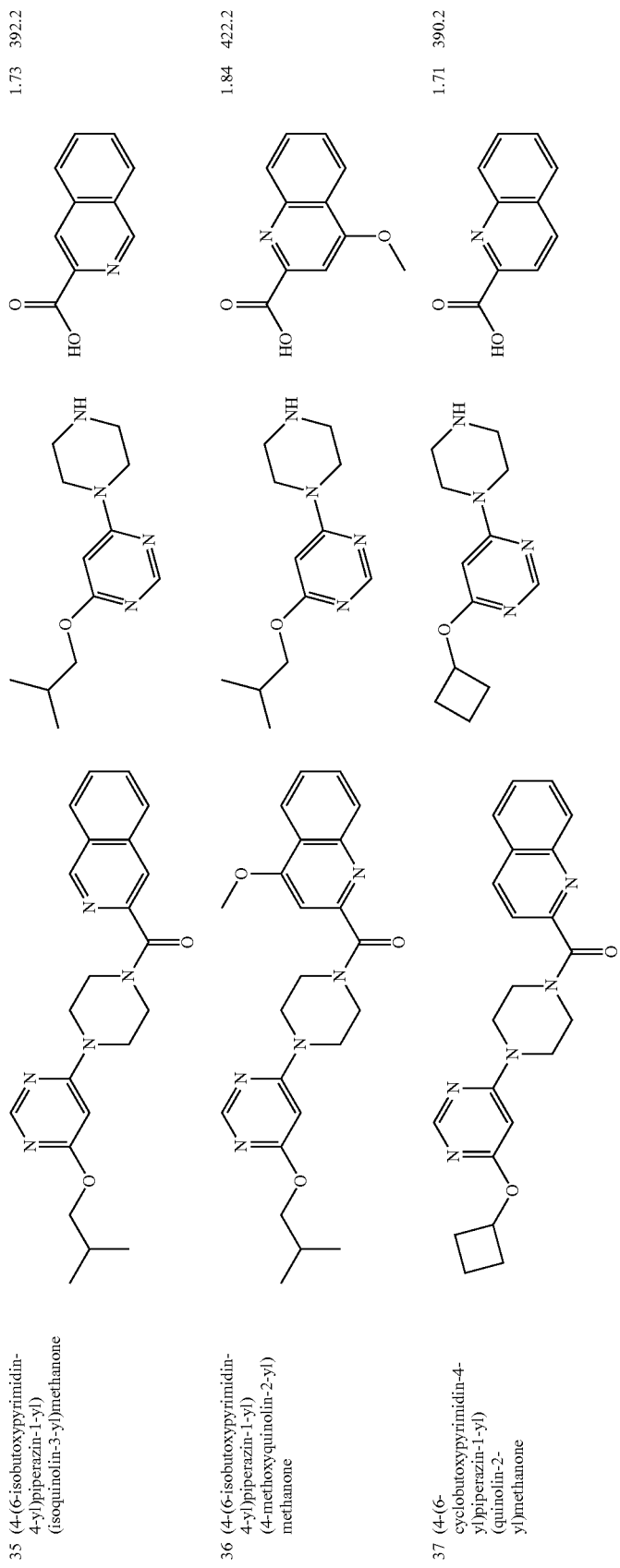
| # | Name | | | | | |
|---|---|---|---|---|---|---|
| 35 | (4-(6-isobutoxypyrimidin-4-yl)piperazin-1-yl)(isoquinolin-3-yl)methanone | | | | 1.73 | 392.2 |
| 36 | (4-(6-isobutoxypyrimidin-4-yl)piperazin-1-yl)(4-methoxyquinolin-2-yl)methanone | | | | 1.84 | 422.2 |
| 37 | (4-(6-cyclobutoxypyrimidin-4-yl)piperazin-1-yl)(quinolin-2-yl)methanone | | | | 1.71 | 390.2 |

TABLE 1-3
| | | | | | |
|---|---|---|---|---|---|
| 38 | (4-(6-cyclo-butoxypyrimidin-4-yl)piperazin-1-yl)(1-methyl-1H-indazol-3-yl)methanone | 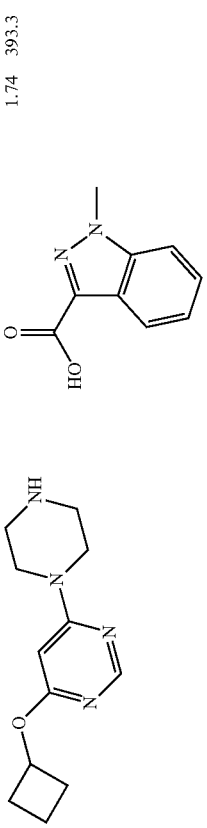 | | | 1.74 393.3 |
| 39 | (4-chloro-3-fluorophenyl)(4-(6-isobutoxy-pyrimidin-4-yl)piperazin-1-yl)methanone | | | | 1.88 391.4 |
| 40 | (4-fluoro-3-methylphenyl)(4-(6-isobutoxy-pyrimidin-4-yl)piperazin-1-yl)methanone | | | | 1.85 373.3 |
| 41 | (4-(6-isobutoxy-pyrimidin-4-yl)piperazin-1-yl)(pyrazolo[1,5-a]pyridin-2-yl)methanone | | | | 1.68 381.3 |

TABLE 1-3-continued

| | | | | | |
|---|---|---|---|---|---|
| 42 | (2-hydroxy-4-(trifluoromethyl)phenyl)(4-(6-isobutoxypyrimidin-4-yl)piperazin-1-yl)methanone | [structure] | [structure] | 1.77 | 423.4 |
| 43 | (4-(6-isobutoxypyrimidin-4-yl)piperazin-1-yl)(1-methyl-1H-indol-2-yl)methanone | [structure] | [structure] | 1.93 | 394.3 |
| 44 | (1-(2-hydroxyethyl)-1H-indazol-3-yl)(4-(6-isobutoxypyrimidin-4-yl)piperazin-1-yl)methanone | [structure] | [structure] | 1.6 | 423.2 |
| 45 | 1-(4-(6-isobutoxypyrimidin-4-yl)piperazin-1-yl)-2-phenoxyethanone | [structure] | [structure] | 1.76 | 371.3 |
| 46 | (R)-1-(4-(6-isobutoxypyrimidin-4-yl)piperazin-1-yl)-2-phenoxypropan-1-one | [structure] | [structure] | 1.83 | 385.3 |

TABLE 1-3-continued

| | | | | | |
|---|---|---|---|---|---|
| 47 | 1-(4-(6-isobutoxy-pyrimidin-4-yl)piperazin-1-yl)-2-((6-(trifluoromethyl)pyridin-3-yl)oxy)ethanone | | | 1.74 | 438.4 |
| 48 | 2-(4-fluorophenoxy)-1-(4-(6-isobutoxy-pyrimidin-4-yl)piperazin-1-yl)propan-1-one | | | 1.82 | 403.3 |
| 49 | (2,3-dihydro-benzofuran-2-yl)(4-(6-isobutoxy-pyrimidin-4-yl)piperazin-1-yl)methanone | | | 1.8 | 383.2 |
| 50 | 2-(4-fluorophenoxy)-1-(4-(6-(2,2,2-trifluoroethoxy)pyrimidin-4-yl)piperazin-1-yl)ethanone | | | 1.71 | 413.3 |
| 51 | 1-(4-(6-cyclobutoxy-pyrimidin-4-yl)piperazin-1-yl)-2-(4-fluoro-phenoxy)ethanone | | | 1.68 | 387.2 |

TABLE 1-3-continued
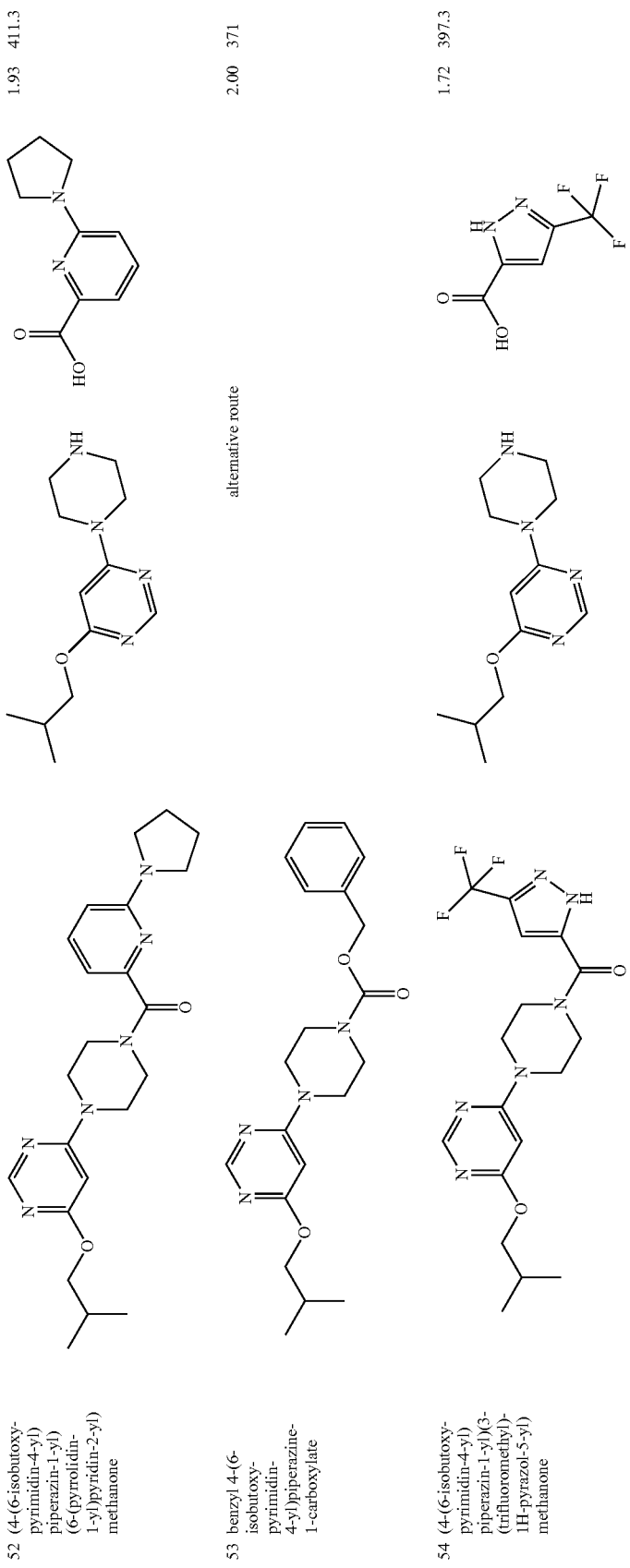
| 52 | (4-(6-isobutoxy-pyrimidin-4-yl)piperazin-1-yl)(6-(pyrrolidin-1-yl)pyridin-2-yl)methanone | 1.93 | 411.3 |
| 53 | benzyl 4-(6-isobutoxy-pyrimidin-4-yl)piperazine-1-carboxylate | 2.00 | 371 |
| 54 | (4-(6-isobutoxy-pyrimidin-4-yl)piperazin-1-yl)(3-(trifluoromethyl)-1H-pyrazol-5-yl)methanone | 1.72 | 397.3 |

TABLE 1-3-continued
| | | |
|---|---|---|
| 55 quinolin-2-yl(4-(6-(2,2,2-trifluoroethoxy)pyrimidin-4-yl)piperazin-1-yl)methanone | 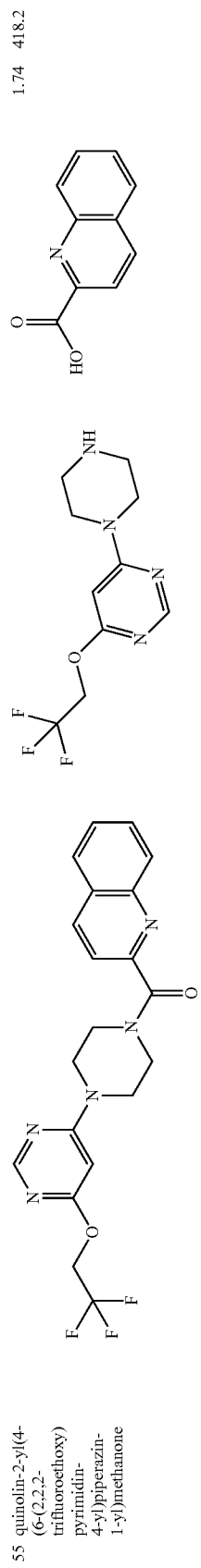 | 1.74 418.2 |
| 56 (4-(6-cyclobutoxypyrimidin-4-yl)piperazin-1-yl)(4-fluorophenyl)methanone | 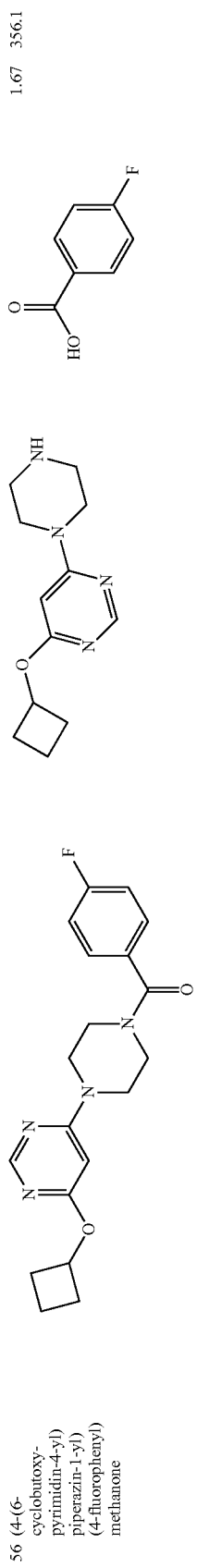 | 1.67 356.1 |

TABLE 1-4

| | | |
|---|---|---|
| 57 | 4-(2-(4-(6-isobutoxypyrimidin-4-yl)piperazin-1-yl)-2-oxoethyl)-2H-benzo[b][1,4]oxazin-3(4H)-one | 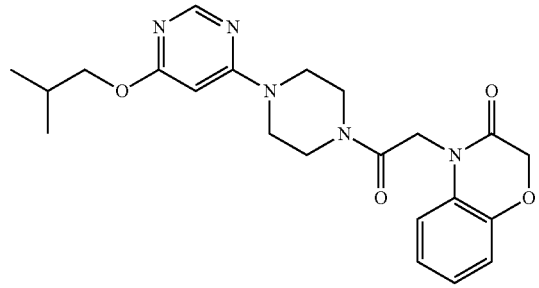 [SMILES: CC(C)COc1cc(N2CCN(C(=O)CN3C(=O)COc4ccccc43)CC2)ncn1] |
| 58 | 2-(benzo[d]isoxazol-3-yl)-1-(4-(6-isobutoxypyrimidin-4-yl)piperazin-1-yl)ethanone | 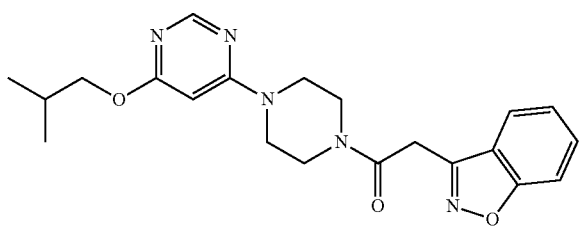 [SMILES: CC(C)COc1cc(N2CCN(C(=O)Cc3noc4ccccc34)CC2)ncn1] |
| 59 | 3-(1H-indol-1-yl)-1-(4-(6-isobutoxypyrimidin-4-yl)piperazin-1-yl)propan-1-one | 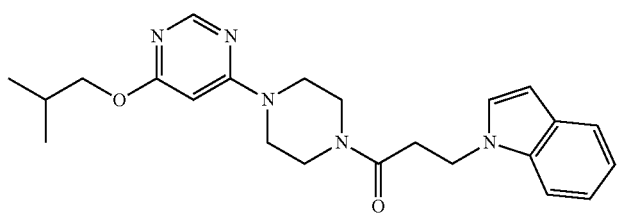 [SMILES: CC(C)COc1cc(N2CCN(C(=O)CCn3ccc4ccccc43)CC2)ncn1] |
| 60 | 2-(5-fluoro-1H-indol-3-yl)-1-(4-(6-isobutoxypyrimidin-4-yl)piperazin-1-yl)ethanone | 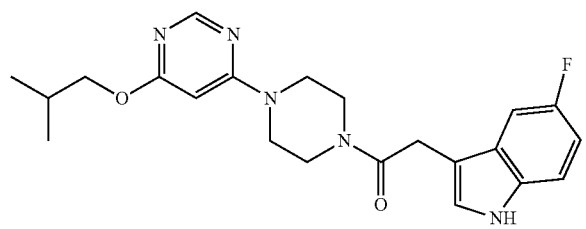 [SMILES: CC(C)COc1cc(N2CCN(C(=O)Cc3c[nH]c4ccc(F)cc34)CC2)ncn1] |
| 61 | 2-(3-(4-(6-isobutoxypyrimidin-4-yl)piperazin-1-yl)-3-oxopropyl)isoindolin-1-one | 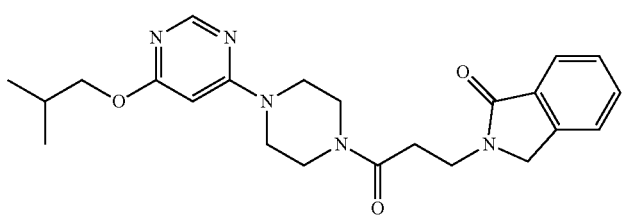 [SMILES: CC(C)COc1cc(N2CCN(C(=O)CCN3Cc4ccccc4C3=O)CC2)ncn1] |
| 62 | (4-(6-isobutoxypyrimidin-4-yl)piperazin-1-yl)(1-(2-methoxyethyl)-1H-indol-2-yl)methanone | 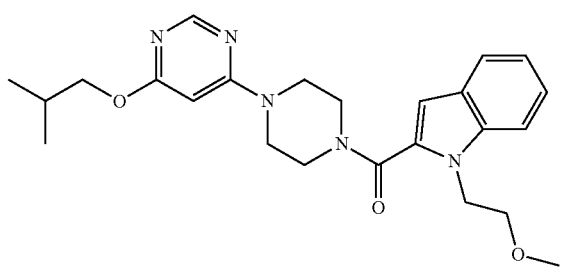 [SMILES: COCCn1c(C(=O)N2CCN(c3cc(OCC(C)C)ncn3)CC2)cc2ccccc21] |

TABLE 1-4-continued

| | | |
|---|---|---|
| 63 | (4-methoxyquinolin-2-yl)(4-(6-(2,2,2-trifluoroethoxy)pyrimidin-4-yl)piperazin-1-yl)methanone | 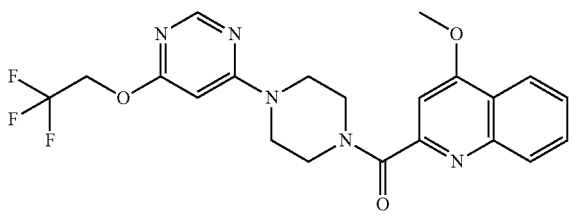 [SMILES: COc1cc(C(=O)N2CCN(c3cc(OCC(F)(F)F)ncn3)CC2)nc2ccccc12] |
| 64 | quinoxalin-2-yl(4-(6-(2,2,2-trifluoroethoxy)pyrimidin-4-yl)piperazin-1-yl)methanone | 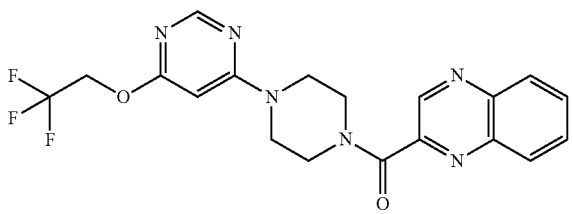 [SMILES: O=C(c1cnc2ccccc2n1)N1CCN(c2cc(OCC(F)(F)F)ncn2)CC1] |
| 65 | (8-hydroxyquinolin-2-yl)(4-(6-(2,2,2-trifluoroethoxy)pyrimidin-4-yl)piperazin-1-yl)methanone | 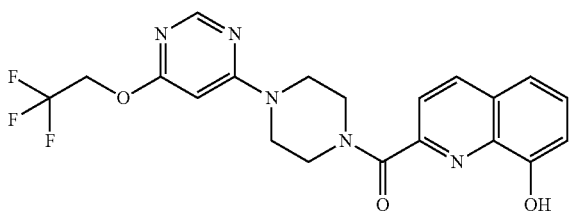 [SMILES: O=C(c1ccc2cccc(O)c2n1)N1CCN(c2cc(OCC(F)(F)F)ncn2)CC1] |
| 66 | (1H-indol-4-yl)(4-(6-(2,2,2-trifluoroethoxy)pyrimidin-4-yl)piperazin-1-yl)methanone | 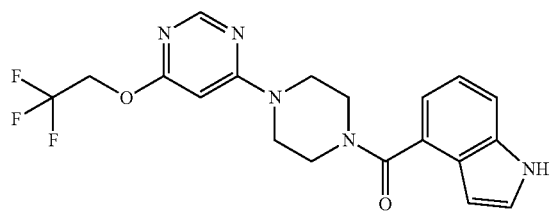 [SMILES: O=C(c1cccc2[nH]ccc12)N1CCN(c2cc(OCC(F)(F)F)ncn2)CC1] |
| 67 | (2-methyl-2H-indazol-3-yl)(4-(6-(2,2,2-trifluoroethoxy)pyrimidin-4-yl)piperazin-1-yl)methanone | 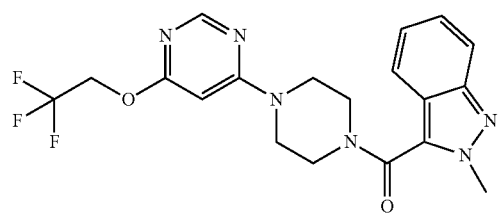 [SMILES: Cn1nc2ccccc2c1C(=O)N1CCN(c2cc(OCC(F)(F)F)ncn2)CC1] |
| 68 | (1H-indazol-3-yl)(4-(6-(2,2,2-trifluoroethoxy)pyrimidin-4-yl)piperazin-1-yl)methanone | 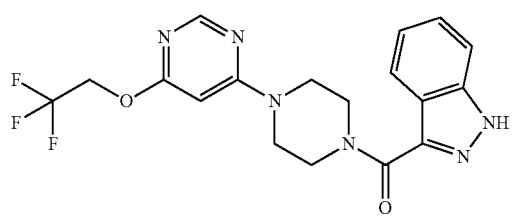 [SMILES: O=C(c1n[nH]c2ccccc12)N1CCN(c2cc(OCC(F)(F)F)ncn2)CC1] |
| 69 | 1-(4-(6-isobutoxypyrimidin-4-yl)piperazin-1-yl)-2-(phenylsulfonyl)ethanone | 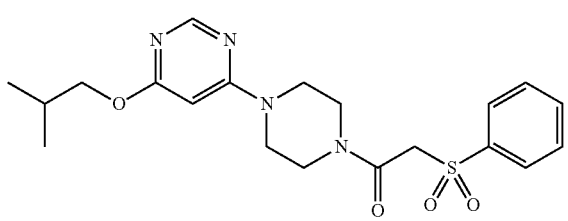 [SMILES: CC(C)COc1cc(N2CCN(C(=O)CS(=O)(=O)c3ccccc3)CC2)ncn1] |

TABLE 1-4-continued

| | | |
|---|---|---|
| 70 | 1-(4-(6-isobutoxypyrimidin-4-yl)piperazin-1-yl)-2-(3-methoxyphenoxy)ethanone | 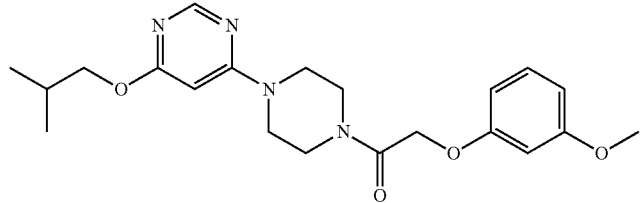 [SMILES: COc1cccc(OCC(=O)N2CCN(c3cc(OCC(C)C)ncn3)CC2)c1] |
| 71 | (1-(2-hydroxyethyl)-1H-indol-2-yl)(4-(6-isobutoxypyrimidin-4-yl)piperazin-1-yl)methanone | 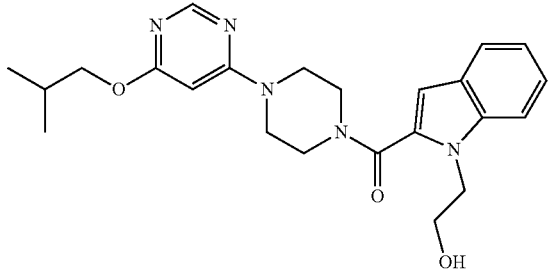 [SMILES: CC(C)COc1cc(N2CCN(C(=O)c3cc4ccccc4n3CCO)CC2)ncn1] |
| 72 | 4-fluoro-N-(2-(4-(6-isobutoxypyrimidin-4-yl)piperazin-1-yl)-2-oxoethyl)benzamide | 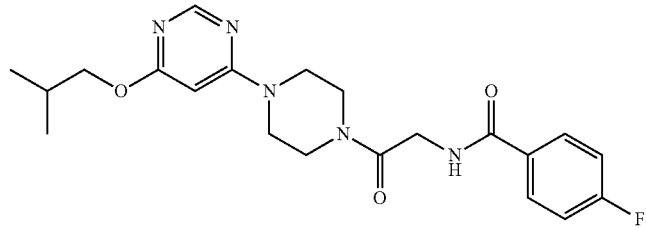 [SMILES: CC(C)COc1cc(N2CCN(C(=O)CNC(=O)c3ccc(F)cc3)CC2)ncn1] |
| 73 | N-(2-(4-(6-isobutoxypyrimidin-4-yl)piperazin-1-yl)-2-oxoethyl)-6-methoxypicolinamide | 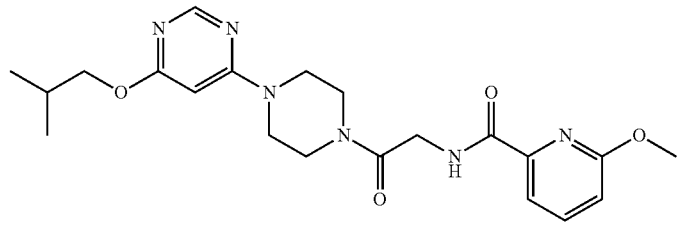 [SMILES: COc1cccc(C(=O)NCC(=O)N2CCN(c3cc(OCC(C)C)ncn3)CC2)n1] |
| 74 | N-(2-(4-(6-isobutoxypyrimidin-4-yl)piperazin-1-yl)-2-oxoethyl)-6-(2,2,2-trifluoroethoxy)nicotinamide | 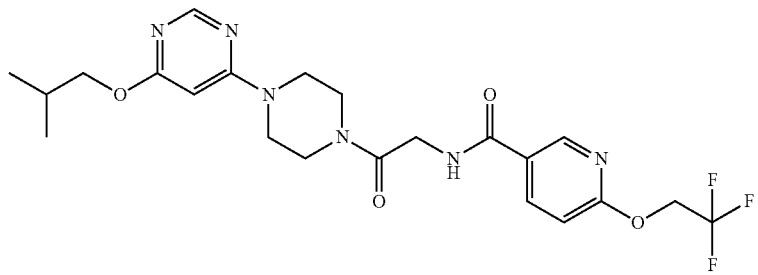 [SMILES: CC(C)COc1cc(N2CCN(C(=O)CNC(=O)c3ccc(OCC(F)(F)F)nc3)CC2)ncn1] |
| 75 | N-(2-(4-(6-isobutoxypyrimidin-4-yl)piperazin-1-yl)-2-oxoethyl)-1H-indole-4-carboxamide | 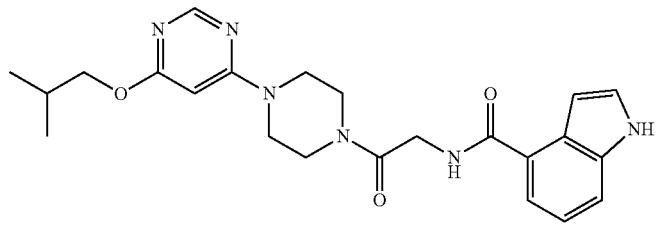 [SMILES: CC(C)COc1cc(N2CCN(C(=O)CNC(=O)c3cccc4[nH]ccc34)CC2)ncn1] |

TABLE 1-4-continued

| | | | | |
|---|---|---|---|---|
| 57 | isobutoxy-pyrimidine-piperazine | 2-(3-oxo-2H-benzo[b][1,4]oxazin-4(3H)-yl)acetic acid | 1.66 | 424.4 |
| 58 | isobutoxy-pyrimidine-piperazine | 2-(benzo[d]isoxazol-3-yl)acetic acid | 1.74 | 394.4 |
| 59 | isobutoxy-pyrimidine-piperazine | 3-(1H-indol-1-yl)propanoic acid | 1.87 | 408.3 |
| 60 | isobutoxy-pyrimidine-piperazine | 2-(5-fluoro-1H-indol-3-yl)acetic acid | 1.71 | 410.4 |
| 61 | isobutoxy-pyrimidine-piperazine | 3-(1-oxoisoindolin-2-yl)propanoic acid | 1.55 | 422.4 |
| 62 | isobutoxy-pyrimidine-piperazine | 1-(2-methoxyethyl)-1H-indole-2-carboxylic acid | 1.79 | 438.3 |
| 63 | trifluoroethoxy-pyrimidine-piperazine | 4-methoxyquinoline-2-carboxylic acid | 1.77 | 448.2 |
| 64 | trifluoroethoxy-pyrimidine-piperazine | quinoxaline-2-carboxylic acid | 1.69 | 419.2 |

TABLE 1-4-continued
| | | | | |
|---|---|---|---|---|
| 65 | 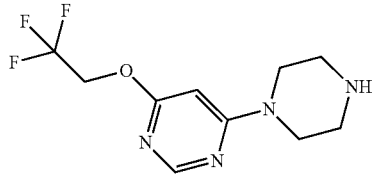 | 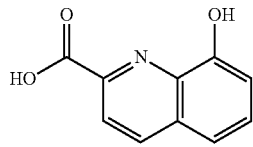 [SMILES: O=C(O)c1ccc2cccc(O)c2n1] | 1.71 | 432.4 |
| 66 | 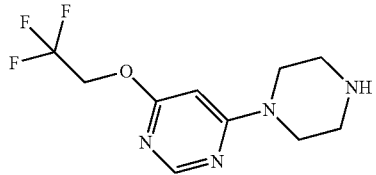 | 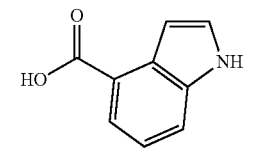 | 1.60 | 404.4 |
| 67 | 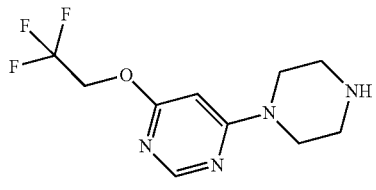 | 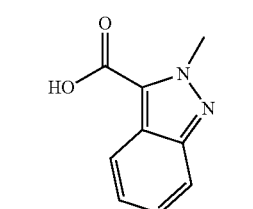 | 1.68 | 421.2 |
| 68 | 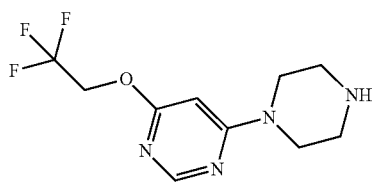 [SMILES: FC(F)(F)COc1cc(N2CCNCC2)ncn1] | 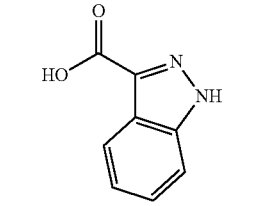 | 1.63 | 405.4 |
| 69 | 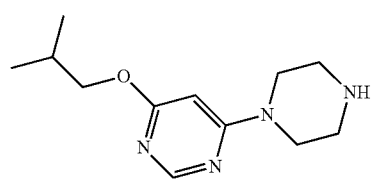 [SMILES: CC(C)COc1cc(N2CCNCC2)ncn1] | 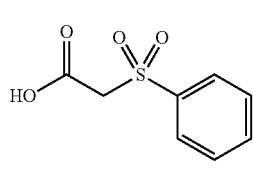 [SMILES: O=C(O)CS(=O)(=O)c1ccccc1] | 1.64 | 417.4 |
| 70 | 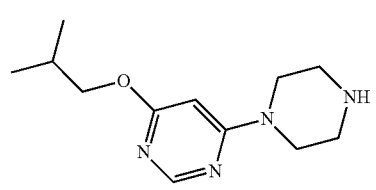 [SMILES: CC(C)COc1cc(N2CCNCC2)ncn1] | 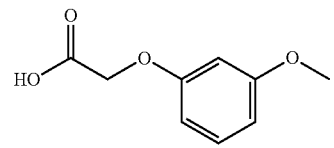 | 1.76 | 401.3 |
| 71 | 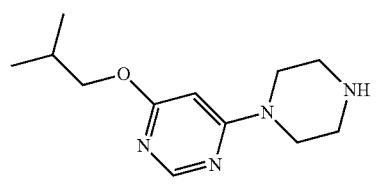 [SMILES: CC(C)COc1cc(N2CCNCC2)ncn1] | 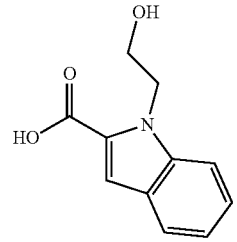 [SMILES: O=C(O)c1cc2ccccc2n1CCO] | 1.76 | 424.3 |
| 72 | alternative route | | 1.59 | 414.4 |
| 73 | alternative route | | 1.65 | 427.3 |
| 74 | alternative route | | 1.70 | 495.5 |
| 75 | alternative route | | 1.54 | 435.5 |

TABLE 1-5

| | | | | | |
|---|---|---|---|---|---|
| 76 | N-(2-(4-(6-isobutoxypyrimidin-4-yl)piperazin-1-yl)-2-oxoethyl)-1-methyl-1H-indazole-3-carboxamide | [structure] | alternative route | 1.69 | 450.6 |
| 77 | 1-(4-(6-isobutoxypyrimidin-4-yl)piperazin-1-yl)-2-(quinolin-8-yloxy)ethanone | [structure] | [structures] | 1.62 | 422.3 |
| 78 | 1-(4-(6-isobutoxypyrimidin-4-yl)piperazin-1-yl)-2-(quinolin-5-yloxy)ethanone | [structure] | alternative route | 1.63 | 422.3 |
| 79 | 1-(4-(6-isobutoxypyrimidin-4-yl)piperazin-1-yl)-2-((6-methylpyridin-3-yl)oxy)ethanone | [structure] | alternative route | 1.52 | 386.3 |

TABLE 1-5-continued

| | | | | | |
|---|---|---|---|---|---|
| 80 (4-(6-cyclobutoxypyrimidin-4-yl)piperazin-1-yl)(2-methyl-2H-indazol-3-yl)methanone | | | | 1.64 | 393.3 |
| 81 (4-(6-cyclobutoxypyrimidin-4-yl)piperazin-1-yl)(1H-indazol-3-yl)methanone | | | | 1.57 | 377.4 |
| 82 (4-(6-cyclobutoxypyrimidin-4-yl)piperazin-1-yl)(quinoxalin-2-yl)methanone | | | | 1.65 | 391.2 |
| 83 (4-(6-cyclobutoxypyrimidin-4-yl)piperazin-1-yl)(8-hydroxyquinolin-2-yl)methanone | | | | 1.68 | 404.4 |
| 84 (4-(6-cyclobutoxypyrimidin-4-yl)piperazin-1-yl)(1-methyl-3-(trifluoromethyl)-1H-pyrazol-5-yl)methanone | | | | 1.75 | 409.4 |

TABLE 1-5-continued

| | | | | |
|---|---|---|---|---|
| 85 | N-(2-(4-(6-cyclobutoxypyrimidin-4-yl)piperazin-1-yl)-2-oxoethyl)benzamide | | | 1.47  394.4 |
| 86 | benzo[b]thiophen-2-yl)(4-(6-isobutoxypyrimidin-4-yl)piperazin-1-yl)methanone | | | 1.92  397.2 |
| 87 | (4-(6-isobutoxy-pyrimidin-4-yl)piperazin-1-yl)(thieno[2,3-b]pyridin-2-yl)methanone | | | 1.68  398.2 |
| 88 | 4-(6-isobutoxy-pyrimidin-4-yl)piperazin-1-yl)(thieno[2,3-b]pyrazin-6-yl)methanone | | | 1.64  399.2 |

TABLE 1-5-continued

| | | | | |
|---|---|---|---|---|
| 89 | 3-(4-fluorophenoxy)-1-(4-(6-isobutoxypyrimidin-4-yl)piperazin-1-yl)propan-1-one | | 1.81 | 403.2 |
| 90 | 4-(6-isobutoxypyrimidin-4-yl)piperazin-1-yl)(5-phenylisoxazol-3-yl)methanone | | 1.94 | 408.2 |
| 91 | 4-(6-isobutoxypyrimidin-4-yl)piperazin-1-yl)(5-methyl-1-phenyl-1H-pyrazol-3-yl)methanone | | 1.74 | 421.2 |

TABLE 1-5-continued

| | | | | | |
|---|---|---|---|---|---|
| 92 | 4-(6-isobutoxypyrimidin-4-yl)piperazin-1-yl)(4-(oxazol-5-yl)phenyl)methanone | | | 1.65 | 408.2 |
| 93 | (4-(1H-pyrazol-1-yl)phenyl)(4-(6-isobutoxypyrimidin-4-yl)piperazin-1-yl)methanone | | | 1.73 | 407.2 |
| 94 | (3-fluoro-4-methylphenyl)((1S,4S)-5-(6-isobutoxypyrimidin-4-yl)-2,5-diazabicyclo[2.2.1]heptan-2-yl)methanone | | | 1.76 | 385.2 |

TABLE 1-6

| | | | | | |
|---|---|---|---|---|---|
| 95 | 2-(4-fluorophenoxy)-1-((1S,4S)-5-(6-isobutoxypyrimidin-4-yl)-2,5-diazabicyclo[2.2.1]heptan-2-yl)ethanone | | | 1.67 | 401.2 |
| 96 | 2-(3-fluorophenoxy)-1-(4-(6-isobutoxypyrimidin-4-yl)piperazin-1-yl)ethanone | | | 1.79 | 389.2 |
| 97 | 2-(3,4-difluorophenoxy)-1-(4-(6-isobutoxypyrimidin-4-yl)piperazin-1-yl)ethanone | | | 1.8 | 407.2 |
| 98 | 2-(2-(4-(6-isobutoxypyrimidin-4-yl)piperazin-1-yl)-2-oxoethyl)-3,4-dihydroisoquinolin-1(2H)-one | | | 1.61 | 424.3 |

TABLE 1-6-continued

| | | | | | |
|---|---|---|---|---|---|
| 99 | 1-(2-(4-(6-isobutoxypyrimidin-4-yl)piperazin-1-yl)-2-oxoethyl)-3,4-dihydroquinolin-2(1H)-one | | | 1.65 | 424.3 |
| 100 | 2-(cyclohexylamino)-1-(4-(6-isobutoxypyrimidin-1-yl)piperazin-1-yl)ethanone | | alternative route | 1.52 | 376.3 |
| 101 | 1-(4-(6-isobutoxypyrimidin-4-yl)piperazin-1-yl)-2-(1-methyl-1H-indol-3-yl)ethanone | | | 1.83 | 408.3 |
| 102 | 2-(1H-indol-3-yl)-1-(4-(6-isobutoxypyrimidin-4-yl)piperazin-1-yl)ethanone | | | 1.69 | 394.3 |

TABLE 1-6-continued

| | | | | | |
|---|---|---|---|---|---|
| 103 | 3-(2-(4-(6-isobutoxypyrimidin-4-yl)piperazin-1-yl)-2-oxoethyl)benzo[d]oxazol-2(3H)-one | | | 1.67 | 412.2 |
| 104 | 2-(1H-benzo[d]imidazol-2-yl)-1-(4-(6-isobutoxypyrimidin-4-yl)piperazin-1-yl)ethanone | | | 1.49 | 395.3 |
| 105 | 2-(2H-benzo[d][1,2,3]triazol-2-yl)-1-(4-(6-isobutoxypyrimidin-4-yl)piperazin-1-yl)ethanone | | | 1.68 | 396.2 |
| 106 | 2-(benzyloxy)-1-(4-(6-isobutoxypyrimidin-4-yl)piperazin-1-yl)ethanone | | | 1.77 | 385.3 |

TABLE 1-6-continued

| # | Name | | | | |
|---|---|---|---|---|---|
| 107 | 2-(benzo[d]isoxazol-3-yl)-1-(4-(6-(2,2,2-trifluoroethoxy)pyrimidin-4-yl)piperazin-1-yl)ethanone | | | 1.69 | 422.2 |
| 108 | 2-(2-oxo-2-(4-(6-(2,2,2-trifluoroethoxy)pyrimidin-4-yl)piperazin-1-yl)ethyl)isoindolin-1-one | | | 1.51 | 436.2 |
| 109 | 2-(3-oxo-3-(4-(6-(2,2,2-trifluoroethoxy)pyrimidin-4-yl)piperazin-1-yl)propyl)isoindolin-1-one | | | 1.53 | 450.2 |
| 110 | 2-(5-fluoro-1H-indol-3-yl)-1-(4-(6-(2,2,2-trifluoroethoxy)pyrimidin-4-yl)piperazin-1-yl)ethanone | | | 1.67 | 438.2 |

TABLE 1-6-continued

| | | | | | |
|---|---|---|---|---|---|
| 111 | 2-(benzo[d]isoxazol-3-yl)-1-(4-(6-cyclobutoxypyrimidin-4-yl)piperazin-1-yl)ethanone | | | 1.66 | 394.2 |
| 112 | (4-(6-cyclobutoxypyrimidin-4-yl)piperazin-1-yl)(thieno[2,3-b]pyridin-2-yl)methanone | | | 1.6 | 396.2 |
| 113 | (4-(6-cyclobutoxypyrimidin-4-yl)piperazin-1-yl)(2,3-dihydrobenzofuran-2-yl)methanone | | | 1.73 | 381.3 |

TABLE 1-7

| | | |
|---|---|---|
| 114 | (4-(6-cyclobutoxypyrimidin-4-yl)piperazin-1-yl)(4-methoxyquinolin-2-yl)methanone | 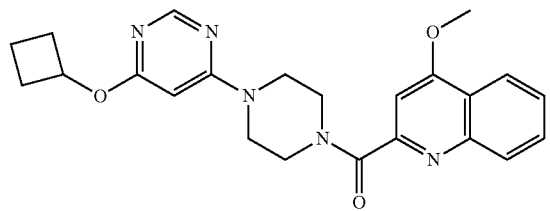 [SMILES: COc1cc(C(=O)N2CCN(c3cc(OC4CCC4)ncn3)CC2)nc2ccccc12] |
| 115 | (4-(6-cyclobutoxypyrimidin-4-yl)piperazin-1-yl)(isoquinolin-3-yl)methanone | 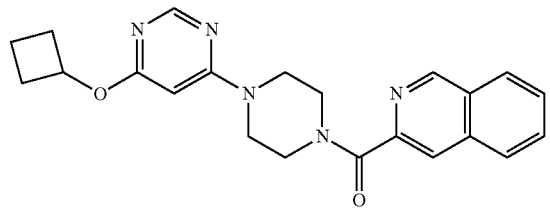 [SMILES: O=C(c1cc2ccccc2cn1)N1CCN(c2cc(OC3CCC3)ncn2)CC1] |
| 116 | (5-fluoro-1H-indazol-3-yl)(4-(6-(2,2,2-trifluoroethoxy)pyrimidin-4-yl)piperazin-1-yl)methanone | 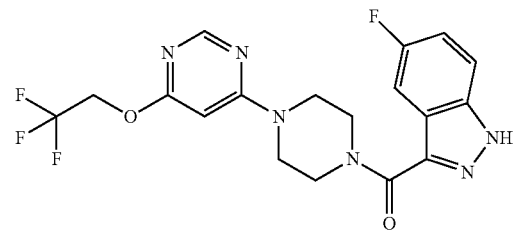 [SMILES: O=C(c1n[nH]c2ccc(F)cc12)N1CCN(c2cc(OCC(F)(F)F)ncn2)CC1] |
| 117 | (4-(6-isopropoxypyrimidin-4-yl)piperazin-1-yl)(1-methyl-1H-indazol-3-yl)methanone | 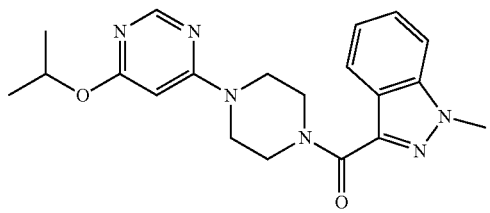 [SMILES: CC(C)Oc1cc(N2CCN(C(=O)c3nn(C)c4ccccc34)CC2)ncn1] |
| 118 | 4-fluoro-N-(3-(4-(6-isobutoxypyrimidin-4-yl)piperazin-1-yl)-3-oxopropyl)benzamide | 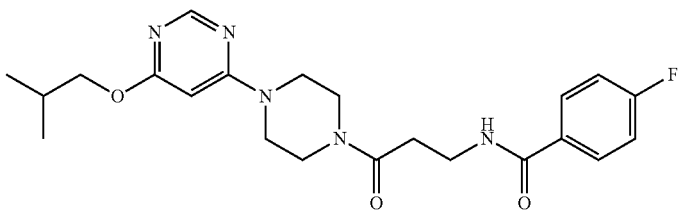 [SMILES: CC(C)COc1cc(N2CCN(C(=O)CCNC(=O)c3ccc(F)cc3)CC2)ncn1] |
| 119 | 2-(4-fluorophenyl)-1-(4-(6-isobutoxypyrimidin-4-yl)piperazin-1-yl)ethanone | 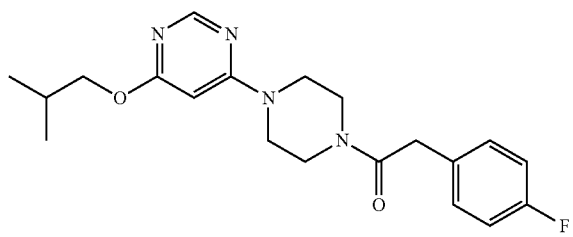 [SMILES: CC(C)COc1cc(N2CCN(C(=O)Cc3ccc(F)cc3)CC2)ncn1] |
| 120 | 1-(4-(6-isobutoxypyrimidin-4-yl)piperazin-1-yl)-2-(phenylthio)ethanone | 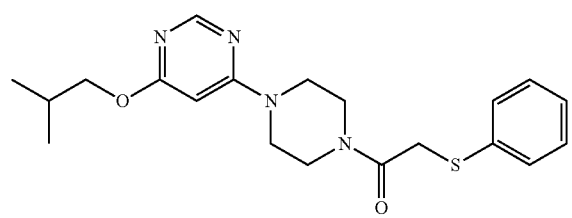 [SMILES: CC(C)COc1cc(N2CCN(C(=O)CSc3ccccc3)CC2)ncn1] |

TABLE 1-7-continued

| 121 | 2-((4-chlorophenyl)sulfonyl)-1-(4-(6-isobutoxypyrimidin-4-yl)piperazin-1-yl)ethanone | 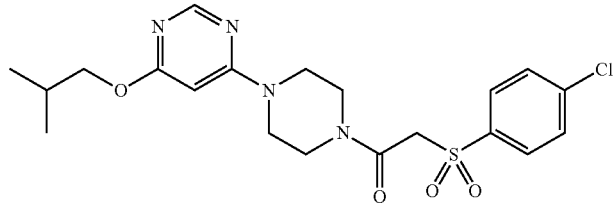 [SMILES: CC(C)COc1cc(N2CCN(C(=O)CS(=O)(=O)c3ccc(Cl)cc3)CC2)ncn1] |
| 122 | 2-((4-fluorophenyl)sulfonyl)-1-(4-(6-isobutoxypyrimidin-4-yl)piperazin-1-yl)ethanone | 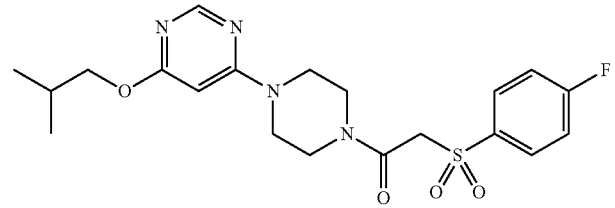 [SMILES: CC(C)COc1cc(N2CCN(C(=O)CS(=O)(=O)c3ccc(F)cc3)CC2)ncn1] |
| 123 | (S)-(1-(3-fluoro-4-methylbenzoyl)pyrrolidin-2-yl)(4-(6-isobutoxypyrimidin-4-yl)piperazin-1-yl)methanone | 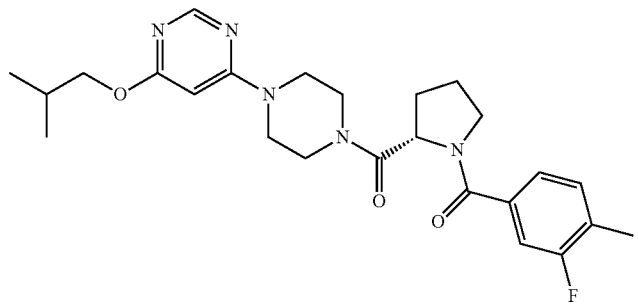 [SMILES: Cc1ccc(C(=O)N2CCC[C@H]2C(=O)N2CCN(c3cc(OCC(C)C)ncn3)CC2)cc1F] |
| 124 | (1,3-dimethyl-1H-thieno[2,3-c]pyrazol-5-yl)(4-(6-isobutoxypyrimidin-4-yl)piperazin-1-yl)methanone | 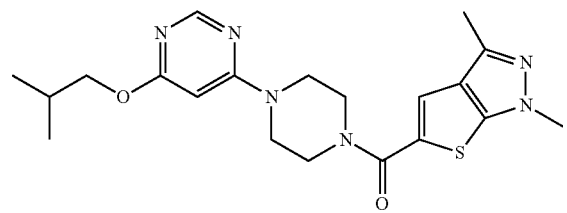 [SMILES: Cc1nn(C)c2sc(C(=O)N3CCN(c4cc(OCC(C)C)ncn4)CC3)cc12] |
| 125 | (4-(6-isobutoxypyrimidin-4-yl)piperazin-1-yl)(thiophen-2-yl)methanone | 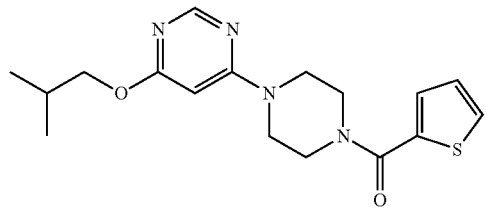 [SMILES: CC(C)COc1cc(N2CCN(C(=O)c3cccs3)CC2)ncn1] |
| 126 | imidazo[2,1-b]thiazol-6-yl(4-(6-isobutoxypyrimidin-4-yl)piperazin-1-yl)methanone | 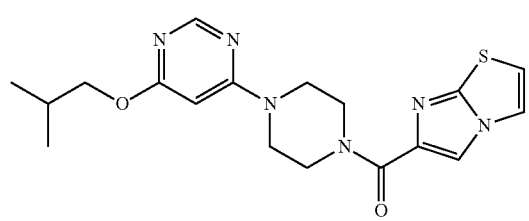 [SMILES: CC(C)COc1cc(N2CCN(C(=O)c3cn4ccsc4n3)CC2)ncn1] |
| 127 | 1-(4-(6-isobutoxypyrimidin-4-yl)piperazin-1-yl)-2-(quinolin-7-yloxy)ethanone | 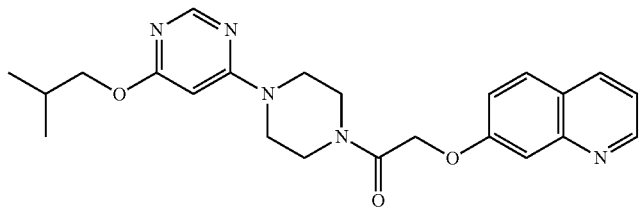 [SMILES: CC(C)COc1cc(N2CCN(C(=O)COc3ccc4cccnc4c3)CC2)ncn1] |

TABLE 1-7-continued
| | | |
|---|---|---|
| 128 | 1-(4-(6-isobutoxypyrimidin-4-yl)piperazin-1-yl)-2-(isoquinolin-8-yloxy)ethanone | 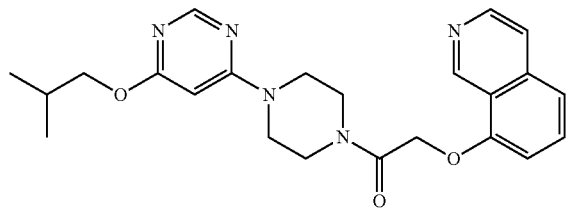 [SMILES: CC(C)COc1cc(N2CCN(C(=O)COc3cccc4ccncc34)CC2)ncn1] |
| 129 | 2-((5-fluoroquinolin-8-yl)oxy)-1-(4-(6-isobutoxypyrimidin-4-yl)piperazin-1-yl)ethanone | 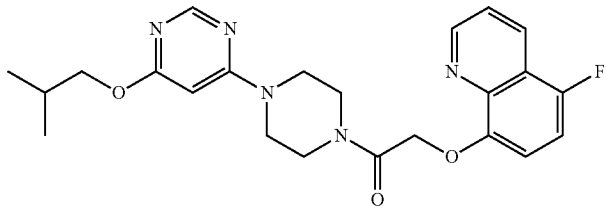 [SMILES: CC(C)COc1cc(N2CCN(C(=O)COc3ccc(F)c4cccnc34)CC2)ncn1] |
| 130 | (2-(ethylsulfonyl)phenyl)(4-(6-isobutoxypyrimidin-4-yl)piperazin-1-yl)methanone | 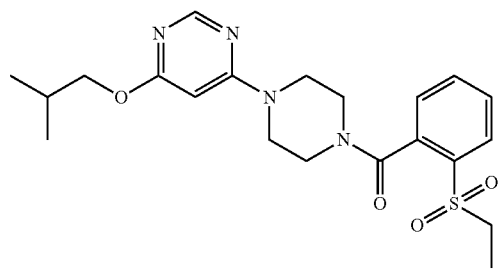 [SMILES: CCS(=O)(=O)c1ccccc1C(=O)N1CCN(c2cc(OCC(C)C)ncn2)CC1] |
| 131 | 1-(4-(6-isobutoxypyrimidin-4-yl)piperazin-1-yl)-3-phenoxypropan-1-one | 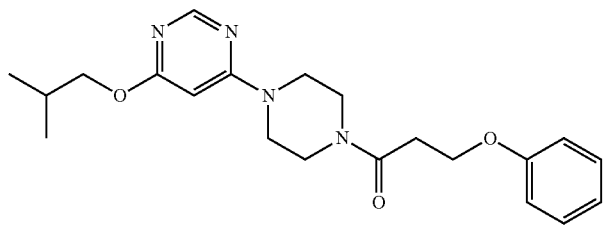 [SMILES: CC(C)COc1cc(N2CCN(C(=O)CCOc3ccccc3)CC2)ncn1] |
| 132 | 1-(4-(6-isobutoxypyrimidin-4-yl)piperazin-1-yl)-3-(m-tolyloxy)propan-1-one | 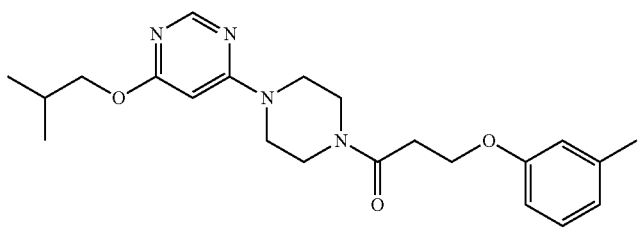 [SMILES: Cc1cccc(OCCC(=O)N2CCN(c3cc(OCC(C)C)ncn3)CC2)c1] |
| | | | | |
|---|---|---|---|---|
| 114 | 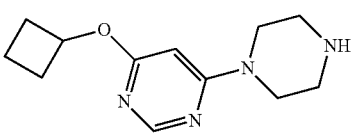 [SMILES: c1nc(OC2CCC2)cc(N2CCNCC2)n1] | 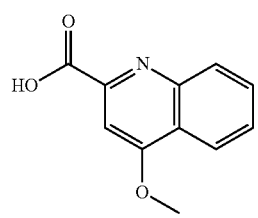 | 1.76 | 420.2 |
| 115 | 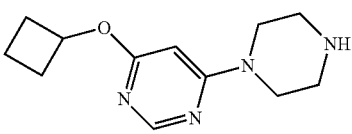 [SMILES: c1nc(OC2CCC2)cc(N2CCNCC2)n1] | 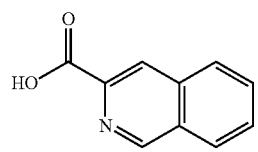 [SMILES: O=C(O)c1cc2ccccc2cn1] | 1.64 | 390.3 |

TABLE 1-7-continued
| | | | | |
|---|---|---|---|---|
| 116 | 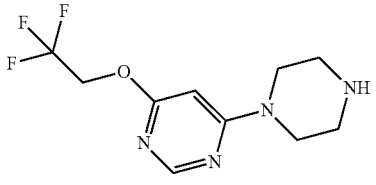 [SMILES: FC(F)(F)COc1cc(N2CCNCC2)ncn1] | 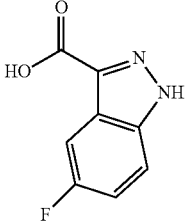 | 1.67 | 425.2 |
| 117 | 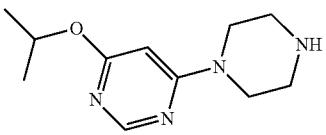 [SMILES: CC(C)Oc1cc(N2CCNCC2)ncn1] | 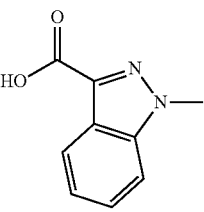 | 1.7 | 381.2 |
| 118 | 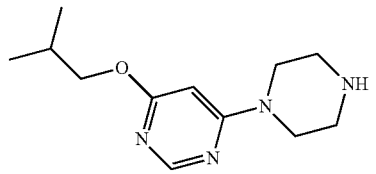 [SMILES: CC(C)COc1cc(N2CCNCC2)ncn1] | 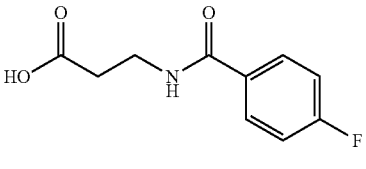 [SMILES: O=C(O)CCNC(=O)c1ccc(F)cc1] | 1.59 | 430.3 |
| 119 | 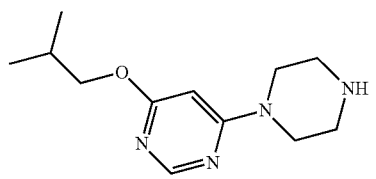 [SMILES: CC(C)COc1cc(N2CCNCC2)ncn1] | 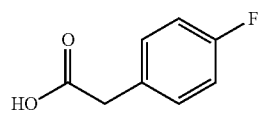 | 1.76 | 373.2 |
| 120 | 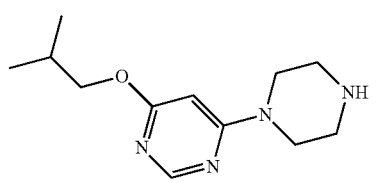 [SMILES: CC(C)COc1cc(N2CCNCC2)ncn1] | 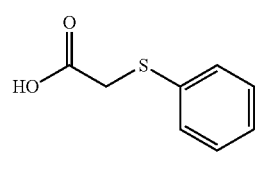 [SMILES: O=C(O)CSc1ccccc1] | 1.83 | 387.2 |
| 121 | 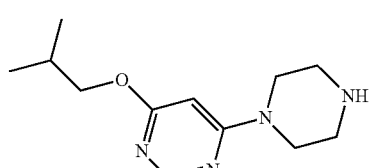 | 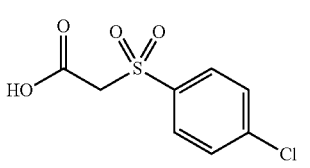 [SMILES: O=C(O)CS(=O)(=O)c1ccc(Cl)cc1] | 1.75 | 453.2 |
| 122 | 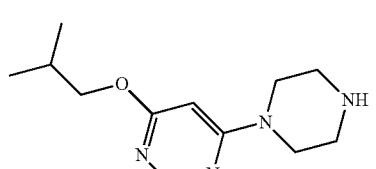 | 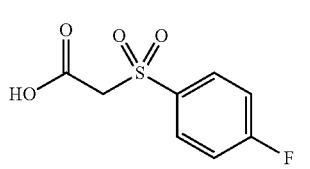 [SMILES: O=C(O)CS(=O)(=O)c1ccc(F)cc1] | 1.66 | 437.2 |
| 123 | 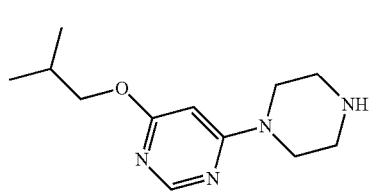 [SMILES: CC(C)COc1cc(N2CCNCC2)ncn1] | 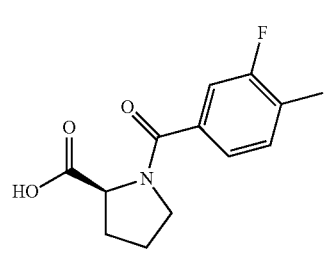 [SMILES: Cc1ccc(C(=O)N2CCC[C@H]2C(=O)O)cc1F] | 1.7 | 470.3 |

TABLE 1-7-continued
| | | | | |
|---|---|---|---|---|
| 124 | | | 1.69 | 415.2 |
| 125 | | | 1.72 | 347.2 |
| 126 | | | 1.57 | 387.2 |
| 127 | | alternative route | 1.63 | 422.3 |
| 128 | | alternative route | 1.61 | 422.3 |
| 129 | | alternative route | 1.68 | 440.3 |
| 130 | | | 1.69 | 433.2 |
| 131 | | | 1.82 | 385.3 |
| 132 | | | 1.9 | 399.3 |
TABLE 1-8
133 (4-(6-isobutoxypyrimidin-4-yl)piperazin-1-yl)(1-methyl-5-phenyl-1H-pyrazol-3-yl)methanone
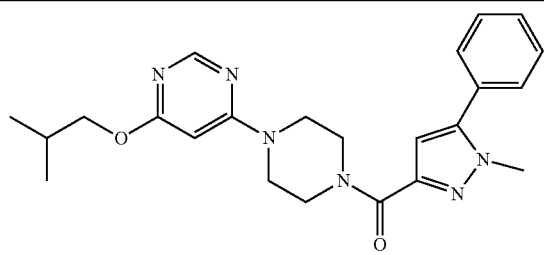

TABLE 1-8-continued

| | | |
|---|---|---|
| 134 | (4-(6-isobutoxypyrimidin-4-yl)piperazin-1-yl)(1-methyl-3-phenyl-1H-pyrazol-5-yl)methanone | 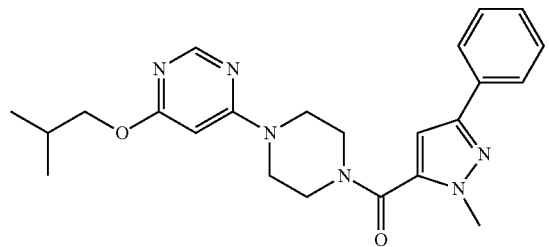 [SMILES: CC(C)COc1cc(N2CCN(C(=O)c3cc(-c4ccccc4)nn3C)CC2)ncn1] |
| 135 | 4-(6-isobutoxypyrimidin-4-yl)piperazin-1-yl)(5-methyl-1-phenyl-1H-pyrazol-4-yl)methanone | 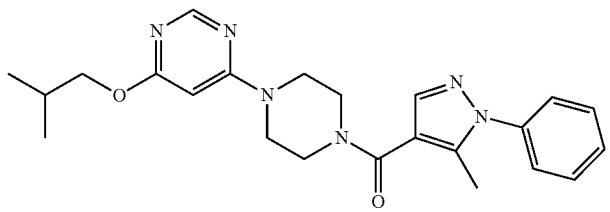 [SMILES: Cc1c(C(=O)N2CCN(c3cc(OCC(C)C)ncn3)CC2)cnn1-c1ccccc1] |
| 136 | (4-(6-isobutoxpyrimidin-4-yl)piperazin-1-yl)(5-methyl-1-phenyl-1H-1,2,3-triazol-4-yl)methanone | 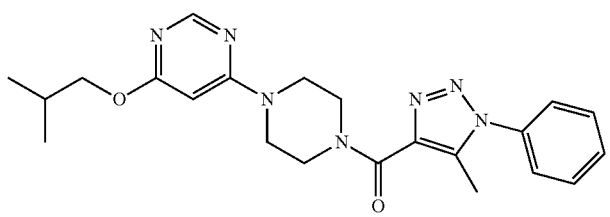 [SMILES: Cc1c(C(=O)N2CCN(c3cc(OCC(C)C)ncn3)CC2)nnn1-c1ccccc1] |
| 137 | 2-((1H-indol-4-yl)oxy)-1-(4-(6-isobutoxypyrimidin-4-yl)piperazin-1-yl)ethanone | 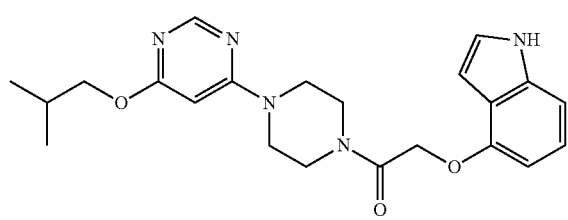 [SMILES: CC(C)COc1cc(N2CCN(C(=O)COc3cccc4[nH]ccc34)CC2)ncn1] |
| 138 | 2-(benzoylsulfonyl)-1-(4-(6-isobutoxypyrimidin-4-yl)piperazin-1-yl)ethanone | 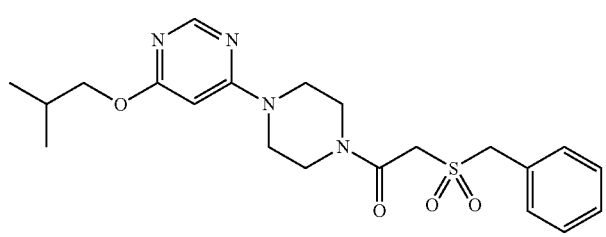 [SMILES: CC(C)COc1cc(N2CCN(C(=O)CS(=O)(=O)Cc3ccccc3)CC2)ncn1] |
| 139 | 3-(4-fluorophenoxy)-1-(4-(6-(2,2,2-trifluoroethoxy)pyrimidin-4-yl)piperazin-1-yl)propan-1-one | 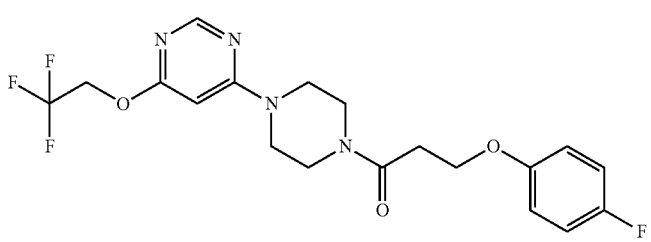 [SMILES: O=C(CCOc1ccc(F)cc1)N1CCN(c2cc(OCC(F)(F)F)ncn2)CC1] |
| 140 | 1-(4-(6-cylcobutoxypyrimidin-4-yl)piperazin-1-yl)-3-(4-fluorophenoxy)propan-1-one | 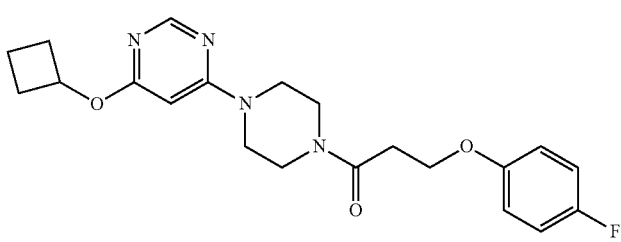 [SMILES: O=C(CCOc1ccc(F)cc1)N1CCN(c2cc(OC3CCC3)ncn2)CC1] |

TABLE 1-8-continued

| | | |
|---|---|---|
| 141 | 1-(4-(6-isobutoxypyrimidin-4-yl)piperazin-1-yl)-2-((1-methyl-1H-indol-4-yl)oxy)ethanone | 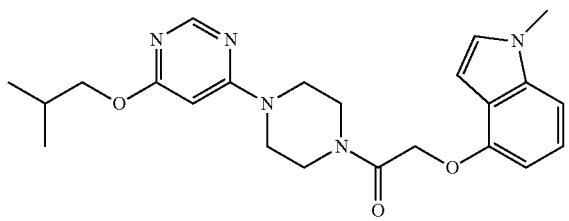 [SMILES: CC(C)COc1cc(N2CCN(C(=O)COc3cccc4c3ccn4C)CC2)ncn1] |
| 142 | benzo[d]thiazol-2-yl(4-(6-isobutoxypyrimidin-4-yl)piperazin-1-yl)methanone | 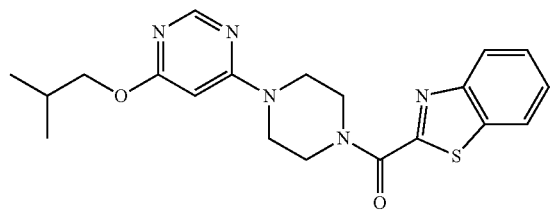 [SMILES: CC(C)COc1cc(N2CCN(C(=O)c3nc4ccccc4s3)CC2)ncn1] |
| 143 | 1-(4-(6-isobutoxypyrimidin-4-yl)piperazin-1-yl)-2-(2-(trifluoromethyl)phenoxy)ethanone | 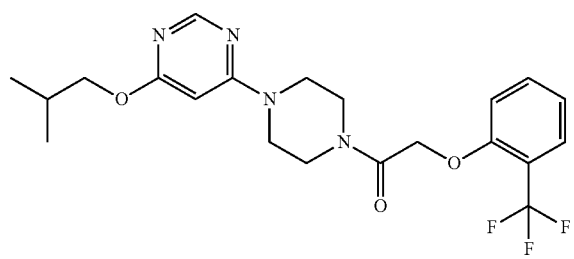 [SMILES: CC(C)COc1cc(N2CCN(C(=O)COc3ccccc3C(F)(F)F)CC2)ncn1] |
| 144 | 2-((5-chloropyridin-3-yl)oxy)-1-(4-(6-isobutoxypyrimidin-4-yl)piperazin-1-yl)ethanone | 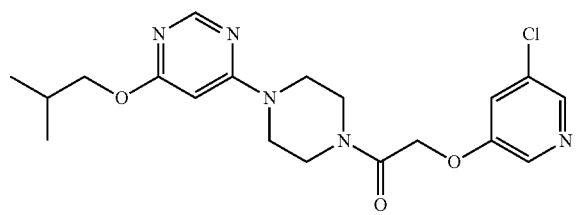 [SMILES: CC(C)COc1cc(N2CCN(C(=O)COc3cncc(Cl)c3)CC2)ncn1] |
| 145 | 1-(4-(6-isobutoxypyrimidin-4-yl)piperazin-1-yl)-2-(3-(trifluoromethoxy)phenoxy)ethanone | 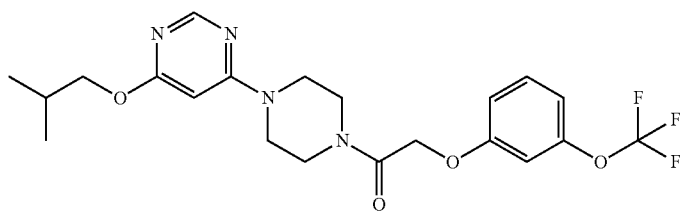 [SMILES: CC(C)COc1cc(N2CCN(C(=O)COc3cccc(OC(F)(F)F)c3)CC2)ncn1] |
| 146 | 2-(2H-benzo[d][1,2,3]triazol-2-yl)-1-(4-(6-(2,2,2-trifluoroethoxy)pyrimidin-4-yl)piperazin-1-yl)ethanone | 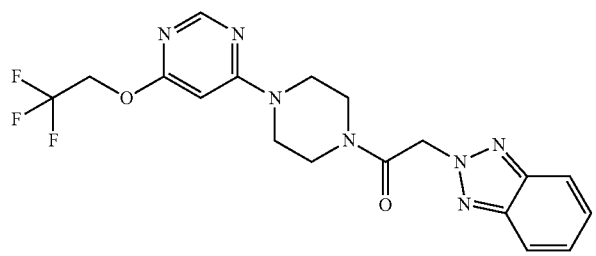 [SMILES: O=C(Cn1nc2ccccc2n1)N1CCN(c2cc(OCC(F)(F)F)ncn2)CC1] |
| 147 | 2-(quinazolin-4-yloxy)-1-(4-(6-(2,2,2-trifluoroethoxy)pyrimidin-4-yl)piperazin-1-yl)ethanone | 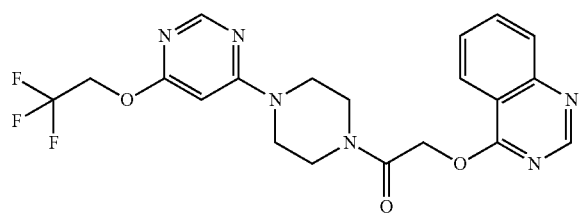 [SMILES: O=C(COc1ncnc2ccccc12)N1CCN(c2cc(OCC(F)(F)F)ncn2)CC1] |

TABLE 1-8-continued
| | | |
|---|---|---|
| 148 | (5-methyl-1-phenyl-1H-pyrazol-4-yl)(4-(6-(2,2,2-trifluoroethoxy)pyrimidin-4-yl)piperazin-1-yl)methanone | 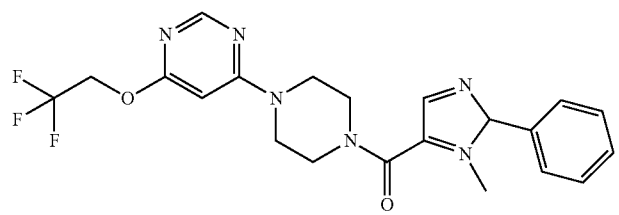 |
| 149 | 1-(benzo[d]oxazol-2-ylmethyl)-4-(6-isobutoxypyrimidin-4-yl)piperazin-2-one | 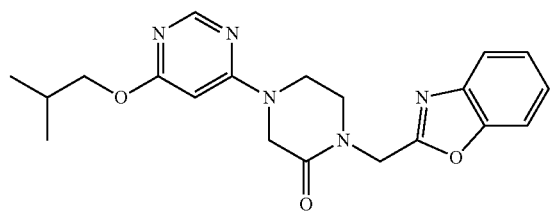 [SMILES: CC(C)COc1cc(N2CCN(Cc3nc4ccccc4o3)C(=O)C2)ncn1] |
| 150 | 1-(4-fluorobenzyl)-4-(6-(2,2,2-trifluoroethoxy)pyrimidin-4-yl)piperazin-2-one | 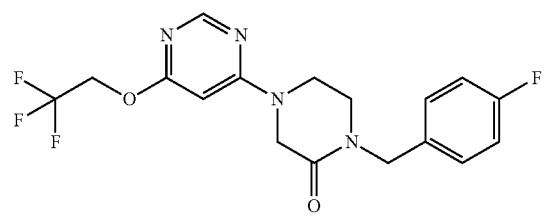 [SMILES: O=C1CN(c2cc(OCC(F)(F)F)ncn2)CCN1Cc1ccc(F)cc1] |
| 151 | 1-(4-(6-isobutoxypyrimidin-4-yl)piperazin-1-yl)-2-methyl-2-(phenylsulfonyl)propan-1-one | 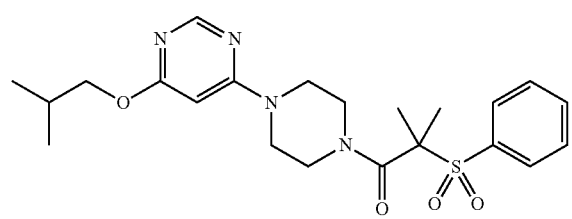 [SMILES: CC(C)COc1cc(N2CCN(C(=O)C(C)(C)S(=O)(=O)c3ccccc3)CC2)ncn1] |
| | | | | |
|---|---|---|---|---|
| 133 | 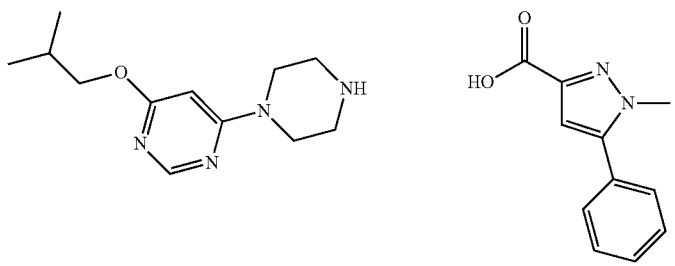 | | 1.85 | 421.3 |
| 134 | 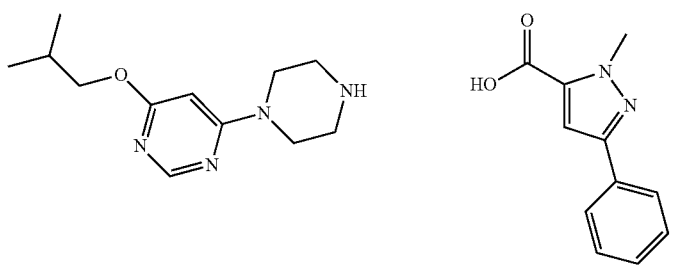 | | 1.87 | 421.3 |
| 135 | 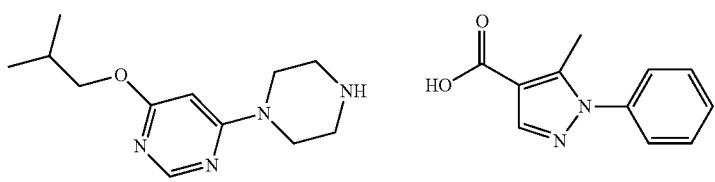 | | 1.74 | 421.3 |

TABLE 1-8-continued
| | | | | |
|---|---|---|---|---|
| 136 | 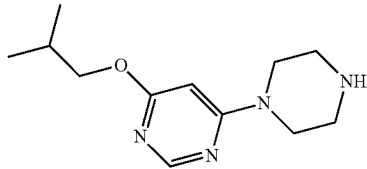 [SMILES: CC(C)COc1cc(N2CCNCC2)ncn1] | 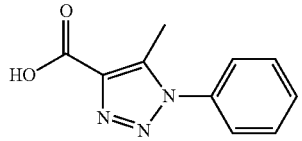 | 1.78 | 422.3 |
| 137 | 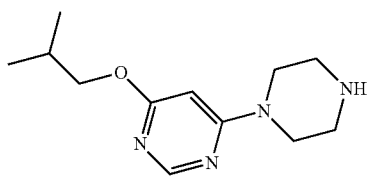 [SMILES: CC(C)COc1cc(N2CCNCC2)ncn1] | 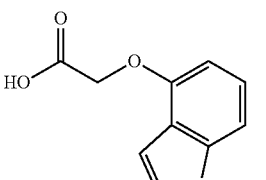 | 1.68 | 410.2 |
| 138 | 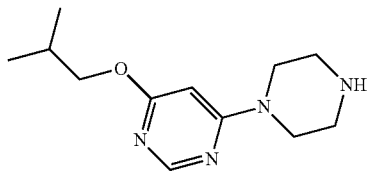 [SMILES: CC(C)COc1cc(N2CCNCC2)ncn1] | 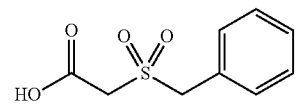 [SMILES: O=C(O)CS(=O)(=O)Cc1ccccc1] | 1.7 | 433.2 |
| 139 | 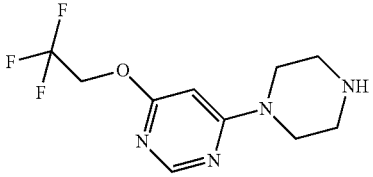 [SMILES: FC(F)(F)COc1cc(N2CCNCC2)ncn1] | 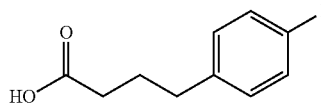 | 1.77 | 429.2 |
| 140 |  | 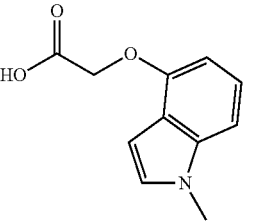 | 1.74 | 401.3 |
| 141 | 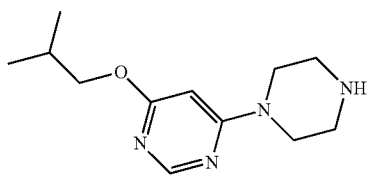 [SMILES: CC(C)COc1cc(N2CCNCC2)ncn1] | 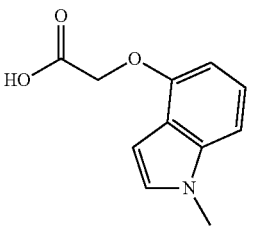 | 1.81 | 424.3 |
| 142 | 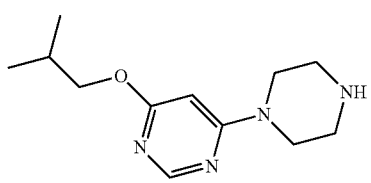 [SMILES: CC(C)COc1cc(N2CCNCC2)ncn1] | 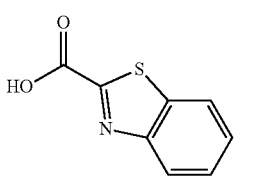 [SMILES: O=C(O)c1nc2ccccc2s1] | 1.99 | 398.2 |
| 143 | | alternative route | 1.91 | 439.2 |
| 144 | | alternative route | 1.65 | 406.2 |
| 145 | | alternative route | 1.93 | 455.2 |

TABLE 1-8-continued
| 146 | 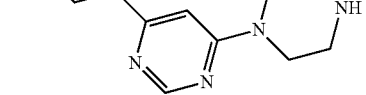 | 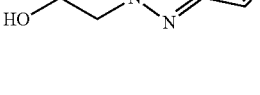 | 1.64 | 422.2 |
| 147 |  | 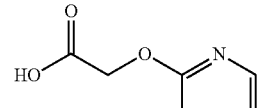 | 1.5 | 447.4 |
| 148 | 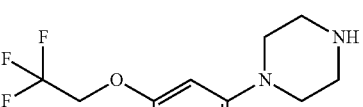 | 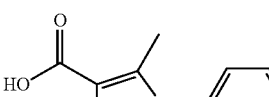 | 1.69 | 447.2 |
| 149 | | alternative route | 1.67 | 382.2 |
| 150 | | alternative route | 1.71 | 383.3 |
| 151 |  | 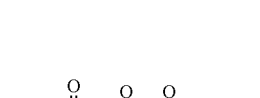 | 1.81 | 447.3 |
TABLE 1-9
| 152 | (R)-2-(4-fluorophenoxy)-1-(4-(6-isobutoxypyrimidin-4-yl)piperazin-1-yl)propan-1-one | |
| 153 | (R)-1-(4-(6-cyclobutoxypyrimidin-4-yl)piperazin-1-yl)-2-(4-fluorophenoxy)propan-1-one | |
| 154 | 2-(benzyloxy)-1-(4-(6-cyclobutoxypyrimidin-4-yl)piperazin-1-yl)ethanone | |

TABLE 1-9-continued

| 155 | 2-(3-fluorophenoxy)-1-(4-(6-(2,2,2-trifluoroethoxy)pyrimidin-4-yl)piperazin-1-yl)ethanone | 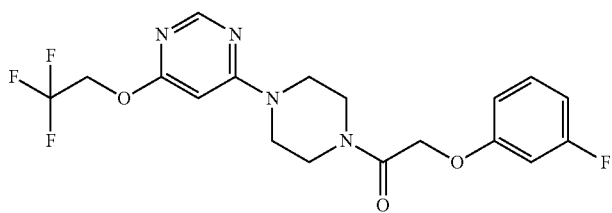 [SMILES: O=C(COc1cccc(F)c1)N1CCN(c2cc(OCC(F)(F)F)ncn2)CC1] |
| 156 | 2-(quinolin-8-yloxy)-1-(4-(6-(2,2,2-trifluoroethoxy)pyrimidin-4-yl)piperazin-1-yl)ethanone | 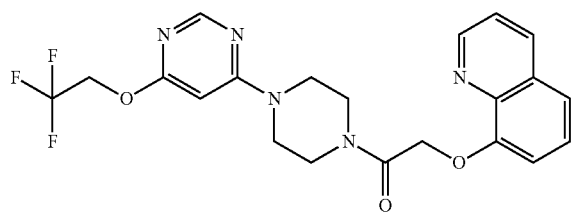 [SMILES: O=C(COc1cccc2cccnc12)N1CCN(c2cc(OCC(F)(F)F)ncn2)CC1] |
| 157 | 2-(2-oxo-2-(4-(6-(2,2,2-trifluoroethoxy)pyrimidin-4-yl)piperazin-1-yl)ethyl)-3,4-dihydroisoquinolin-1(2H)-one | 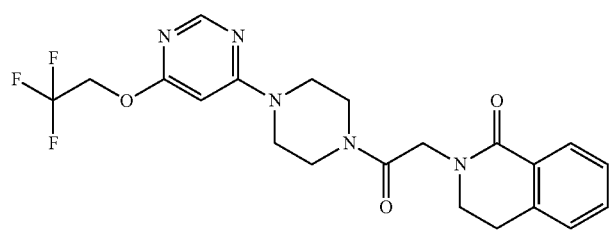 [SMILES: O=C(CN1CCc2ccccc2C1=O)N1CCN(c2cc(OCC(F)(F)F)ncn2)CC1] |
| 158 | 1-(2-oxo-2-(4-(6-(2,2,2-trifluoroethoxy)pyrimidin-4-yl)piperazin-1-yl)ethyl)-3,4-dihydroquinolin-2(1H)-one | 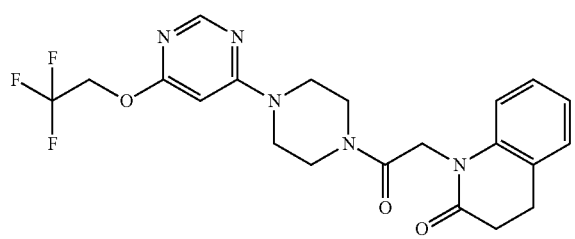 [SMILES: O=C(CN1C(=O)CCc2ccccc21)N1CCN(c2cc(OCC(F)(F)F)ncn2)CC1] |
| 159 | 2-(chroman-4-yloxy)-1-(4-(6-isobutoxypyrimidin-4-yl)piperazin-1-yl)ethanone | 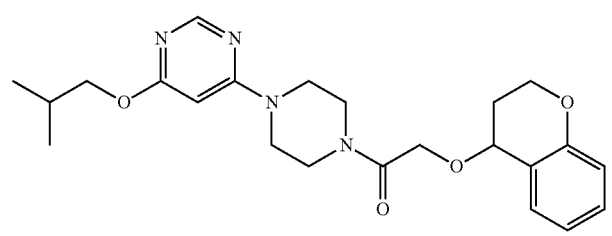 [SMILES: CC(C)COc1cc(N2CCN(C(=O)COC3CCOc4ccccc43)CC2)ncn1] |
| 160 | 1-(4-(6-isobutoxypyrimidin-4-yl)piperazin-1-yl)-2-(quinolin-2-yloxy)ethanone | 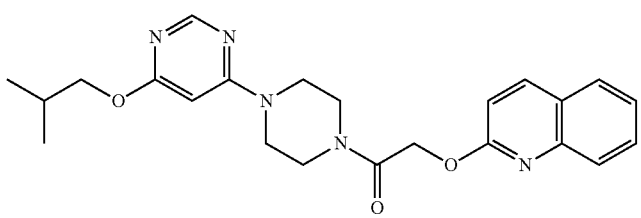 [SMILES: CC(C)COc1cc(N2CCN(C(=O)COc3ccc4ccccc4n3)CC2)ncn1] |
| 161 | 2-(chroman-4-yloxy)-1-(4-(6-(2,2,2-trifluoroethoxy)pyrimidin-4-yl)piperazin-1-yl)ethanone | 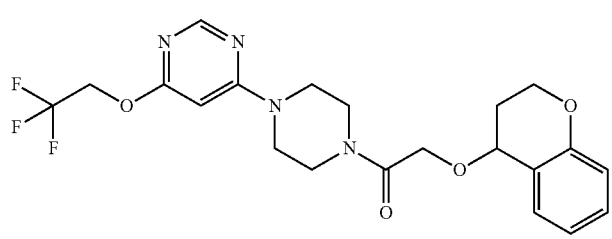 [SMILES: O=C(COC1CCOc2ccccc21)N1CCN(c2cc(OCC(F)(F)F)ncn2)CC1] |

TABLE 1-9-continued

| | | |
|---|---|---|
| 162 | 2-((1H-indol-4-yl)oxy)-1-(4-(6-(2,2,2-trifluoroethoxy)pyrimidin-4-yl)piperazin-1-yl)ethanone | 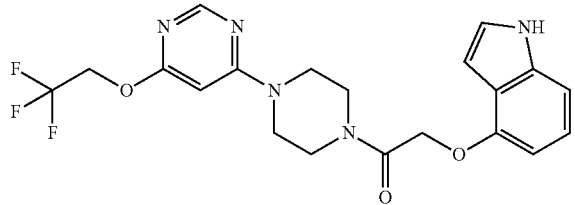 [SMILES: O=C(COc1cccc2[nH]ccc12)N1CCN(c2cc(OCC(F)(F)F)ncn2)CC1] |
| 163 | 1-(4-(6-isobutoxypyrimidin-4-yl)piperazin-1-yl)-2-phenylethane-1,2-dione | 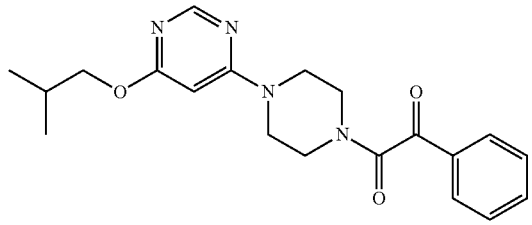 [SMILES: CC(C)COc1cc(N2CCN(C(=O)C(=O)c3ccccc3)CC2)ncn1] |
| 164 | (4-(6-isopropoxypyrimidin-4-yl)piperazin-1-yl)(1-methyl-3-phenyl-1H-pyrazol-5-yl)methanone | 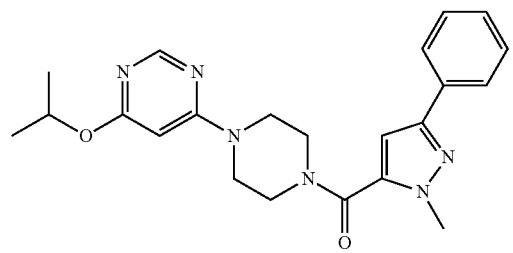 [SMILES: CC(C)Oc1cc(N2CCN(C(=O)c3cc(-c4ccccc4)nn3C)CC2)ncn1] |
| 165 | (4-(6-isopropoxypyrimidin-4-yl)piperazin-1-yl)(2-phenylthiazol-4-yl)methanone | 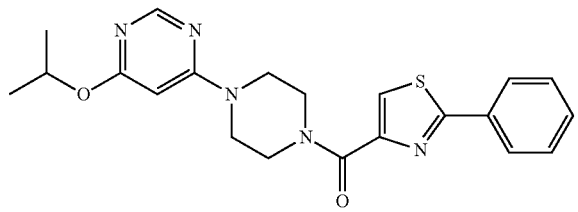 |
| 166 | (2-phenylthiazol-4-yl)(4-(6-(2,2,2-trifluoroethoxy)pyrimidin-4-yl)piperazin-1-yl)methanone | 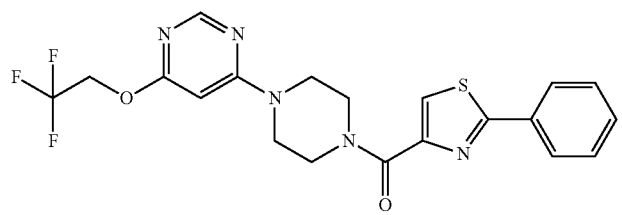 |
| 167 | (2-benzylthiazol-4-yl)(4-(6-isobutoxypyrimidin-4-yl)piperazin-1-yl)methanone | 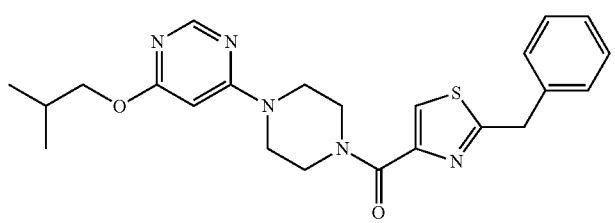 [SMILES: CC(C)COc1cc(N2CCN(C(=O)c3csc(Cc4ccccc4)n3)CC2)ncn1] |
| 168 | 2-((4-fluorobenzyl)oxy)-1-(4-(6-isobutoxypyrimidin-4-yl)piperazin-1-yl)ethanone | 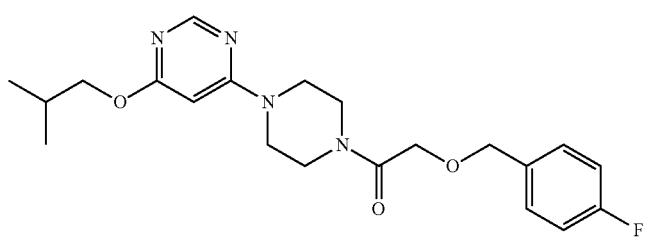 [SMILES: CC(C)COc1cc(N2CCN(C(=O)COCc3ccc(F)cc3)CC2)ncn1] |

TABLE 1-9-continued
| | | | | |
|---|---|---|---|---|
| 169 | (1-(4-fluorophenyl)-5-methyl-1H-pyrazol-4-yl)(4-(6-isobutoxypyrimidin-4-yl)piperazin-1-yl)methanone | 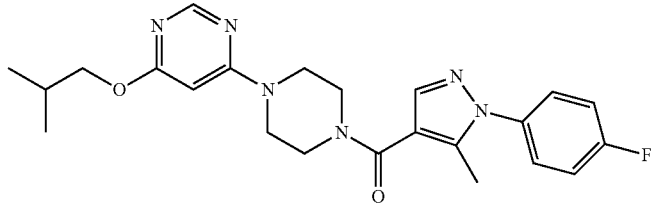 [SMILES: Cc1c(C(=O)N2CCN(c3cc(OCC(C)C)ncn3)CC2)cnn1-c1ccc(F)cc1] | | |
| 170 | (4-(6-isobutoxypyrimidin-4-yl)piperazin-1-yl)(1-(4-methoxyphenyl)-5-methyl-1H-pyrazol-4-yl)methanone | 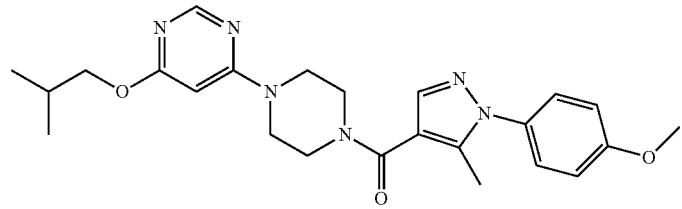 [SMILES: COc1ccc(-n2ncc(C(=O)N3CCN(c4cc(OCC(C)C)ncn4)CC3)c2C)cc1] | | |
| 152 | 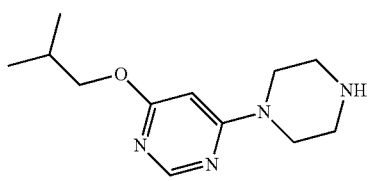 [SMILES: CC(C)COc1cc(N2CCNCC2)ncn1] | 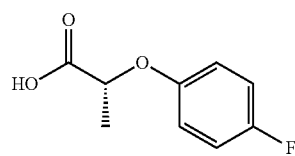 | 1.83 | 403.3 |
| 153 | 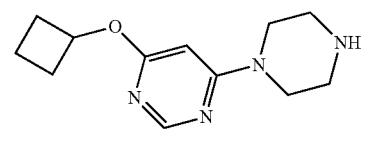 [SMILES: c1nc(OC2CCC2)cc(N2CCNCC2)n1] | 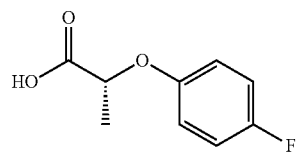 | 1.76 | 401.2 |
| 154 | 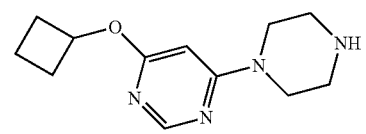 [SMILES: c1nc(OC2CCC2)cc(N2CCNCC2)n1] | 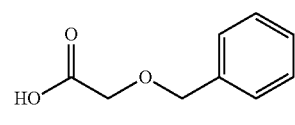 [SMILES: O=C(O)COCc1ccccc1] | 1.70 | 383.2 |
| 155 | 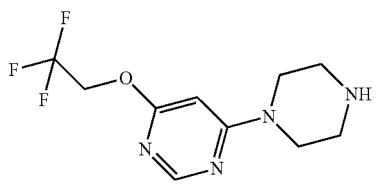 [SMILES: FC(F)(F)COc1cc(N2CCNCC2)ncn1] | 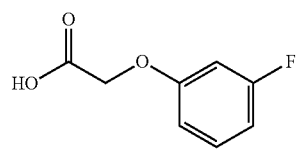 [SMILES: O=C(O)COc1cccc(F)c1] | 1.74 | 415.2 |
| 156 | 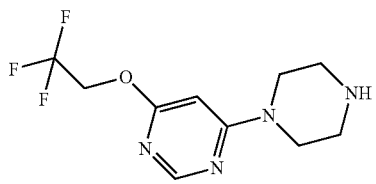 [SMILES: FC(F)(F)COc1cc(N2CCNCC2)ncn1] | 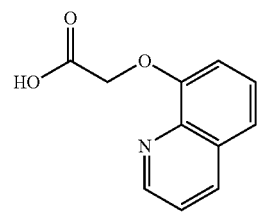 [SMILES: O=C(O)COc1cccc2cccnc12] | 1.59 | 448.2 |
| 157 | 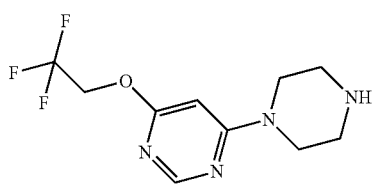 [SMILES: FC(F)(F)COc1cc(N2CCNCC2)ncn1] | 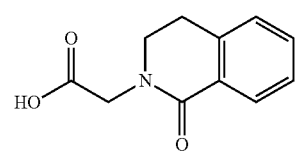 [SMILES: O=C(O)CN1CCc2ccccc2C1=O] | 1.60 | 450.2 |

TABLE 1-9-continued
| 158 | 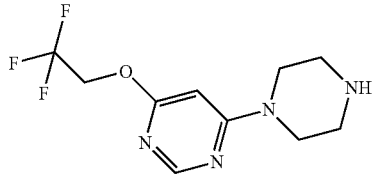 [SMILES: FC(F)(F)COc1cc(N2CCNCC2)ncn1] | 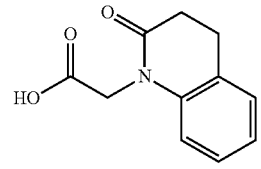 [SMILES: O=C(O)CN1C(=O)CCc2ccccc21] | 1.63 | 450.2 |
| 159 | 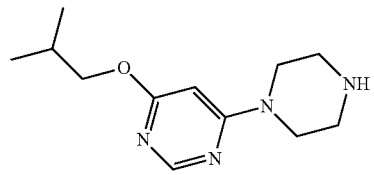 [SMILES: CC(C)COc1cc(N2CCNCC2)ncn1] | 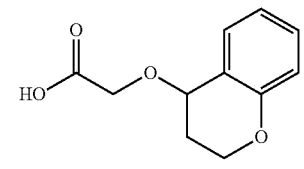 [SMILES: O=C(O)COC1CCOc2ccccc21] | 1.81 | 427.2 |
| 160 | 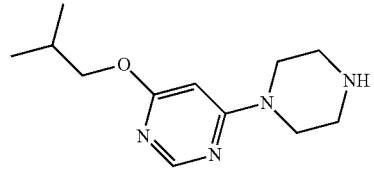 [SMILES: CC(C)COc1cc(N2CCNCC2)ncn1] | 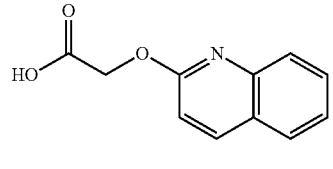 [SMILES: O=C(O)COc1ccc2ccccc2n1] | 1.85 | 422.2 |
| 161 | 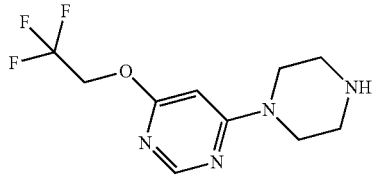 [SMILES: FC(F)(F)COc1cc(N2CCNCC2)ncn1] | 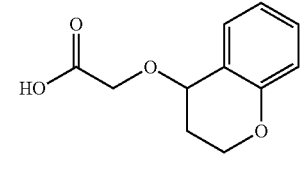 [SMILES: O=C(O)COC1CCOc2ccccc21] | 1.76 | 453.2 |
| 162 | 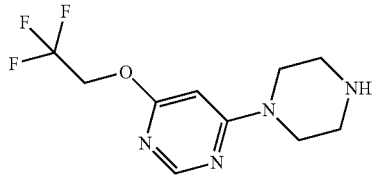 [SMILES: FC(F)(F)COc1cc(N2CCNCC2)ncn1] | 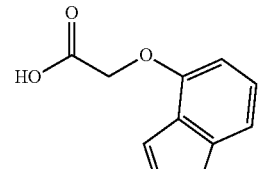 | 1.64 | 434.4 |
| 163 | 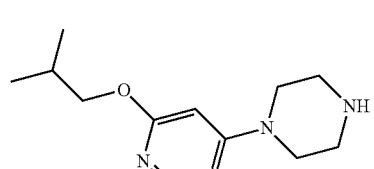 | 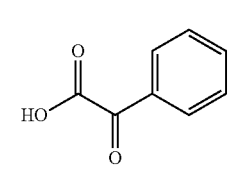 [SMILES: O=C(O)C(=O)c1ccccc1] | 1.81 | 369.2 |
| 164 | 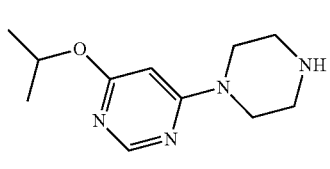 [SMILES: CC(C)Oc1cc(N2CCNCC2)ncn1] | 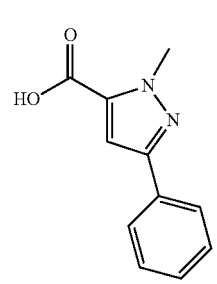 | 1.78 | 407.2 |
| 165 | 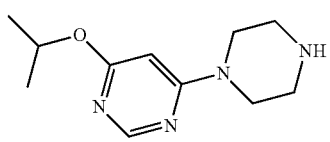 [SMILES: CC(C)Oc1cc(N2CCNCC2)ncn1] | 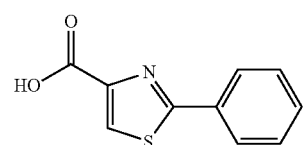 | 1.87 | 410.2 |

TABLE 1-9-continued
| | | | | | |
|---|---|---|---|---|---|
| 166 | 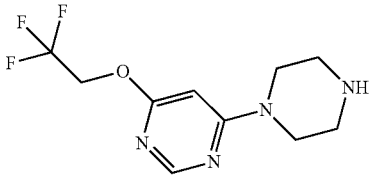 [SMILES: FC(F)(F)COc1cc(N2CCNCC2)ncn1] | | 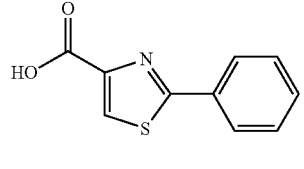 [SMILES: O=C(O)c1csc(-c2ccccc2)n1] | 1.90 | 450.1 |
| 167 | 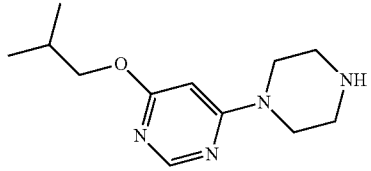 [SMILES: CC(C)COc1cc(N2CCNCC2)ncn1] | | 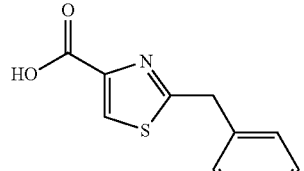 | 1.92 | 436.4 |
| 168 | 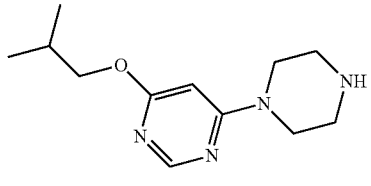 [SMILES: CC(C)COc1cc(N2CCNCC2)ncn1] | | 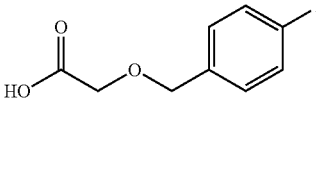 | 1.78 | 403.2 |
| 169 | 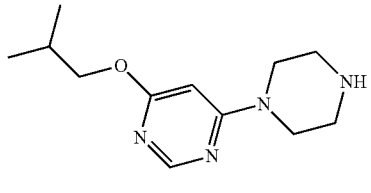 [SMILES: CC(C)COc1cc(N2CCNCC2)ncn1] | | 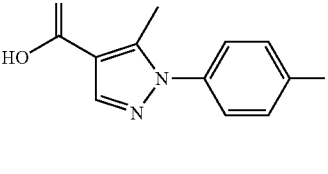 | 1.76 | 439.2 |
| 170 | 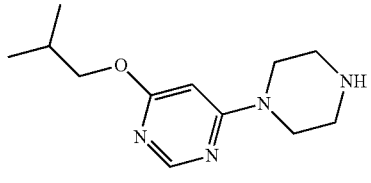 [SMILES: CC(C)COc1cc(N2CCNCC2)ncn1] | | 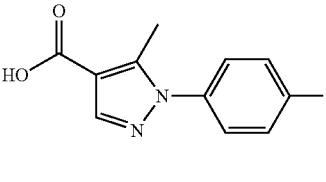 | 1.74 | 451.3 |

TABLE 1-10

| | | | | |
|---|---|---|---|---|
| 171 (1-benzyl-1H-pyrazol-4-yl)(4-(6-isobutoxypyrimidin-4-yl)piperazin-1-yl)methanone | | | 1.71 | 421.2 |
| 172 (4-(6-isobutoxypyrimidin-4-yl)piperazin-1-yl)(5-methyl-3-phenylisoxazol-4-yl)methanone | | | 1.84 | 422.2 |
| 173 (4-(6-isobutoxypyrimidin-4-yl)piperazin-1-yl)(3-methyl-5-phenylisoxazol-4-yl)methanone | | | 1.86 | 422.2 |

TABLE 1-10-continued

| | | | | |
|---|---|---|---|---|
| 174 (5-(2-fluorophenyl)oxazol-4-yl)(4-(6-isobutoxypyrimidin-4-yl)piperazin-1-yl)methanone | | | | 1.77 426.2 |
| 175 4-(6-isobutoxypyrimidin-4-yl)piperazin-1-yl)-(3-(2-methoxyphenyl)-1H-pyrazol-5-yl)methanone | | | | 1.76 435.4 |
| 176 2-((3-fluorophenyl)sulfonyl)-1-(4-(6-isobutoxypyrimidin-4-yl)piperazin-1-yl)ethanone | | | | 1.69 435.4 |
| 177 1-(4-(6-isobutoxypyrimidin-4-yl)piperazin-1-yl)-2-((3-methoxyphenyl)sulfonyl)ethanone | | | | 1.68 447.4 |

TABLE 1-10-continued

| # | Name | | | | Rt | m/z |
|---|---|---|---|---|---|---|
| 178 | 1-(4-(6-cyclobutoxypyrimidin-4-yl)piperazin-1-yl)-2-((3-fluorophenyl)sulfonyl)ethanone | | | | 1.61 | 433.3 |
| 179 | 1-(4-(6-cyclobutoxypyrimidin-4-yl)piperazin-1-yl)-2-((3-methoxyphenyl)sulfonyl)ethanone | | | | 1.61 | 445.4 |
| 180 | (2-((2-hydroxyethyl)thio)phenyl)(4-(6-isobutoxypyrimidin-4-yl)piperazin-1-yl)methanone | | | | 1.62 | 417.2 |
| 181 | (5-methyl-1-phenyl-1H-1,2,3-triazol-4-yl)(4-(6-(2,2,2-trifluoroethoxy)pyrimidin-4-yl)piperazin-1-yl)methanone | | | | 1.74 | 448.2 |
| 182 | (4-(6-isobutoxypyrimidin-4-yl)piperazin-1-yl)(5-methyl-2-phenyl-2H-1,2,3-triazol-4-yl)methanone | | | | 2.03 | 422.2 |

TABLE 1-10-continued
| | | | | |
|---|---|---|---|---|
| 183 (4-(6-isobutoxypyrimidin-4-yl)piperazin-1-yl)(1-(2-methoxyphenyl)-1H-pyrazol-4-yl)methanone | 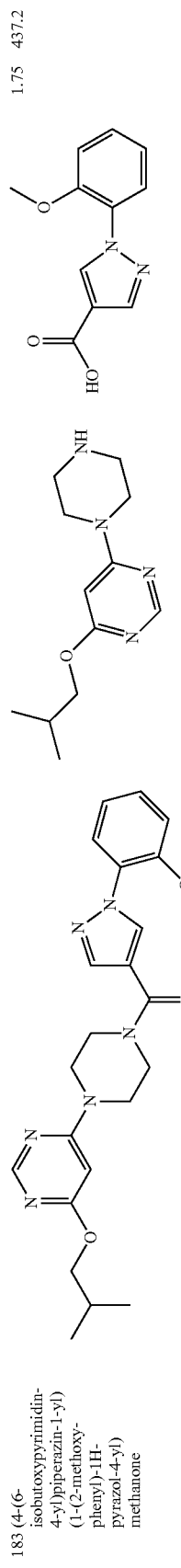 | | 1.75 | 437.2 |
| 184 (5-amino-1-phenyl-1H-pyrazol-4-yl)(4-(6-isobutoxypyrimidin-4-yl)piperazin-1-yl)methanone | 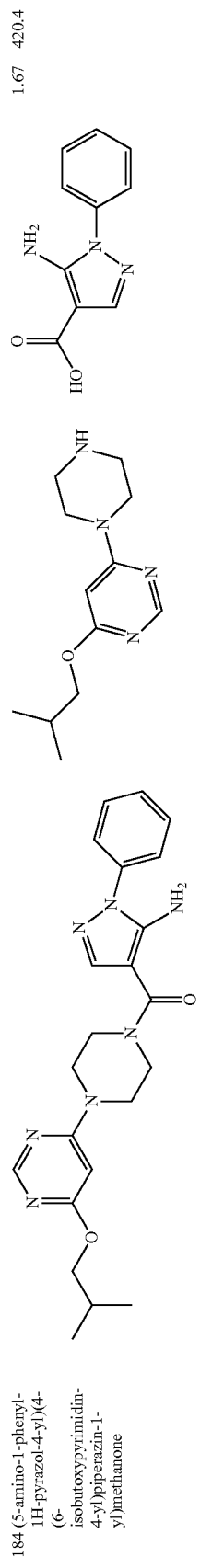 | | 1.67 | 420.4 |
| 185 (4-(6-isobutoxypyrimidin-4-yl)piperazin-1-yl)(6-phenylpyrimidin-4-yl)methanone | 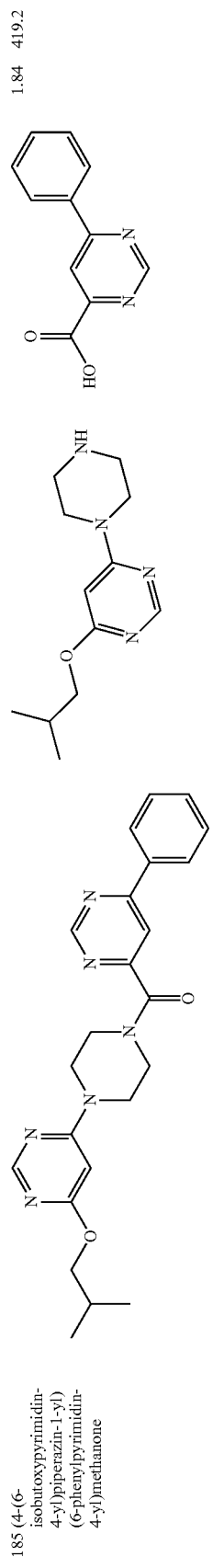 | | 1.84 | 419.2 |
| 186 (3-(1H-pyrazol-1-yl)phenyl)(4-(6-isobutoxypyrimidin-4-yl)piperazin-1-yl)methanone | 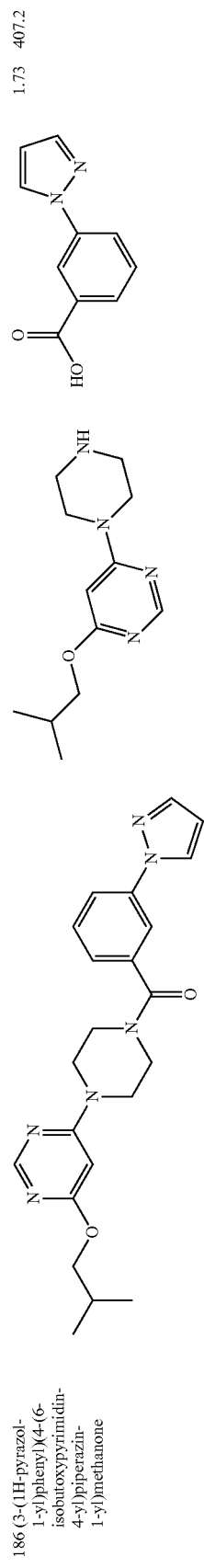 | | 1.73 | 407.2 |

TABLE 1-10-continued

| | | | | |
|---|---|---|---|---|
| 187 | (4-(6-isobutoxypyrimidin-4-yl)piperazin-1-yl)(3-(2-methylthiazol-4-yl)phenyl)methanone | | | 1.85  438.2 |
| 188 | (4-(6-isobutoxypyrimidin-4-yl)piperazin-1-yl)(3-(pyridin-3-yl)-1H-pyrazol-5-yl)methanone | | | 1.49  406.4 |
| 189 | (4-(6-isobutoxypyrimidin-4-yl)piperazin-1-yl)(1-methyl-3-(pyridin-3-yl)-1H-pyrazol-5-yl)methanone | | | 1.59  422.2 |

TABLE 1-11

| | | | | | |
|---|---|---|---|---|---|
| 190 (4-(6-isobutoxypyrimidin-4-yl)piperazin-1-yl)(2-(pyridin-3-yl)thiazol-4-yl)methanone | | | | 1.64 | 425.2 |
| 191 (4-(6-isobutoxypyrimidin-4-yl)piperazin-1-yl)(2-(pyridin-2-yl)thiazol-4-yl)methanone | | | | 1.80 | 425.2 |
| 192 (4-(6-isopropoxypyrimidin-4-yl)piperazin-1-yl)(2-(pyridin-3-yl)thiazol-4-yl)methanone | | | | 1.52 | 411.1 |
| 193 (4-(6-isopropoxypyrimidin-4-yl)piperazin-1-yl)(2-(pyridin-2-yl)thiazol-4-yl)methanone | | | | 1.69 | 411.2 |

TABLE 1-11-continued

| | | | | | |
|---|---|---|---|---|---|
| 194 (4-(6-iso-butoxypyrimidin-4-yl)piperazin-1-yl)(1-methyl-1H-pyrazolo[3,4-b]pyridin-3-yl)methanone | | | | 1.70 | 396.2 |
| 195 (1-methyl-1H-pyrazolo[3,4-b]pyridin-3-yl)(4-(6-(2,2,2-trifluoroethoxy)pyrimidin-4-yl)piperazin-1-yl)methanone | | | | 1.65 | 422.1 |
| 196 benzo[d][1,2,3]thiadiazol-7-yl(4-(6-isobutoxy-pyrimidin-4-yl)piperazin-1-yl)methanone | | | | 1.78 | 399.2 |
| 197 1-(4-(6-cyclobutoxypyrimidin-4-yl)piperazin-1-yl)-2-((1-methyl-1H-indol-4-yl)oxy)ethanone | | | | 1.74 | 422.2 |

| | | | | | |
|---|---|---|---|---|---|
| 198 | 1-(4-(6-isopropoxypyrimidin-4-yl)piperazin-1-yl)-2-((1-methyl-1H-indol-4-yl)oxy)ethanone | | | | 1.72 410.2 |
| 199 | (5-fluoro-1H-indazol-3-yl)(4-(6-isobutoxypyrimidin-4-yl)piperazin-1-yl)methanone | | | | 1.71 397.4 |
| 200 | (5-fluoro-1H-indazol-3-yl)(4-(6-isopropoxypyrimidin-4-yl)piperazin-1-yl)methanone | | | | 1.61 383.4 |
| 201 | (4-(6-cyclobutoxypyrimidin-4-yl)piperazin-1-yl)(5-fluoro-1H-indazol-3-yl)methanone | | | | 1.64 395.4 |

TABLE 1-11-continued
| | | | | | |
|---|---|---|---|---|---|
| 202 (1-(4-fluorophenyl)-5-methyl-1H-1,2,3-triazol-4-yl)(4-(6-isobutoxypyrimidin-4-yl)piperazin-1-yl)methanone | 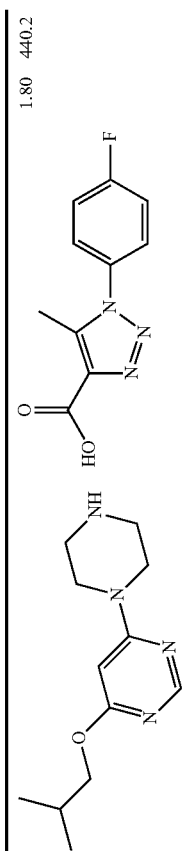 | | | 1.80 | 440.2 |
| 203 (1-(4-fluorophenyl)-5-methyl-1H-1,2,3-triazol-4-yl)(4-(6-isopropoxypyrimidin-4-yl)piperazin-1-yl)methanone | 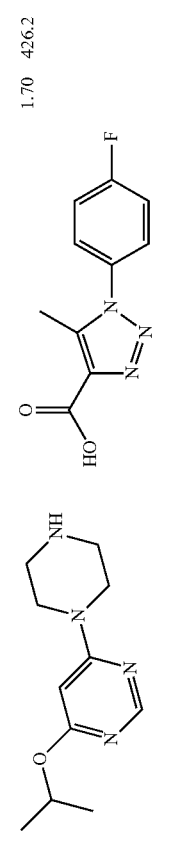 | | | 1.70 | 426.2 |
| 204 (4-(6-cyclobutoxypyrimidin-4-yl)piperazin-1-yl)(1-(4-fluorophenyl)-5-methyl-1H-1,2,3-triazol-4-yl)methanone | 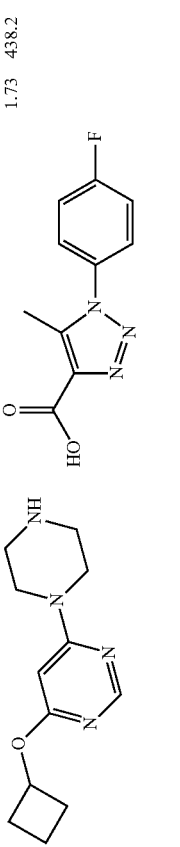 | | | 1.73 | 438.2 |
| 205 (1-(4-fluorophenyl)-5-methyl-1H-1,2,3-triazol-4-yl)(4-(6-(2,2,2-trifluoroethoxy)pyrimidin-4-yl)piperazin-1-yl)methanone | 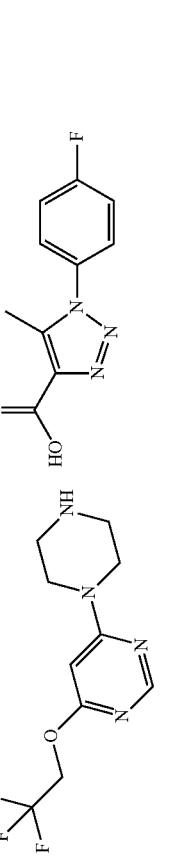 | | | 1.75 | 466.2 |

TABLE 1-11-continued

| | | | | |
|---|---|---|---|---|
| 206 (4-(6-iso-butoxypyrimidin-4-yl)piperazin-1-yl)(1-phenyl-1H-1,2,3-triazol-4-yl)methanone | [structure] | [structure] | [structure] | 1.79 408.2 |
| 207 (4-(6-isobutoxy-pyrimidin-4-yl)piperazin-1-yl)(3-(pyridin-2-yl)-1H-pyrazol-5-yl)methanone | [structure] | [structure] | [structure] | 1.57 406.4 |
| 208 (4-(6-iso-butoxypyrimidin-4-yl)piperazin-1-yl)(4-methyl-2-phenyloxazol-5-yl)methanone | [structure] | [structure] | [structure] | 1.92 422.2 |

TABLE 1-12
| | | | | |
|---|---|---|---|---|
| 209 (5-fluoro-1-methyl-1H-indazol-3-yl)(4-(6-isobutoxypyrimidin-4-yl)piperazin-1-yl)methanone | 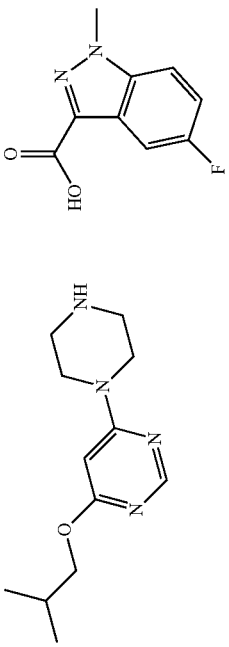 | 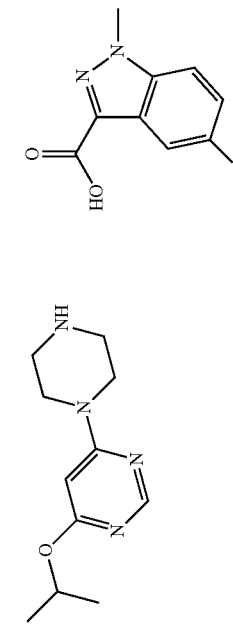 | 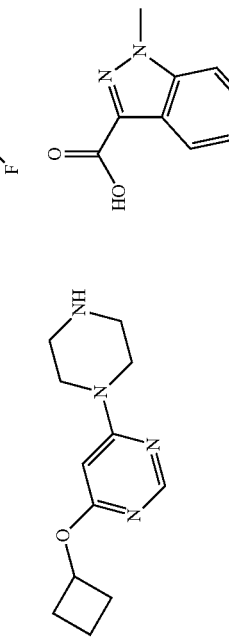 | 1.86 413.2 |
| 210 (5-fluoro-1-methyl-1H-indazol-3-yl)(4-(6-isopropoxypyrimidin-4-yl)piperazin-1-yl)methanone | | | | 1.75 399.2 |
| 211 (4-(6-cyclobutoxypyrimidin-4-yl)piperazin-1-yl)(5-fluoro-1-methyl-1H-indazol-3-yl)methanone | | | | 1.78 411.2 |
| 212 (5-fluoro-1-methyl-1H-indazol-3-yl)(4-(6-(2,2,2-trifluoroethoxy)pyrimidin-4-yl)piperazin-1-yl)methanone | | | | 1.80 439.1 |

TABLE 1-12-continued

| | | | | | |
|---|---|---|---|---|---|
| 213 (4-(6-isobutoxypyrimidin-4-yl)piperazin-1-yl)(2-phenylthiazol-4-yl)methanone | | | 1.97 | 424.2 |
| 214 (6-(1H-pyrazol-1-yl)pyridin-3-yl)(4-(6-isobutoxypyrimidin-4-yl)piperazin-1-yl)methanone | | | 1.72 | 408.1 |
| 215 (4-(6-isobutoxypyrimidin-4-yl)piperazin-1-yl)(1-phenyl-1H-pyrazol-4-yl)methanone | | | 1.76 | 405.4 |
| 216 (1-phenyl-1H-pyrazol-4-yl)(4-(6-(2,2,2-trifluoroethoxy)pyrimidin-4-yl)piperazin-1-yl)methanone | | | 1.72 | 431.2 |
| 217 (1-ethyl-3-(trifluoromethyl)-1H-pyrazol-5-yl)(4-(6-isobutoxypyrimidin-4-yl)piperazin-1-yl)methanone | | | 1.91 | 427.1 |

TABLE 1-12-continued

| | | | | | |
|---|---|---|---|---|---|
| 218 | (1-ethyl-3-(trifluoromethyl)-1H-pyrazol-5-yl)(4-(6-(2,2,2-trifluoroethoxy)pyrimidin-4-yl)piperazin-1-yl)methanone | | | 1.85 | 453 |
| 219 | (4-(6-cyclobutoxypyrimidin-4-yl)piperazin-1-yl)(5-methyl-1-phenyl-1H-1,2,3-triazol-4-yl)methanone | | | 1.71 | 420.1 |
| 220 | 2-(2H-benzo[d][1,2,3]triazol-2-yl)-1-(4-(6-cyclobutoxypyrimidin-4-yl)piperazin-1-yl)ethanone | | | 1.61 | 394.1 |
| 221 | benzo[c]isoxazol-3-yl(4-(6-isobutoxypyrimidin-4-yl)piperazin-1-yl)methanone | | | 1.84 | 382.1 |

TABLE 1-12-continued
| | | | | |
|---|---|---|---|---|
| 222 | (4-(6-isobutoxypyrimidin-4-yl)piperazin-1-yl)(4,5,6,7-tetrahydro-1H-indazol-3-yl)methanone | 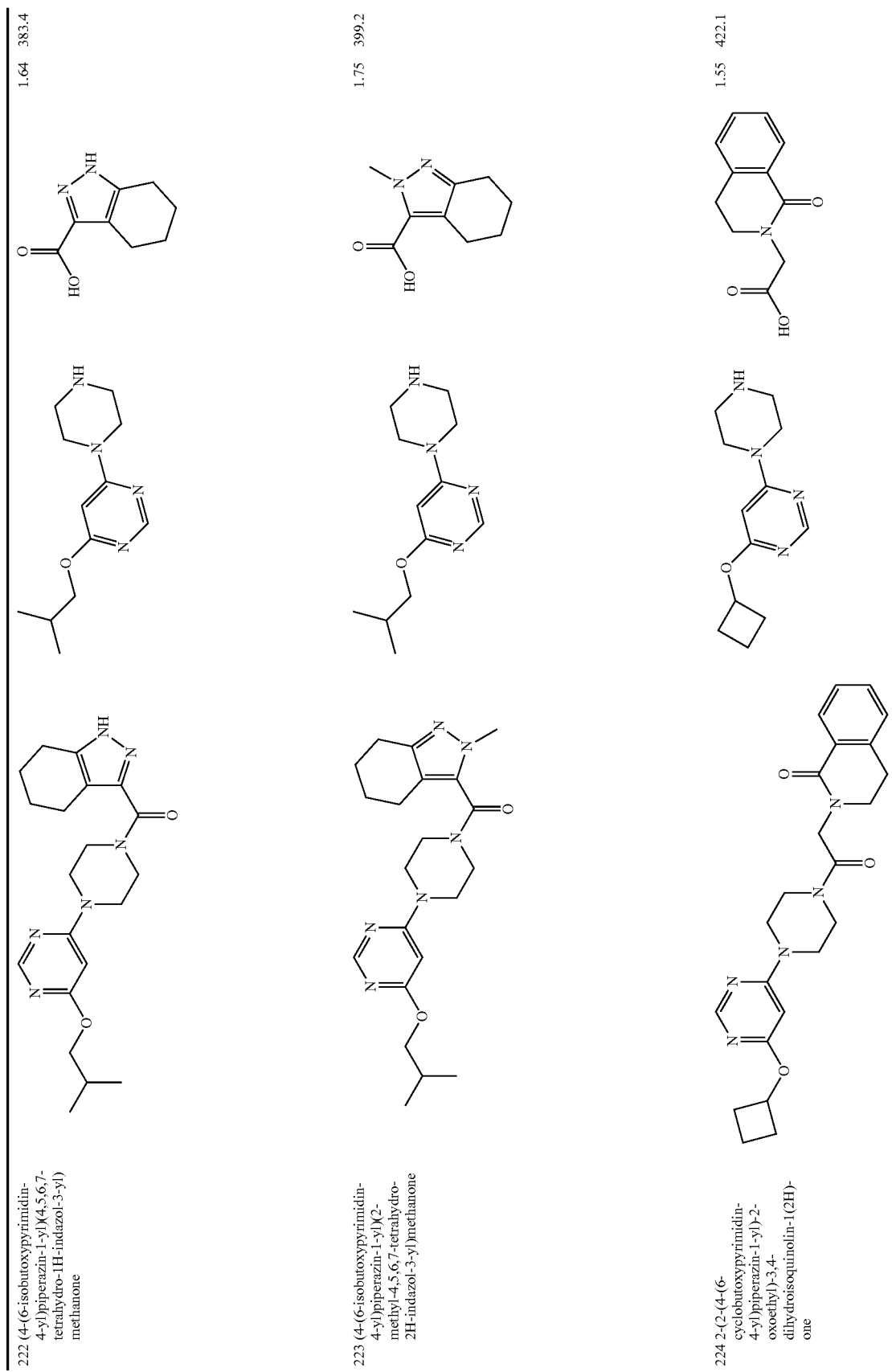 | | 1.64 383.4 |
| 223 | (4-(6-isobutoxypyrimidin-4-yl)piperazin-1-yl)(2-methyl-4,5,6,7-tetrahydro-2H-indazol-3-yl)methanone | | | 1.75 399.2 |
| 224 | 2-(2-(4-(6-cyclobutoxypyrimidin-4-yl)piperazin-1-yl)-2-oxoethyl)-3,4-dihydroisoquinolin-1(2H)-one | | | 1.55 422.1 |

TABLE 1-12-continued
| # | Name | Structure | Fragment | Acid | tR | m/z |
|---|---|---|---|---|---|---|
| 225 | (4-(6-cyclobutoxypyrimidin-4-yl)piperazin-1-yl)(1-methyl-1H-benzo[d]imidazol-2-yl)methanone | 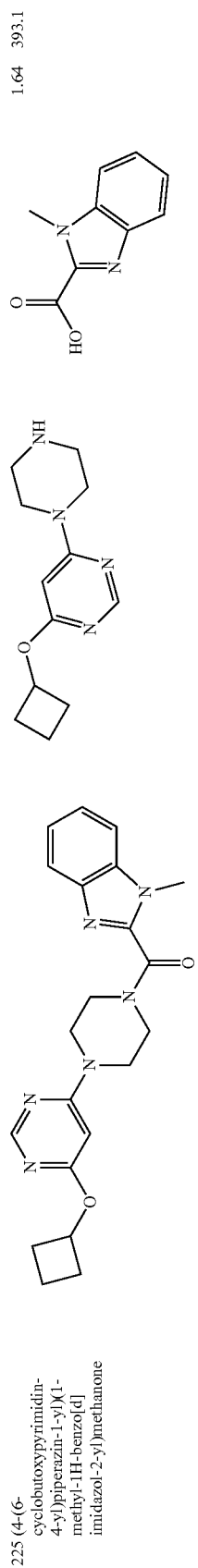 | | | 1.64 | 393.1 |
| 226 | (4-(6-isobutoxypyrimidin-4-yl)piperazin-1-yl)(5-(6-methoxypyridin-3-yl)-1-methyl-1H-pyrazol-3-yl)methanone | 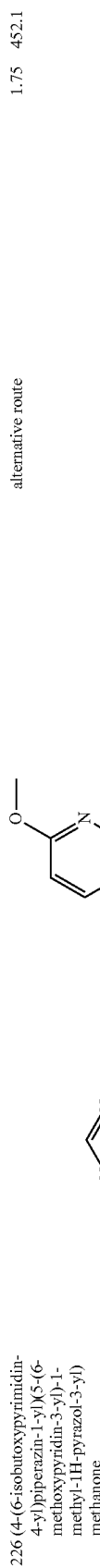 | alternative route | | 1.75 | 452.1 |
| 227 | (4-(6-cyclobutoxypyrimidin-4-yl)piperazin-1-yl)(pyrazolo[1,5-a]pyridin-2-yl)methanone | 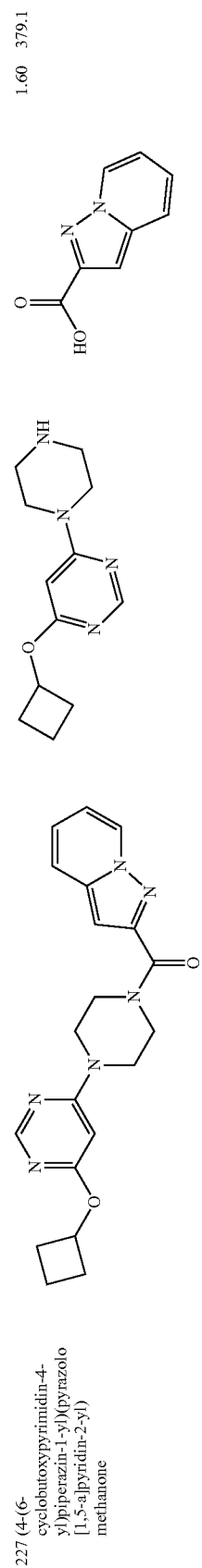 | | | 1.60 | 379.1 |

TABLE 1-13

| | | |
|---|---|---|
| 228 | (1-ethyl-5-(trifluoromethyl)-1H-pyrazol-3-yl)(4-(6-isobutoxypyrimidin-4-yl)piperazin-1-yl)methanone | 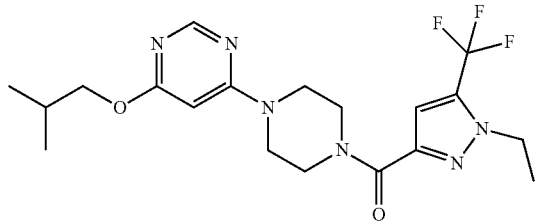 [SMILES: CCn1nc(C(=O)N2CCN(c3cc(OCC(C)C)ncn3)CC2)cc1C(F)(F)F] |
| 229 | (1-ethyl-5-(trifluoromethyl)-1H-pyrazol-3-yl)(4-(6-(2,2,2-trifluoroethoxy)pyrimidin-4-yl)piperazin-1-yl)methanone | 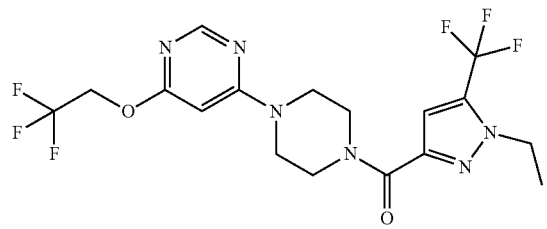 [SMILES: CCn1nc(C(=O)N2CCN(c3cc(OCC(F)(F)F)ncn3)CC2)cc1C(F)(F)F] |
| 230 | (4-(6-isobutoxypyrimidin-4-yl)piperazin-1-yl)(1-(pyridin-2-yl)-1H-pyrazol-4-yl)methanone | 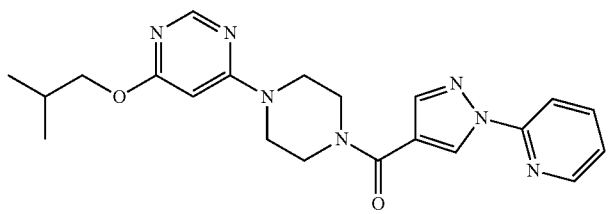 [SMILES: CC(C)COc1cc(N2CCN(C(=O)c3cnn(-c4ccccn4)c3)CC2)ncn1] |
| 231 | (6-ethoxypyridin-2-yl)(4-(6-isobutoxypyrimidn-4-yl)piperazin-1-yl)methanone | 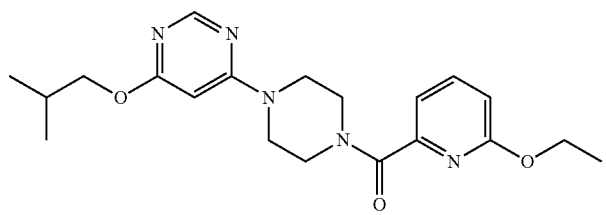 [SMILES: CCOc1cccc(C(=O)N2CCN(c3cc(OCC(C)C)ncn3)CC2)n1] |
| 232 | (4-(6-isobutoxypyrimidin-4-yl)piperazin-1-yl)(6-(2,2,2-trifluoroethoxy)pyridin-2-yl)methanone | 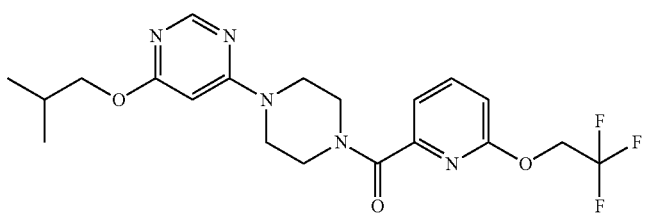 [SMILES: CC(C)COc1cc(N2CCN(C(=O)c3cccc(OCC(F)(F)F)n3)CC2)ncn1] |
| 233 | (4-(6-isobutoxypyrimidin-4-yl)piperazin-1-yl)(2-isopropylthiazol-4-yl)methanone | 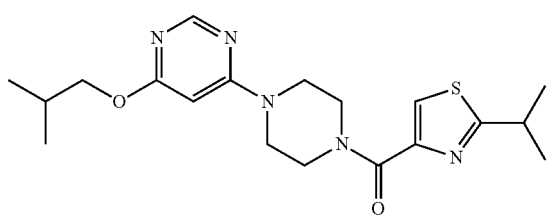 [SMILES: CC(C)COc1cc(N2CCN(C(=O)c3csc(C(C)C)n3)CC2)ncn1] |
| 234 | (3-cyclopropyl-1-methyl-1H-pyrazol-5-yl)(4-(6-isobutoxypyrimidin-4-yl)piperazin-1-yl)methanone | 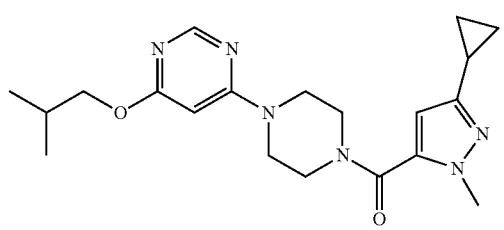 [SMILES: CC(C)COc1cc(N2CCN(C(=O)c3cc(C4CC4)nn3C)CC2)ncn1] |

TABLE 1-13-continued

| 235 | (5-cyclopropyl-1-methyl-1H-pyrazol-3-yl)(4-(6-isobutoxypyrimidin-4-yl)piperazin-1-yl)methanone | 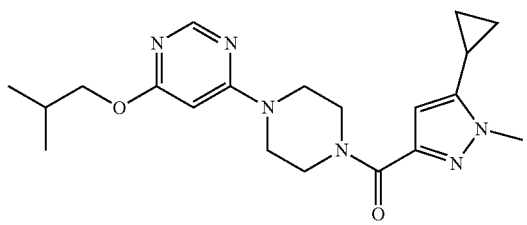 [SMILES: CC(C)COc1cc(N2CCN(C(=O)c3cc(C4CC4)n(C)n3)CC2)ncn1] |
| 236 | 2-(2-(4-(6-isobutoxypyrimidin-4-yl)piperazin-1-yl)-2-oxoethyl)isoquinolin-1(2H)-one | 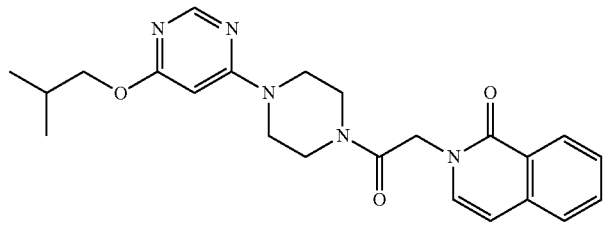 [SMILES: CC(C)COc1cc(N2CCN(C(=O)Cn3ccc4ccccc4c3=O)CC2)ncn1] |
| 237 | 2-(2-oxo-2-(4-(6-(2,2,2-trifluoroethoxy)pyrimidin-4-yl)piperazin-1-yl)ethyl)isoquinolin-1(2H)-one | 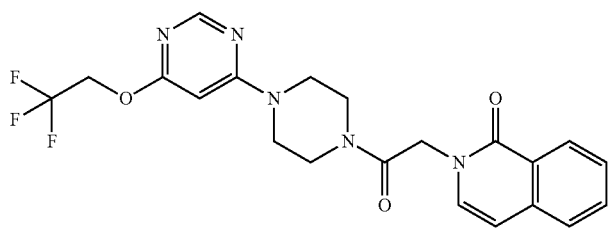 [SMILES: O=C(Cn1ccc2ccccc2c1=O)N1CCN(c2cc(OCC(F)(F)F)ncn2)CC1] |
| 238 | (4-(6-isobutoxypyrimidin-4-yl)piperazin-1-yl)(2-(trifluoromethyl)thiazol-4-yl)methanone | 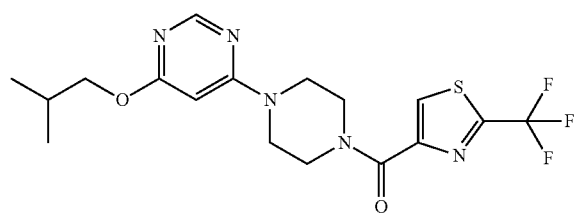 [SMILES: CC(C)COc1cc(N2CCN(C(=O)c3csc(C(F)(F)F)n3)CC2)ncn1] |
| 239 | (4-(6-(2,2,2-trifluoroethoxy)pyrimidin-4-yl)piperazin-1-yl)(2-(trifluoromethyl)thiazol-4-yl)methanone | 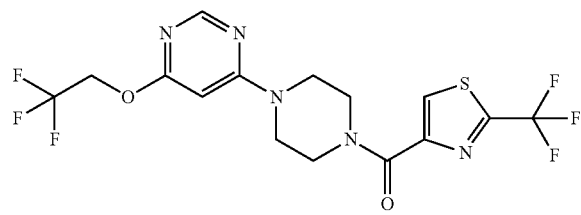 [SMILES: O=C(c1csc(C(F)(F)F)n1)N1CCN(c2cc(OCC(F)(F)F)ncn2)CC1] |
| 240 | 2-(2H-indazol-2-yl)-1-(4-(6-isobutoxypyrimidin-4-yl)piperazin-1-yl)ethanone | 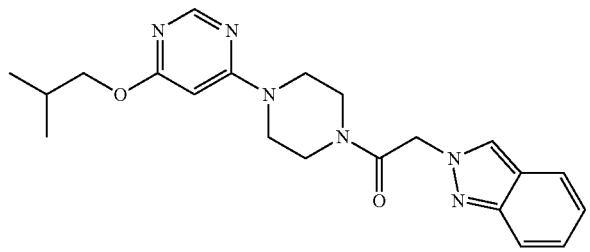 [SMILES: CC(C)COc1cc(N2CCN(C(=O)Cn3cc4ccccc4n3)CC2)ncn1] |
| 241 | (4-(6-ethoxypyrimidin-4-yl)piperazin-1-yl)(2-(pyridin-2-yl)thiazol-4-yl)methanone | 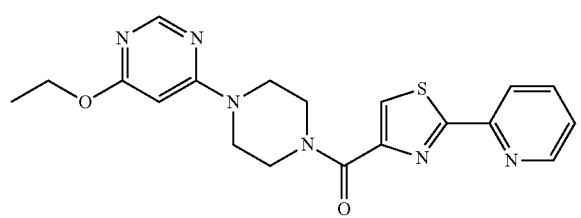 [SMILES: CCOc1cc(N2CCN(C(=O)c3csc(-c4ccccn4)n3)CC2)ncn1] |

TABLE 1-13-continued

| 242 | (5-(2-fluorophenyl)oxazol-4-yl)(4-(6-(2,2,2-trifluoroethoxy)pyrimidin-4-yl)piperazin-1-yl)methanone | 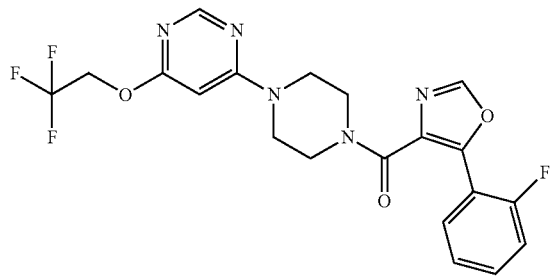 [SMILES: O=C(c1ncoc1-c1ccccc1F)N1CCN(c2cc(OCC(F)(F)F)ncn2)CC1] |
| 243 | (4-(6-(2,2,2-trifluoroethoxy)pyrimidin-4-yl)piperazin-1-yl)(1-(2-(trifluoromethyl)phenyl)-1H-imidazol-5-yl)methanone | 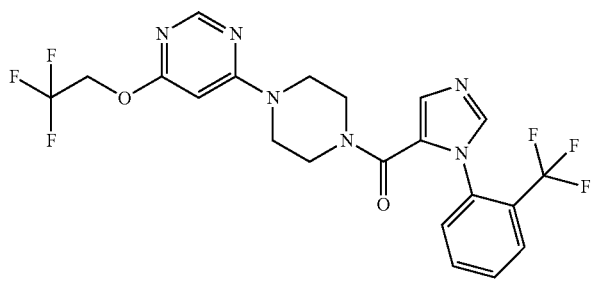 [SMILES: O=C(c1cncn1-c1ccccc1C(F)(F)F)N1CCN(c2cc(OCC(F)(F)F)ncn2)CC1] |
| 244 | (2-(pyridin-2-yl)thiazol-4-yl)(4-(6-(2,2,2-trifluoroethoxy)pyrimidin-4-yl)piperazin-1-yl)methanone | 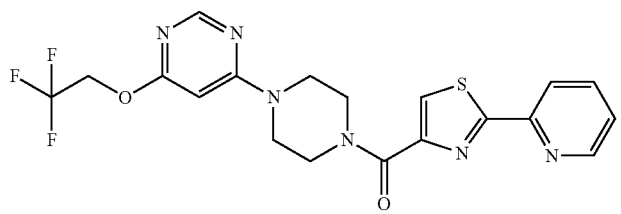 [SMILES: O=C(c1csc(-c2ccccn2)n1)N1CCN(c2cc(OCC(F)(F)F)ncn2)CC1] |
| 245 | (5-methyl-3-phenylisoxazol-4-yl)(4-(6-(2,2,2-trifluoroethoxy)pyrimidin-4-yl)piperazin-1-yl)methanone | 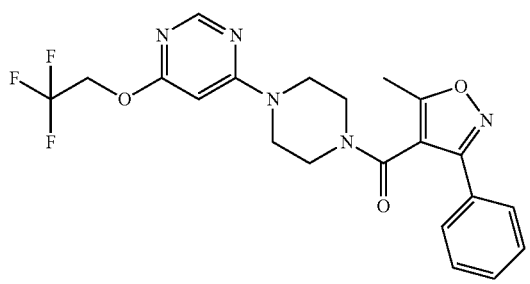 [SMILES: Cc1onc(-c2ccccc2)c1C(=O)N1CCN(c2cc(OCC(F)(F)F)ncn2)CC1] |
| 246 | (2-(1H-pyrazol-3-yl)phenyl)(4-(6-(2,2,2-trifluoroethoxy)pyrimidin-4-yl)piperazin-1-yl)methanone | 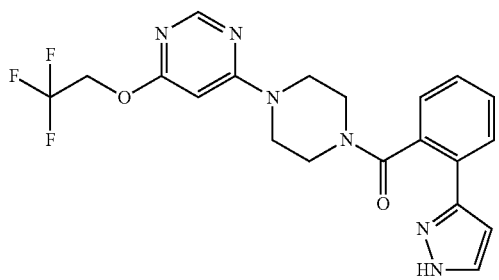 [SMILES: O=C(c1ccccc1-c1cc[nH]n1)N1CCN(c2cc(OCC(F)(F)F)ncn2)CC1] |

| 228 | 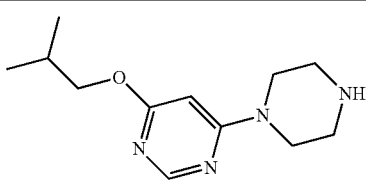 | 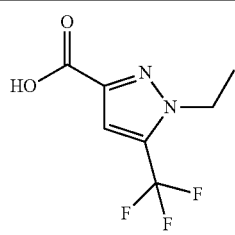 | 1.92 | 427.1 |

TABLE 1-13-continued
| | | | | |
|---|---|---|---|---|
| 229 | 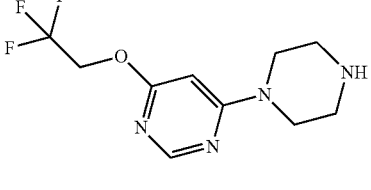 | 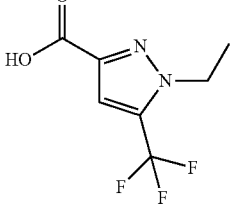 | 1.86 | 453 |
| 230 | 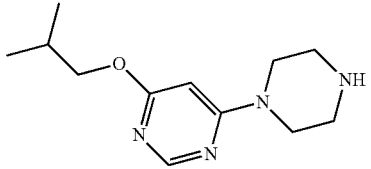 [SMILES: CC(C)COc1cc(N2CCNCC2)ncn1] | 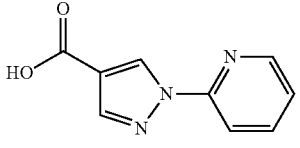 | 1.69 | 408.1 |
| 231 | 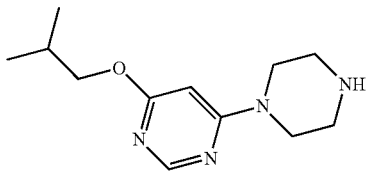 [SMILES: CC(C)COc1cc(N2CCNCC2)ncn1] | 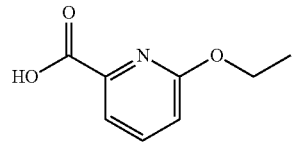 | 1.84 | 386.1 |
| 232 | 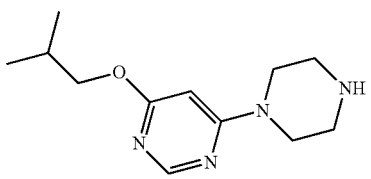 [SMILES: CC(C)COc1cc(N2CCNCC2)ncn1] | 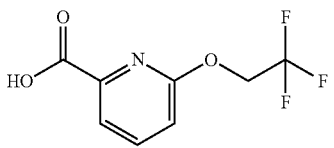 [SMILES: O=C(O)c1cccc(OCC(F)(F)F)n1] | 1.88 | 440.1 |
| 233 | 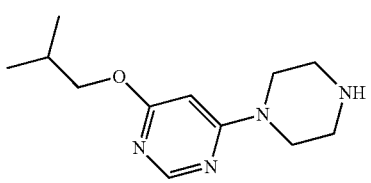 [SMILES: CC(C)COc1cc(N2CCNCC2)ncn1] | 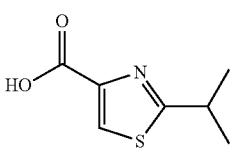 | 1.88 | 390.1 |
| 234 | 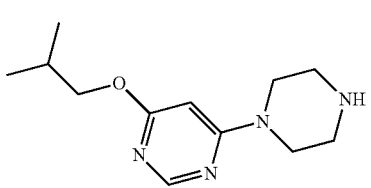 [SMILES: CC(C)COc1cc(N2CCNCC2)ncn1] | 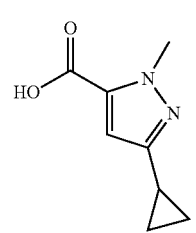 | 1.71 | 385.1 |
| 235 | 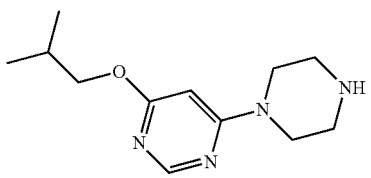 [SMILES: CC(C)COc1cc(N2CCNCC2)ncn1] | 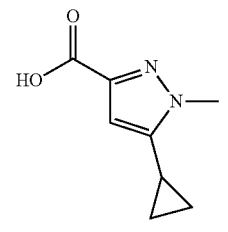 | 1.71 | 385.1 |
| 236 | 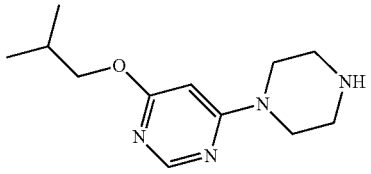 [SMILES: CC(C)COc1cc(N2CCNCC2)ncn1] | 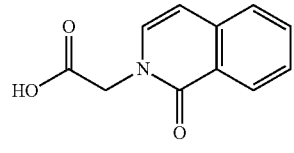 [SMILES: O=C(O)Cn1ccc2ccccc2c1=O] | 1.62 | 422.1 |

TABLE 1-13-continued
| | | | | |
|---|---|---|---|---|
| 237 | 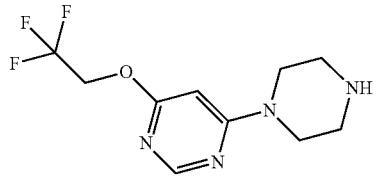 [SMILES: FC(F)(F)COc1cc(N2CCNCC2)ncn1] | 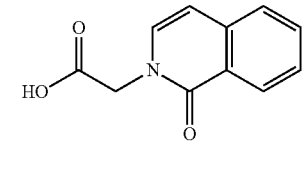 [SMILES: O=C(O)Cn1ccc2ccccc2c1=O] | 1.59 | 446.3 |
| 238 | 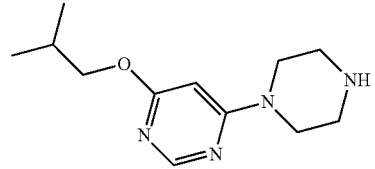 [SMILES: CC(C)COc1cc(N2CCNCC2)ncn1] | 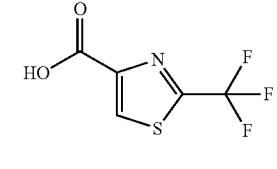 | 1.86 | 416 |
| 239 | 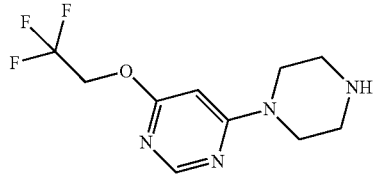 [SMILES: FC(F)(F)COc1cc(N2CCNCC2)ncn1] | 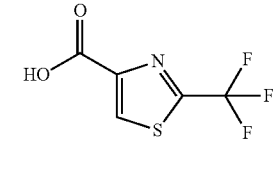 | 1.80 | 440.1 |
| 240 | 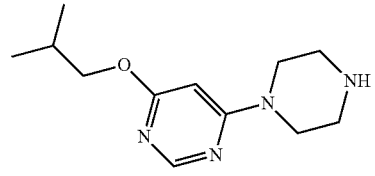 [SMILES: CC(C)COc1cc(N2CCNCC2)ncn1] | 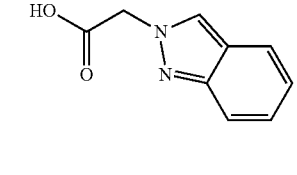 [SMILES: O=C(O)Cn1cc2ccccc2n1] | 1.63 | 393.4 |
| 241 | 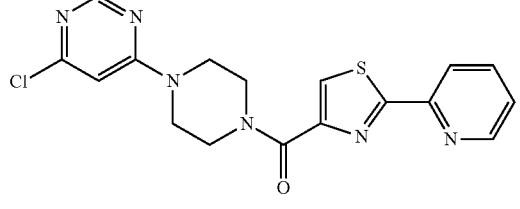 |  | 1.56 | 397 |
| 242 | 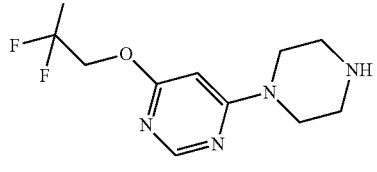 | 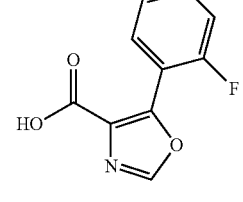 | 1.72 | 451.9 |
| 243 | 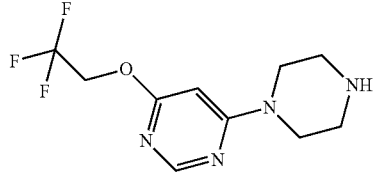 [SMILES: FC(F)(F)COc1cc(N2CCNCC2)ncn1] | 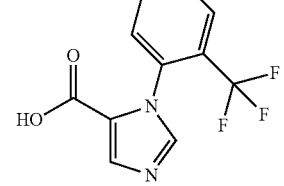 | 1.82 | 501 |
| 244 | 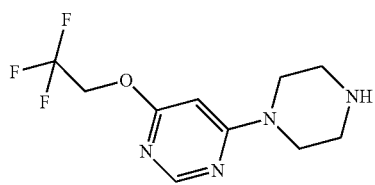 [SMILES: FC(F)(F)COc1cc(N2CCNCC2)ncn1] | 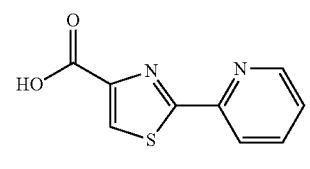 [SMILES: O=C(O)c1csc(-c2ccccn2)n1] | 1.74 | 450.9 |

TABLE 1-13-continued

| # | Structure | | value1 | value2 |
|---|---|---|---|---|
| 245 | 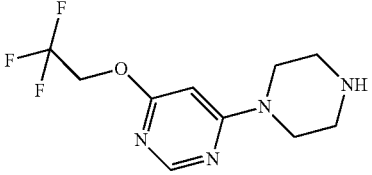 [SMILES: FC(F)(F)COc1cc(N2CCNCC2)ncn1] | | 1.78 | 446.3 |
| 246 | 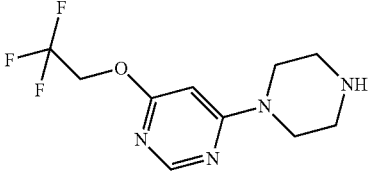 [SMILES: FC(F)(F)COc1cc(N2CCNCC2)ncn1] | | 1.56 | 431.2 |

FRET Assay

This screen was used to determine the effects of compounds on human $Na_{v1.3}$, human $Na_{v1.7}$, and human $Na_{v1.5}$ channels, utilising electrical field stimulation (EFS) system in 96-well plate format on FDSS (Hamamatsu Photonics) platform. The change of membrane potential was monitored with FRET dye pair, oxonol (DiSBAC2(3)) and coumarin (CC2-DMPE).

Cell Maintenance:

Each HEK293 cells expressing human $Na_{v1.3}$ channels and HEK293 cells expressing human $Na_{v1.5}$ channels were grown in T225 flasks, in a 5% $CO_2$ humidified incubator to about 80% confluence. Media composition consisted of Dulbecco's Modified Eagle Medium (high glucose), 10% FCS, 100 units/ml Penicillin, 100 microgram/ml Streptomycin and 500 microgram/ml Geneticine.

CHO cells expressing human $Na_{v1.7}$ channels were grown in T225 flasks, in a 5% $CO_2$ humidified incubator to about 80% confluence. Media composition consisted of HAM/F12 with Glutamax I, 10% FCS, 100 units/ml Penicillin and 100 microgram/ml Hygromycin.

Protocol:

Seeded each cell lines ($1 \times 10^5$ cells/well) into poly-D-lysine coated 96-well plates prior to experimentation.

Incubated at 37° C. in 5% $CO_2$ for 24 hours.

Washed each well with assay buffer (140 mM NaCl, 4.5 mM KCl, 10 mM D-Glucose, 2 mM $CaCl_2$, 1 mM $MgCl_2$, 10 mM HEPES, pH 7.4 adjusted with NaOH) twice.

Added 1st loading solution containing 10 microM CC2-DMPE and 0.06% Pluronic F-127 in assay buffer.

Incubated the plate at room temperature in dark for 1 hour.

Removed 1st loading solution and added 2nd loading solution containing 15 microM DiSBAC2(3), 0.555 mM VABSC-1 and 0.004% Pluronic F-127 in assay buffer.

Placed the plate under the dark at room temperature for 25 minutes.

Added compound solutions into the assay plate.

Set the assay plate in FDSS and placed an EFS device on the plate.

Measured EFS-induced fluorescent response by FDSS.

The data were analyzed and reported as normalized ratios of intensities measured at 440 nm. The process of calculating these ratios was performed as follows:

$FIR$ = Fluorescence Integration Ratio = the integral of the ratio normalized by baseline (before $EFS$) [Math. 1]

% inhibition =

$$\left\{ 1 - \frac{(FIR \text{ of each well} - \text{median } FIR \text{ in } 100\% \text{ } Inh.)}{(\text{median } FIR \text{ in } 0\% \text{ } Inh. - \text{median } FIR \text{ in } 100\% \text{ } Inh.)} \right\} \times 100$$

This analysis was performed using a computerized specific program designed for FDSS generated data. Fluorescence ratio values were plotted using XLfit to determine an $IC_{50}$ value for each compound.

All tested compounds showed less than about 5 microM of $IC_{50}$ against $Na_{v1.3}$ and/or $Na_{v1.7}$ in the above assays. Preferable compounds showed less than about 3 microM of $IC_{50}$ against $Na_{v1.3}$ and/or $Na_{v1.7}$ in the above assays. Compounds with $IC_{50}$ against $Na_{v1.3}$ <3 microM are:

Examples 5, 7, 9, 11, 14, 15, 16, 18, 22, 23, 24, 29, 30, 34, 38, 48, 52, 53, 57, 58, 59, 61, 62, 63, 68, 70, 73, 74, 77, 78, 82, 83, 85, 86, 89, 90, 91, 92, 93, 94, 96, 97, 98, 101, 105, 106, 107, 111, 119, 120, 121, 127, 128, 129, 131, 132, 133, 134, 135, 136, 139, 140, 141, 144, 145, 146, 148, 152, 155, 157, 164, 165, 167, 168, 169, 171, 182, 183, 184, 185, 187, 189, 190, 191, 193, 202, 203, 204, 205, 206, 208, 209, 210, 212, 213, 214, 215, 217, 219, 220, 228, 229, 231, 232, 233, 241, and 244.

Compounds with $IC_{50}$ against $Na_{v1.7}$ <3 microM are:

Examples 8, 10, 11, 15, 22, 24, 27, 28, 32, 39, 42, 43, 59, 60, 65, 70, 74, 75, 76, 77, 86, 89, 90, 100, 102, 105, 110, 120, 129, 131, 132, 133, 137, 139, 141, 143, 145, 146, 156, 160, 165, 166, 167, 168, 169, 175, 187, 208, 212, 213, 229, 236, 243, 244, and 245.

In addition, the ratio of activities against $Na_{v1.5}$ vs. $Na_{v1.3}$ or $Na_{v1.7}$ was more than three times.

INDUSTRIAL APPLICABILITY

The acyl piperazine derivatives of the present invention are useful in the treatment of a wide range of disorders, particularly pain, acute pain, chronic pain, neuropathic pain, inflammatory pain, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back and orofacial pain.

The invention claimed is:
1. A compound of the following formula (I):

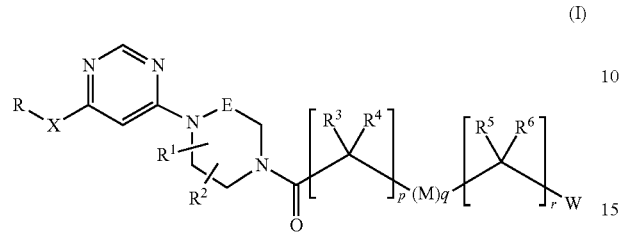

wherein
R is selected from the group consisting of: (1) $C_1$-$C_6$ alkyl and (2) $C_3$-$C_8$ cycloalkyl; which may be optionally substituted with 1 to 3 substituents independently selected from the group consisting of
(1) halogen, (2) $C_1$-$C_6$ alkyl, (3) $C_3$-$C_8$ cycloalkyl, (4) hydroxy, (5) $C_1$-$C_6$ alkoxy, (6) amino, (7) $C_1$-$C_6$ alkylamino, (8) di($C_1$-$C_6$ alkyl)amino, (9) hydroxy $C_1$-$C_6$ alkyl, (10) $C_1$-$C_6$ alkoxy $C_1$-$C_6$ alkyl, (11) $C_1$-$C_6$ alkylsulfonyl, (12) aminosulfonyl, (13) $C_1$-$C_6$ alkyl C(=O)—, (14) HO (O=)C—, (15) $C_1$-$C_6$ alkyl-O (O=)C—, (16) $R^A$N($R^B$)C(=O)—, (17) $C_1$-$C_6$ alkylsulfonylamino, (18) $R^A$C(=O)N($R^B$)—, (19) $NH_2$ (HN=)C—, and (20) 5 to 10 membered aryl $C_0$-$C_6$ alkyl; wherein said aryl may be optionally substituted with 1 to 5 substituents independently selected from the group consisting of hydroxy, halogen, $C_1$-$C_6$ alkyl, $C_1$-$C_6$ alkoxy, hydroxy $C_1$-$C_6$ alkyl, amino $C_1$-$C_6$ alkyl, $C_1$-$C_6$ haloalkyl, $C_1$-$C_6$ haloalkoxy, $C_3$-$C_8$ cycloalkyl, amino, $C_1$-$C_6$ alkylamino, di($C_1$-$C_6$ alkyl)amino, $C_1$-$C_6$ alkylthio, and nitro;
W is aryl which may be optionally substituted with 1 to 5 substituents independently selected from the group consisting of
(1) halogen, (2) $C_1$-$C_6$ alkyl, (3) $C_3$-$C_8$ cycloalkyl, (4) $C_1$-$C_6$ haloalkyl, (5) hydroxy, (6) $C_1$-$C_6$ alkoxy, (7) $C_1$-$C_6$ haloalkoxy, (8) $C_1$-$C_6$ alkylthio, (9) nitro, (10) amino, (11) $C_1$-$C_6$ alkylamino, (12) di($C_1$-$C_6$ alkyl) amino, (13) cyano, (14) hydroxy $C_1$-$C_6$ alkyl, (15) $C_1$-$C_6$ alkoxy $C_1$-$C_6$ alkyl, (16) $C_1$-$C_6$ alkylsulfonyl, (17) $R^A$N ($R^B$)$SO_2$—, (18) $C_1$-$C_6$ alkyl C(=O)—, (19) HO (O=) C—, (20) $C_1$-$C_6$alkyl-O (O=)C—, (21) $R^A$N($R^B$)C (=O)—, (22) $C_1$-$C_6$ alkylsulfonylamino, (23) $C_3$-$C_8$ cycloalkyl, (24) $R^A$C(=O)N($R^B$)—, (25) $NH_2$(HN=) C—, and (26) 5 to 10 membered aryl $C_0$-$C_6$ alkyl-$O_{0-1}$—; wherein said aryl may be optionally substituted with 1 to 5 substituents independently selected from the group consisting of hydroxy, halogen, $C_1$-$C_6$ alkyl, $C_1$-$C_6$ alkoxy, hydroxy $C_1$-$C_6$ alkyl, amino $C_1$-$C_6$ alkyl, $C_1$-$C_6$ haloalkyl, $C_1$-$C_6$ haloalkoxy, $C_3$-$C_8$ cycloalkyl $C_0$-$C_6$ alkyl, amino, $C_1$-$C_6$ alkylamino, di($C_1$-$C_6$ alkyl) amino, $C_1$-$C_6$ alkylthio, and nitro;
$R^A$ and $R^B$ are independently selected from the group consisting of:
(1) hydrogen, (2) $C_1$-$C_6$ alkyl, (3) hydroxy $C_1$-$C_6$ alkyl, (4) amino $C_1$-$C_6$ alkyl, (5) $C_1$-$C_6$ haloalkyl, (6) $C_1$-$C_6$ haloalkoxy, (7) $C_3$-$C_6$ alkenyl, (8) $C_3$-$C_8$ cycloalkyl $C_0$-$C_6$ alkyl, and (9) 5 to 10 membered aryl $C_0$-$C_6$ alkyl; wherein said aryl may be optionally substituted with 1 to 5 substituents independently selected from the group consisting of hydroxy, halogen, $C_1$-$C_6$ alkyl, $C_1$-$C_6$ alkoxy, hydroxy $C_1$-$C_6$ alkyl, amino $C_1$-$C_6$ alkyl, $C_1$-$C_6$ haloalkyl, $C_1$-$C_6$ haloalkoxy, $C_3$-$C_8$ cycloalkyl $C_0$-$C_6$ alkyl, amino, $C_1$-$C_6$ alkylamino, di($C_1$-$C_6$ alkyl)amino, $C_1$-$C_6$ alkylthio, and nitro;
$R^1$ and $R^2$ are independently selected from the group consisting of:
(1) hydrogen, (2) hydroxy $C_0$-$C_6$ alkyl, (3) halogen, (4) $C_1$-$C_6$ alkyl, (5) $C_3$-$C_8$ cycloalkyl, and (6) $C_1$-$C_6$ alkoxy;
or $R^1$ and $R^2$ taken together may form a 3 to 8 membered ring, where the ring may contain one to four heteroatom(s) independently selected from nitrogen, oxygen, and sulfur; and the ring may be substituted one or more substituents selected from $R^C$;
or $R^1$ and $R^2$ taken together may be an oxo group;
$R^C$ is selected from the group consisting of:
(1) hydrogen, (2) hydroxy $C_0$-$C_6$ alkyl, (3) halogen, (4) $C_1$-$C_6$ alkyl, (5) $C_3$-$C_8$ cycloalkyl, and (6) $C_1$-$C_6$ alkoxy;
$R^3$, $R^4$, $R^5$, and $R^6$ are each independently selected from the group consisting of:
(1) hydrogen, (2) hydroxy, (3) $C_1$-$C_6$ alkyl, (4) $C_3$-$C_8$ cycloalkyl, (5) $C_1$-$C_6$ alkoxy, (6) $R^A$N($R^B$)—, (7) $R^A$C (=O)N($R^B$)—, and (8) $R^A$O—C(=O)N($R^B$)—; or $R^3$ and $R^4$ together may be an oxo group; or $R^5$ and $R^6$ together may be an oxo group;
E is —CH$R^1$—, —CH$R^1$—$CH_2$—, —CO—$CH_2$—, or —CO—;
p is 0, 1, or 2; when p is one or more than one, $R^3$ and $R^4$ may be same or different;
q is 0, or 1;
r is 0, 1, or 2; when r is one or more than one, $R^5$ and $R^6$ may be same or different;
X is —O—, or —S—;
M is —O—, —$NR^A$—, —S—, —SO—, $SO_2$—, $NR^A$—$SO_2$—, or —$SO_2$—$NR^A$—;
or a pharmaceutically acceptable salt thereof.
2. The compound as claimed in claim 1 wherein
R is selected from the group consisting of: (1) $C_1$-$C_6$ alkyl and (2) $C_3$-$C_8$ cycloalkyl; which may be optionally substituted with 1 to 3 substituents independently selected from the group consisting of
(1) halogen, (2) $C_1$-$C_6$ alkyl, (3) $C_3$-$C_8$ cycloalkyl, (4) hydroxy, (5) $C_1$-$C_6$ alkoxy, (6) amino, (7) $C_1$-$C_6$ alkylamino, (8) di($C_1$-$C_6$ alkyl)amino, (9) hydroxy $C_1$-$C_6$ alkyl, (10) $C_1$-$C_6$ alkylsulfonyl, (11) aminosulfonyl, (12) $C_1$-$C_6$ alkyl C(=O)—, (13) $R^A$N($R^B$)C(=O)—, (14) $C_1$-$C_6$ alkylsulfonylamino, (15) $C_3$-$C_8$ cycloalkyl, (16) $R^A$C(=O)N($R^B$)—, and (17) 5 to 10 membered aryl $C_0$-$C_6$ alkyl; wherein said aryl may be optionally substituted with 1 to 5 substituents independently selected from the group consisting of hydroxy, halogen, $C_1$-$C_6$ alkyl, $C_1$-$C_6$ alkoxy, hydroxy $C_1$-$C_6$ alkyl, amino $C_1$-$C_6$ alkyl, $C_1$-$C_6$ haloalkyl, $C_1$-$C_6$ haloalkoxy, $C_3$-$C_8$ cycloalkyl, amino, $C_1$-$C_6$ alkylamino, di($C_1$-$C_6$ alkyl) amino, $C_1$-$C_6$ alkylthio, and nitro;
p is 0, 1, or 2; when p is one or more than one, $R^3$ and $R^4$ may be same or different;
q is 0, or 1; when p is 0, then q is 0;
X is —O—;
or a pharmaceutically acceptable salt thereof.
3. The compound as claimed in claim 1 wherein
R is selected from the group consisting of: (1) $C_1$-$C_6$ alkyl and (2) $C_3$-$C_8$ cycloalkyl; which may be optionally substituted with 1 to 3 substituents independently selected from the group consisting of
(1) halogen, (2) $C_1$-$C_6$ alkyl, (3) $C_3$-$C_8$ cycloalkyl, (4) hydroxy, (5) $C_1$-$C_6$ alkoxy, (6) amino, (7) $C_1$-$C_6$ alkylamino, (8) di(C$_1$-C$_6$ alkyl)amino, (9) hydroxy C$_1$-C$_6$ alkyl, and (10) 5 to 10 membered aryl C$_0$-C$_6$ alkyl; wherein said aryl may be optionally substituted with 1 to 5 substituents independently selected from the group consisting of hydroxy, halogen, C$_1$-C$_6$ alkyl, C$_1$-C$_6$ alkoxy, hydroxy C$_1$-C$_6$ alkyl, amino C$_1$-C$_6$ alkyl, C$_1$-C$_6$ haloalkyl, C$_1$-C$_6$ haloalkoxy, C$_3$-C$_8$ cycloalkyl, amino, C$_1$-C$_6$ alkylamino, di(C$_1$-C$_6$ alkyl)amino, C$_1$-C$_6$ alkylthio, and nitro;

or a pharmaceutically acceptable salt thereof.

4. The compound as claimed in claim 1, which is selected from:

- (3-fluoro-4-methylphenyl)(4-(6-isobutoxypyrimidin-4-yl)piperazin-1-yl)methanone;
- (4-(6-((1,3-dimethyl-1H-pyrazol-5-yl)methoxy)pyrimidin-4-yl)piperazin-1-yl)(3-fluoro-4-methylphenyl)methanone;
- (R)-2-hydroxy-1-(4-(6-isobutoxypyrimidin-4-yl)piperazin-1-yl)-2-phenylethanone;
- (S)-2-hydroxy-1-(4-(6-isobutoxypyrimidin-4-yl)piperazin-1-yl)-3-phenylpropan-1-one;
- (R)-2-hydroxy-1-(4-(6-isobutoxypyrimidin-4-yl)piperazin-1-yl)-3-phenylpropan-1-one;
- (4-(6-(cyclopropylmethoxy)pyrimidin-4-yl)piperazin-1-yl)(3-fluoro-4-methylphenyl)methanone;
- (4-(6-(cyclopentyloxy)pyrimidin-4-yl)piperazin-1-yl)(3-fluoro-4-methylphenyl)methanone;
- (3-fluoro-4-methylphenyl)(4-(6-(2,2,2-trifluoroethoxyl)pyrimidin-4-yl)piperazin-1-yl)methanone;
- (1H-indol-4-yl)(4-(6-isobutoxypyrimidin-4-yl)piperazin-1-yl)methanone;
- (S)-tert-butyl (2-(4-(6-isobutoxypyrimidin-4-yl)piperazin-1-yl)-2-oxo-1-phenylethyl)carbamate;
- (R)-tert-butyl (2-(4-(6-isobutoxypyrimidin-4-yl)piperazin-1-yl)-2-oxo-1-phenylethyl)carbamate;
- (3-fluoro-4-methylphenyl)(4-(6-(isobutylamino)pyrimidin-4-yl)piperazin-1-yl)methanone;
- (4-(6-isobutoxypyrimidin-4-yl)piperazin-1-yl)(6-methoxypyridin-2-yl)methanone;
- (4-(6-isobutoxypyrimidin-4-yl)piperazin-1-yl)(1-methyl-3-(trifluoromethyl)-1H-pyrazol-5-yl)methanone;
- (4-(6-isobutoxypyrimidin-4-yl)piperazin-1-yl)(3-(trifluoromethoxy)phenyl)methanone;
- (4-(6-cyclobutoxypyrimidin-4-yl)piperazin-1-yl)(3-fluoro-4-methylphenyl)methanone;
- 4-(3-fluoro-4-methylbenzoyl)-1-(6-isobutoxypyrimidin-4-yl)piperazin-2-one;
- (4-(6-isobutoxypyrimidin-4-yl)piperazin-1-yl)(quinolin-2-yl)methanone;
- (4-fluorophenyl)(4-(6-isobutoxypyrimidin-4-yl)piperazin-1-yl)methanone;
- (4-(6-isobutoxypyrimidin-4-yl)piperazin-1-yl)(1-methyl-5-(trifluoromethyl)-1H-pyrazol-3-yl)methanone;
- (4-(6-isobutoxypyrimidin-4-yl)piperazin-1-yl)(2-methyl-2H-indazol-3-yl)methanone;
- (4-(6-isobutoxypyrimidin-4-yl)piperazin-1-yl)(1-methyl-1H-indazol-3-yl)methanone;
- (4-(6-isobutoxypyrimidin-4-yl)piperazin-1-yl)(1-methyl-1H-benzo[d]imidazol-2-yl)methanone;
- 2-(4-fluorophenoxy)-1-(4-(6-isobutoxypyrimidin-4-yl)piperazin-1-yl)ethanone;
- (4-chloro-2-hydroxyphenyl)(4-(6-isobutoxypyrimidin-4-yl)piperazin-1-yl)methanone;
- 2-(2-(4-(6-isobutoxypyrimidin-4-yl)piperazin-1-yl)-2-oxoethyl)isoindolin-1-one;
- (S)-2-amino-1-(4-(6-isobutoxypyrimidin-4-yl)piperazin-1-yl)-2-phenylethanone;
- (R)-2-amino-1-(4-(6-isobutoxypyrimidin-4-yl)piperazin-1-yl)-2-phenylethanone;
- (1-methyl-5-(trifluoromethyl)-1H-pyrazol-3-yl)(4-(6-(2,2,2-trifluoroethoxyl)pyrimidin-4-yl)piperazin-1-yl)methanone;
- (1-methyl-1H-indazol-3-yl)(4-(6-(2,2,2-trifluoroethoxyl)pyrimidin-4-yl)piperazin-1-yl)methanone;
- (4-(6-isobutoxypyrimidin-4-yl)piperazin-1-yl)(quinolin-3-yl)methanone;
- (8-hydroxyquinolin-2-yl)(4-(6-isobutoxypyrimidin-4-yl)piperazin-1-yl)methanone;
- (1H-indazol-3-yl)(4-(6-isobutoxypyrimidin-4-yl)piperazin-1-yl)methanone;
- (4-(6-isobutoxypyrimidin-4-yl)piperazin-1-yl)(quinoxalin-2-yl)methanone;
- (4-(6-isobutoxypyrimidin-4-yl)piperazin-1-yl)(isoquinolin-3-yl)methanone;
- (4-(6-isobutoxypyrimidin-4-yl)piperazin-1-yl)(4-methoxyquinolin-2-yl)methanone;
- (4-(6-cyclobutoxypyrimidin-4-yl)piperazin-1-yl)(quinolin-2-yl)methanone;
- (4-(6-cyclobutoxypyrimidin-4-yl)piperazin-1-yl)(1-methyl-1H-indazol-3-yl)methanone;
- (4-chloro-3-fluorophenyl)(4-(6-isobutoxypyrimidin-4-yl)piperazin-1-yl)methanone;
- (4-fluoro-3-methylphenyl)(4-(6-isobutoxypyrimidin-4-yl)piperazin-1-yl)methanone;
- (4-(6-isobutoxypyrimidin-4-yl)piperazin-1-yl)(pyrazolo[1,5-a]pyridin-2-yl)methanone;
- (2-hydroxy-4-(trifluoromethyl)phenyl)(4-(6-isobutoxypyrimidin-4-yl)piperazin-1-yl)methanone;
- (4-(6-isobutoxypyrimidin-4-yl)piperazin-1-yl)(1-methyl-1H-indol-2-yl)methanone;
- (1-(2-hydroxyethyl)-1H-indazol-3-yl)(4-(6-isobutoxypyrimidin-4-yl)piperazin-1-yl)methanone;
- 1-(4-(6-isobutoxypyrimidin-4-yl)piperazin-1-yl)-2-phenoxyethanone;
- (R)-1-(4-(6-isobutoxypyrimidin-4-yl)piperazin-1-yl)-2-phenoxypropan-1-one;
- 1-(4-(6-isobutoxypyrimidin-4-yl)piperazin-1-yl)-2-((6-(trifluoromethyl)pyridin-3-yl)oxy)ethanone;
- 2-(4-fluorophenoxy)-1-(4-(6-isobutoxypyrimidin-4-yl)piperazin-1-yl)propan-1-one;
- (2,3-dihydrobenzofuran-2-yl)(4-(6-isobutoxypyrimidin-4-yl)piperazin-1-yl)methanone;
- 2-(4-fluorophenoxy)-1-(4-(6-(2,2,2-trifluoroethoxyl)pyrimidin-4-yl)piperazin-1-yl)ethanone;
- 1-(4-(6-cyclobutoxypyrimidin-4-yl)piperazin-1-yl)-2-(4-fluorophenoxyl)ethanone;
- (4-(6-isobutoxypyrimidin-4-yl)piperazin-1-yl)(6-(pyrrolidin-1-yl)pyridin-2-yl)methanone;
- benzyl 4-(6-isobutoxypyrimidin-4-yl)piperazine-1-carboxylate;
- (4-(6-isobutoxypyrimidin-4-yl)piperazin-1-yl)(3-(trifluoromethyl)-1H-pyrazol-5-yl)methanone;
- quinolin-2-yl(4-(6-(2,2,2-trifluoroethoxyl)pyrimidin-4-yl)piperazin-1-yl)methanone;
- (4-(6-cyclobutoxypyrimidin-4-yl)piperazin-1-yl)(4-fluorophenyl)methanone;
- 4-(2-(4-(6-isobutoxypyrimidin-4-yl)piperazin-1-yl)-2-oxoethyl)-2H-benzo[b][1,4]oxazin-3(4H)-one;
- 2-(benzo[d]isoxazol-3-yl)-1-(4-(6-isobutoxypyrimidin-4-yl)piperazin-1-yl)ethanone;
- 3-(1H-indol-1-yl)-1-(4-(6-isobutoxypyrimidin-4-yl)piperazin-1-yl)propan-1-one;
- 2-(5-fluoro-1H-indol-3-yl)-1-(4-(6-isobutoxypyrimidin-4-yl)piperazin-1-yl)ethanone;

2-(3-(4-(6-isobutoxypyrimidin-4-yl)piperazin-1-yl)-3-oxopropyl)isoindolin-1-one;
(4-(6-isobutoxypyrimidin-4-yl)piperazin-1-yl)(1-(2-methoxyethyl)-1H-indol-2-yl)methanone;
(4-methoxyquinolin-2-yl)(4-(6-(2,2,2-trifluoroethoxyl)pyrimidin-4-yl)piperazin-1-yl)methanone;
quinoxalin-2-yl(4-(6-(2,2,2-trifluoroethoxyl)pyrimidin-4-yl)piperazin-1-yl)methanone;
(8-hydroxyquinolin-2-yl)(4-(6-(2,2,2-trifluoroethoxyl)pyrimidin-4-yl)piperazin-1-yl)methanone;
(1H-indol-4-yl)(4-(6-(2,2,2-trifluoroethoxyl)pyrimidin-4-yl)piperazin-1-yl)methanone;
(2-methyl-2H-indazol-3-yl)(4-(6-(2,2,2-trifluoroethoxyl)pyrimidin-4-yl)piperazin-1-yl)methanone;
(1H-indazol-3-yl)(4-(6-(2,2,2-trifluoroethoxyl)pyrimidin-4-yl)piperazin-1-yl)methanone;
1-(4-(6-isobutoxypyrimidin-4-yl)piperazin-1-yl)-2-(phenylsulfonyl)ethanone;
1-(4-(6-isobutoxypyrimidin-4-yl)piperazin-1-yl)-2-(3-methoxyphenoxyl)ethanone;
(1-(2-hydroxyethyl)-1H-indol-2-yl)(4-(6-isobutoxypyrimidin-4-yl)piperazin-1-yl)methanone;
4-fluoro-N-(2-(4-(6-isobutoxypyrimidin-4-yl)piperazin-1-yl)-2-oxoethyl)benzamide;
N-(2-(4-(6-isobutoxypyrimidin-4-yl)piperazin-1-yl)-2-oxoethyl)-6-methoxypicolinamide;
N-(2-(4-(6-isobutoxypyrimidin-4-yl)piperazin-1-yl)-2-oxoethyl)-6-(2,2,2-trifluoroethoxyl)nicotinamide;
N-(2-(4-(6-isobutoxypyrimidin-4-yl)piperazin-1-yl)-2-oxoethyl)-1H-indole-4-carboxamide;
N-(2-(4-(6-isobutoxypyrimidin-4-yl)piperazin-1-yl)-2-oxoethyl)-1-methyl-1H-indazole-3-carboxamide;
1-(4-(6-isobutoxypyrimidin-4-yl)piperazin-1-yl)-2-(quinolin-8-yloxy)ethanone;
1-(4-(6-isobutoxypyrimidin-4-yl)piperazin-1-yl)-2-(quinolin-5-yloxy)ethanone;
1-(4-(6-isobutoxypyrimidin-4-yl)piperazin-1-yl)-24(6-methylpyridin-3-yl)oxy)ethanone;
(4-(6-cyclobutoxypyrimidin-4-yl)piperazin-1-yl)(2-methyl-2H-indazol-3-yl)methanone;
(4-(6-cyclobutoxypyrimidin-4-yl)piperazin-1-yl)(1H-indazol-3-yl)methanone;
(4-(6-cyclobutoxypyrimidin-4-yl)piperazin-1-yl)(quinoxalin-2-yl)methanone;
(4-(6-cyclobutoxypyrimidin-4-yl)piperazin-1-yl)(8-hydroxyquinolin-2-yl)methanone;
(4-(6-cyclobutoxypyrimidin-4-yl)piperazin-1-yl)(1-methyl-3-(trifluoromethyl)-1H-pyrazol-5-yl)methanone;
N-(2-(4-(6-cyclobutoxypyrimidin-4-yl)piperazin-1-yl)-2-oxoethyl)benzamide;
benzo[b]thiophen-2-yl(4-(6-isobutoxypyrimidin-4-yl)piperazin-1-yl)methanone;
(4-(6-isobutoxypyrimidin-4-yl)piperazin-1-yl)(thieno[2,3-b]pyridin-2-yl)methanone;
(4-(6-isobutoxypyrimidin-4-yl)piperazin-1-yl)(thieno[2,3-b]pyrazin-6-yl)methanone;
3-(4-fluorophenoxy)-1-(4-(6-isobutoxypyrimidin-4-yl)piperazin-1-yl)propan-1-one;
(4-(6-isobutoxypyrimidin-4-yl)piperazin-1-yl)(5-phenylisoxazol-3-yl)methanone;
(4-(6-isobutoxypyrimidin-4-yl)piperazin-1-yl)(5-methyl-1-phenyl-1H-pyrazol-3-yl)methanone;
(4-(6-isobutoxypyrimidin-4-yl)piperazin-1-yl)(4-(oxazol-5-yl)phenyl)methanone;
(4-(1H-pyrazol-1-yl)phenyl)(4-(6-isobutoxypyrimidin-4-yl)piperazin-1-yl)methanone;
(3-fluoro-4-methylphenyl)((1S,4S)-5-(6-isobutoxypyrimidin-4-yl)-2,5-diazabicyclo[2.2.1]heptan-2-yl)methanone;
2-(4-fluorophenoxy)-1-((1S,4S)-5-(6-isobutoxypyrimidin-4-yl)-2,5-diazabicyclo[2.2.1]heptan-2-yl)ethanone;
2-(3-fluorophenoxy)-1-(4-(6-isobutoxypyrimidin-4-yl)piperazin-1-yl)ethanone;
2-(3,4-difluorophenoxy)-1-(4-(6-isobutoxypyrimidin-4-yl)piperazin-1-yl)ethanone;
2-(2-(4-(6-isobutoxypyrimidin-4-yl)piperazin-1-yl)-2-oxoethyl)-3,4-dihydroisoquinolin-1(2H)-one;
1-(2-(4-(6-isobutoxypyrimidin-4-yl)piperazin-1-yl)-2-oxoethyl)-3,4-dihydroquinolin-2(1H)-one;
2-(cyclohexylamino)-1-(4-(6-isobutoxypyrimidin-4-yl)piperazin-1-yl)ethanone;
1-(4-(6-isobutoxypyrimidin-4-yl)piperazin-1-yl)-2-(1-methyl-1H-indol-3-yl)ethanone;
2-(1H-indol-3-yl)-1-(4-(6-isobutoxypyrimidin-4-yl)piperazin-1-yl)ethanone;
3-(2-(4-(6-isobutoxypyrimidin-4-yl)piperazin-1-yl)-2-oxoethyl)benzo[d]oxazol-2(3H)-one;
2-(1H-benzo[d]imidazol-2-yl)-1-(4-(6-isobutoxypyrimidin-4-yl)piperazin-1-yl)ethanone;
2-(2H-benzo[d][1,2,3]triazol-2-yl)-1-(4-(6-isobutoxypyrimidin-4-yl)piperazin-1-yl)ethanone;
2-(benzyloxy)-1-(4-(6-isobutoxypyrimidin-4-yl)piperazin-1-yl)ethanone;
2-(benzo[d]isoxazol-3-yl)-1-(4-(6-(2,2,2-trifluoroethoxyl)pyrimidin-4-yl)piperazin-1-yl)ethanone;
2-(2-oxo-2-(4-(6-(2,2,2-trifluoroethoxyl)pyrimidin-4-yl)piperazin-1-yl)ethyl)isoindolin-1-one;
2-(3-oxo-3-(4-(6-(2,2,2-trifluoroethoxyl)pyrimidin-4-yl)piperazin-1-yl)propyl)isoindolin-1-one;
2-(5-fluoro-1H-indol-3-yl)-1-(4-(6-(2,2,2-trifluoroethoxyl)pyrimidin-4-yl)piperazin-1-yl)ethanone;
2-(benzo[d]isoxazol-3-yl)-1-(4-(6-cyclobutoxypyrimidin-4-yl)piperazin-1-yl)ethanone;
(4-(6-cyclobutoxypyrimidin-4-yl)piperazin-1-yl)(thieno[2,3-b]pyridin-2-yl)methanone;
(4-(6-cyclobutoxypyrimidin-4-yl)piperazin-1-yl)(2,3-dihydrobenzofuran-2-yl)methanone;
(4-(6-cyclobutoxypyrimidin-4-yl)piperazin-1-yl)(4-methoxyquinolin-2-yl)methanone;
(4-(6-cyclobutoxypyrimidin-4-yl)piperazin-1-yl)(isoquinolin-3-yl)methanone;
(5-fluoro-1H-indazol-3-yl)(4-(6-(2,2,2-trifluoroethoxyl)pyrimidin-4-yl)piperazin-1-yl)methanone;
(4-(6-isopropoxypyrimidin-4-yl)piperazin-1-yl)(1-methyl-1H-indazol-3-yl)methanone;
4-fluoro-N-(3-(4-(6-isobutoxypyrimidin-4-yl)piperazin-1-yl)-3-oxopropyl)benzamide;
2-(4-fluorophenyl)-1-(4-(6-isobutoxypyrimidin-4-yl)piperazin-1-yl)ethanone;
1-(4-(6-isobutoxypyrimidin-4-yl)piperazin-1-yl)-2-(phenylthio)ethanone;
2-((4-chlorophenyl)sulfonyl)-1-(4-(6-isobutoxypyrimidin-4-yl)piperazin-1-yl)ethanone;
2-((4-fluorophenyl)sulfonyl)-1-(4-(6-isobutoxypyrimidin-4-yl)piperazin-1-yl)ethanone;
(S)-(1-(3-fluoro-4-methylbenzoyl)pyrrolidin-2-yl)(4-(6-isobutoxypyrimidin-4-yl)piperazin-1-yl)methanone;
(1,3-dimethyl-1H-thieno[2,3-c]pyrazol-5-yl)(4-(6-isobutoxypyrimidin-4-yl)piperazin-1-yl)methanone;
(4-(6-isobutoxypyrimidin-4-yl)piperazin-1-yl)(thiophen-2-yl)methanone;

imidazo[2,1-b]thiazol-6-yl(4-(6-isobutoxypyrimidin-4-yl)piperazin-1-yl)methanone;
1-(4-(6-isobutoxypyrimidin-4-yl)piperazin-1-yl)-2-(quinolin-7-yloxy)ethanone;
1-(4-(6-isobutoxypyrimidin-4-yl)piperazin-1-yl)-2-(isoquinolin-8-yloxy)ethanone;
2-((5-fluoroquinolin-8-yl)oxy)-1-(4-(6-isobutoxypyrimidin-4-yl)piperazin-1-yl)ethanone;
(2-(ethylsulfonyl)phenyl)(4-(6-isobutoxypyrimidin-4-yl)piperazin-1-yl)methanone;
1-(4-(6-isobutoxypyrimidin-4-yl)piperazin-1-yl)-3-phenoxypropan-1-one;
1-(4-(6-isobutoxypyrimidin-4-yl)piperazin-1-yl)-3-(m-tolyloxy)propan-1-one;
(4-(6-isobutoxypyrimidin-4-yl)piperazin-1-yl)(1-methyl-5-phenyl-1H-pyrazol-3-yl)methanone;
(4-(6-isobutoxypyrimidin-4-yl)piperazin-1-yl)(1-methyl-3-phenyl-1H-pyrazol-5-yl)methanone;
(4-(6-isobutoxypyrimidin-4-yl)piperazin-1-yl)(5-methyl-1-phenyl-1H-pyrazol-4-yl)methanone;
(4-(6-isobutoxypyrimidin-4-yl)piperazin-1-yl)(5-methyl-1-phenyl-1H-1,2,3-triazol-4-yl)methanone;
2-((1H-indol-4-yl)oxy)-1-(4-(6-isobutoxypyrimidin-4-yl)piperazin-1-yl)ethanone;
2-(benzylsulfonyl)-1-(4-(6-isobutoxypyrimidin-4-yl)piperazin-1-yl)ethanone;
3-(4-fluorophenoxy)-1-(4-(6-(2,2,2-trifluoroethoxyl)pyrimidin-4-yl)piperazin-1-yl)propan-1-one;
1-(4-(6-cyclobutoxypyrimidin-4-yl)piperazin-1-yl)-3-(4-fluorophenoxyl)propan-1-one;
1-(4-(6-isobutoxypyrimidin-4-yl)piperazin-1-yl)-24(1-methyl-1H-indol-4-yl)oxy)ethanone;
benzo[d]thiazol-2-yl(4-(6-isobutoxypyrimidin-4-yl)piperazin-1-yl)methanone;
1-(4-(6-isobutoxypyrimidin-4-yl)piperazin-1-yl)-2-(2-(trifluoromethyl)phenoxy)ethanone;
2-((5-chloropyridin-3-yl)oxy)-1-(4-(6-isobutoxypyrimidin-4-yl)piperazin-1-yl)ethanone;
1-(4-(6-isobutoxypyrimidin-4-yl)piperazin-1-yl)-2-(3-(trifluoromethoxy)phenoxy)ethanone;
2-(2H-benzo[d][1,2,3]triazol-2-yl)-1-(4-(6-(2,2,2-trifluoroethoxyl)pyrimidin-4-yl)piperazin-1-yl)ethanone;
2-(quinazolin-4-yloxy)-1-(4-(6-(2,2,2-trifluoroethoxyl)pyrimidin-4-yl)piperazin-1-yl)ethanone;
(5-methyl-1-phenyl-1H-pyrazol-4-yl)(4-(6-(2,2,2-trifluoroethoxyl)pyrimidin-4-yl)piperazin-1-yl)methanone;
1-(benzo[d]oxazol-2-ylmethyl)-4-(6-isobutoxypyrimidin-4-yl)piperazin-2-one;
1-(4-fluorobenzyl)-4-(6-(2,2,2-trifluoroethoxyl)pyrimidin-4-yl)piperazin-2-one;
1-(4-(6-isobutoxypyrimidin-4-yl)piperazin-1-yl)-2-methyl-2-(phenylsulfonyl)propan-1-one;
(R)-2-(4-fluorophenoxy)-1-(4-(6-isobutoxypyrimidin-4-yl)piperazin-1-yl)propan-1-one;
(R)-1-(4-(6-cyclobutoxypyrimidin-4-yl)piperazin-1-yl)-2-(4-fluorophenoxyl)propan-1-one;
2-(benzyloxy)-1-(4-(6-cyclobutoxypyrimidin-4-yl)piperazin-1-yl)ethanone;
2-(3-fluorophenoxy)-1-(4-(6-(2,2,2-trifluoroethoxyl)pyrimidin-4-yl)piperazin-1-yl)ethanone;
2-(quinolin-8-yloxy)-1-(4-(6-(2,2,2-trifluoroethoxyl)pyrimidin-4-yl)piperazin-1-yl)ethanone;
2-(2-oxo-2-(4-(6-(2,2,2-trifluoroethoxyl)pyrimidin-4-yl)piperazin-1-yl)ethyl)-3,4-dihydroisoquinolin-1(2H)-one;
1-(2-oxo-2-(4-(6-(2,2,2-trifluoroethoxyl)pyrimidin-4-yl)piperazin-1-yl)ethyl)-3,4-dihydroquinolin-2(1H)-one;
2-(chroman-4-yloxy)-1-(4-(6-isobutoxypyrimidin-4-yl)piperazin-1-yl)ethanone;
1-(4-(6-isobutoxypyrimidin-4-yl)piperazin-1-yl)-2-(quinolin-2-yloxy)ethanone;
2-(chroman-4-yloxy)-1-(4-(6-(2,2,2-trifluoroethoxyl)pyrimidin-4-yl)piperazin-1-yl)ethanone;
2-((1H-indol-4-yl)oxy)-1-(4-(6-(2,2,2-trifluoroethoxyl)pyrimidin-4-yl)piperazin-1-yl)ethanone;
1-(4-(6-isobutoxypyrimidin-4-yl)piperazin-1-yl)-2-phenylethane-1,2-dione;
(4-(6-isopropoxypyrimidin-4-yl)piperazin-1-yl)(1-methyl-3-phenyl-1H-pyrazol-5-yl)methanone;
(4-(6-isopropoxypyrimidin-4-yl)piperazin-1-yl)(2-phenylthiazol-4-yl)methanone;
(2-phenylthiazol-4-yl)(4-(6-(2,2,2-trifluoroethoxyl)pyrimidin-4-yl)piperazin-1-yl)methanone;
(2-benzylthiazol-4-yl)(4-(6-isobutoxypyrimidin-4-yl)piperazin-1-yl)methanone;
2-((4-fluorobenzyl)oxy)-1-(4-(6-isobutoxypyrimidin-4-yl)piperazin-1-yl)ethanone;
(1-(4-fluorophenyl)-5-methyl-1H-pyrazol-4-yl)(4-(6-isobutoxypyrimidin-4-yl)piperazin-1-yl)methanone;
(4-(6-isobutoxypyrimidin-4-yl)piperazin-1-yl)(1-(4-methoxyphenyl)-5-methyl-1H-pyrazol-4-yl)methanone;
(1-benzyl-1H-pyrazol-4-yl)(4-(6-isobutoxypyrimidin-4-yl)piperazin-1-yl)methanone;
(4-(6-isobutoxypyrimidin-4-yl)piperazin-1-yl)(5-methyl-3-phenylisoxazol-4-yl)methanone;
(4-(6-isobutoxypyrimidin-4-yl)piperazin-1-yl)(3-methyl-5-phenylisoxazol-4-yl)methanone;
(5-(2-fluorophenyl)oxazol-4-yl)(4-(6-isobutoxypyrimidin-4-yl)piperazin-1-yl)methanone;
(4-(6-isobutoxypyrimidin-4-yl)piperazin-1-yl)(3-(2-methoxyphenyl)-1H-pyrazol-5-yl)methanone;
24(3-fluorophenyl)sulfonyl)-1-(4-(6-isobutoxypyrimidin-4-yl)piperazin-1-yl)ethanone;
1-(4-(6-isobutoxypyrimidin-4-yl)piperazin-1-yl)-24(3-methoxyphenyl)sulfonyl)ethanone;
1-(4-(6-cyclobutoxypyrimidin-4-yl)piperazin-1-yl)-2-((3-fluorophenyl)sulfonyl)ethanone;
1-(4-(6-cyclobutoxypyrimidin-4-yl)piperazin-1-yl)-2-((3-methoxyphenyl)sulfonyl)ethanone;
(2-((2-hydroxyethyl)thio)phenyl)(4-(6-isobutoxypyrimidin-4-yl)piperazin-1-yl)methanone;
(5-methyl-1-phenyl-1H-1,2,3-triazol-4-yl)(4-(6-(2,2,2-trifluoroethoxyl)pyrimidin-4-yl)piperazin-1-yl)methanone;
(4-(6-isobutoxypyrimidin-4-yl)piperazin-1-yl)(5-methyl-2-phenyl-2H-1,2,3-triazol-4-yl)methanone;
(4-(6-isobutoxypyrimidin-4-yl)piperazin-1-yl)(1-(2-methoxyphenyl)-1H-pyrazol-4-yl)methanone;
(5-amino-1-phenyl-1H-pyrazol-4-yl)(4-(6-isobutoxypyrimidin-4-yl)piperazin-1-yl)methanone;
(4-(6-isobutoxypyrimidin-4-yl)piperazin-1-yl)(6-phenylpyrimidin-4-yl)methanone;
(3-(1H-pyrazol-1-yl)phenyl)(4-(6-isobutoxypyrimidin-4-yl)piperazin-1-yl)methanone;
(4-(6-isobutoxypyrimidin-4-yl)piperazin-1-yl)(3-(2-methylthiazol-4-yl)phenyl)methanone;
(4-(6-isobutoxypyrimidin-4-yl)piperazin-1-yl)(3-(pyridin-3-yl)-1H-pyrazol-5-yl)methanone;
(4-(6-isobutoxypyrimidin-4-yl)piperazin-1-yl)(1-methyl-3-(pyridin-3-yl)-1H-pyrazol-5-yl)methanone;
(4-(6-isobutoxypyrimidin-4-yl)piperazin-1-yl)(2-(pyridin-3-yl)thiazol-4-yl)methanone;

(4-(6-isobutoxypyrimidin-4-yl)piperazin-1-yl)(2-(pyridin-2-yl)thiazol-4-yl)methanone;
(4-(6-isopropoxypyrimidin-4-yl)piperazin-1-yl)(2-(pyridin-3-yl)thiazol-4-yl)methanone;
(4-(6-isopropoxypyrimidin-4-yl)piperazin-1-yl)(2-(pyridin-2-yl)thiazol-4-yl)methanone;
(4-(6-isobutoxypyrimidin-4-yl)piperazin-1-yl)(1-methyl-1H-pyrazolo[3,4-b]pyridin-3-yl)methanone;
(1-methyl-1H-pyrazolo[3,4-b]pyridin-3-yl)(4-(6-(2,2,2-trifluoroethoxyl)pyrimidin-4-yl)piperazin-1-yl)methanone;
benzo[d][1,2,3]thiadiazol-7-yl(4-(6-isobutoxypyrimidin-4-yl)piperazin-1-yl)methanone;
1-(4-(6-cyclobutoxypyrimidin-4-yl)piperazin-1-yl)-24(1-methyl-1H-indol-4-yl)oxy)ethanone;
1-(4-(6-isopropoxypyrimidin-4-yl)piperazin-1-yl)-24(1-methyl-1H-indol-4-yl)oxy)ethanone;
(5-fluoro-1H-indazol-3-yl)(4-(6-isobutoxypyrimidin-4-yl)piperazin-1-yl)methanone;
(5-fluoro-1H-indazol-3-yl)(4-(6-isopropoxypyrimidin-4-yl)piperazin-1-yl)methanone;
(4-(6-cyclobutoxypyrimidin-4-yl)piperazin-1-yl)(5-fluoro-1H-indazol-3-yl)methanone;
(1-(4-fluorophenyl)-5-methyl-1H-1,2,3-triazol-4-yl)(4-(6-isobutoxypyrimidin-4-yl)piperazin-1-yl)methanone;
(1-(4-fluorophenyl)-5-methyl-1H-1,2,3-triazol-4-yl)(4-(6-isopropoxypyrimidin-4-yl)piperazin-1-yl)methanone;
(4-(6-cyclobutoxypyrimidin-4-yl)piperazin-1-yl)(1-(4-fluorophenyl)-5-methyl-1H-1,2,3-triazol-4-yl)methanone;
(1-(4-fluorophenyl)-5-methyl-1H-1,2,3-triazol-4-yl)(4-(6-(2,2,2-trifluoroethoxyl)pyrimidin-4-yl)piperazin-1-yl)methanone;
(4-(6-isobutoxypyrimidin-4-yl)piperazin-1-yl)(1-phenyl-1H-1,2,3-triazol-4-yl)methanone;
(4-(6-isobutoxypyrimidin-4-yl)piperazin-1-yl)(3-(pyridin-2-yl)-1H-pyrazol-5-yl)methanone;
(4-(6-isobutoxypyrimidin-4-yl)piperazin-1-yl)(4-methyl-2-phenyloxazol-5-yl)methanone;
(5-fluoro-1-methyl-1H-indazol-3-yl)(4-(6-isobutoxypyrimidin-4-yl)piperazin-1-yl)methanone;
(5-fluoro-1-methyl-1H-indazol-3-yl)(4-(6-isopropoxypyrimidin-4-yl)piperazin-1-yl)methanone;
(4-(6-cyclobutoxypyrimidin-4-yl)piperazin-1-yl)(5-fluoro-1-methyl-1H-indazol-3-yl)methanone;
(5-fluoro-1-methyl-1H-indazol-3-yl)(4-(6-(2,2,2-trifluoroethoxyl)pyrimidin-4-yl)piperazin-1-yl)methanone;
(4-(6-isobutoxypyrimidin-4-yl)piperazin-1-yl)(2-phenylthiazol-4-yl)methanone;
(6-(1H-pyrazol-1-yl)pyridin-3-yl)(4-(6-isobutoxypyrimidin-4-yl)piperazin-1-yl)methanone;
(4-(6-isobutoxypyrimidin-4-yl)piperazin-1-yl)(1-phenyl-1H-pyrazol-4-yl)methanone;
(1-phenyl-1H-pyrazol-4-yl)(4-(6-(2,2,2-trifluoroethoxyl)pyrimidin-4-yl)piperazin-1-yl)methanone;
(1-ethyl-3-(trifluoromethyl)-1H-pyrazol-5-yl)(4-(6-isobutoxypyrimidin-4-yl)piperazin-1-yl)methanone;
(1-ethyl-3-(trifluoromethyl)-1H-pyrazol-5-yl)(4-(6-(2,2,2-trifluoroethoxyl)pyrimidin-4-yl)piperazin-1-yl)methanone;
(4-(6-cyclobutoxypyrimidin-4-yl)piperazin-1-yl)(5-methyl-1-phenyl-1H-1,2,3-triazol-4-yl)methanone;
2-(2H-benzo[d][1,2,3]triazol-2-yl)-1-(4-(6-cyclobutoxypyrimidin-4-yl)piperazin-1-yl)ethanone;
benzo[c]isoxazol-3-yl(4-(6-isobutoxypyrimidin-4-yl)piperazin-1-yl)methanone;
(4-(6-isobutoxypyrimidin-4-yl)piperazin-1-yl)(4,5,6,7-tetrahydro-1H-indazol-3-yl)methanone;
(4-(6-isobutoxypyrimidin-4-yl)piperazin-1-yl)(2-methyl-4,5,6,7-tetrahydro-2H-indazol-3-yl)methanone;
2-(2-(4-(6-cyclobutoxypyrimidin-4-yl)piperazin-1-yl)-2-oxoethyl)-3,4-dihydroisoquinolin-1(2H)-one;
(4-(6-cyclobutoxypyrimidin-4-yl)piperazin-1-yl)(1-methyl-1H-benzo[d]imidazol-2-yl)methanone;
(4-(6-isobutoxypyrimidin-4-yl)piperazin-1-yl)(5-(6-methoxypyridin-3-yl)-1-methyl-1H-pyrazol-3-yl)methanone;
(4-(6-cyclobutoxypyrimidin-4-yl)piperazin-1-yl)(pyrazolo[1,5-a]pyridin-2-yl)methanone;
(1-ethyl-5-(trifluoromethyl)-1H-pyrazol-3-yl)(4-(6-isobutoxypyrimidin-4-yl)piperazin-1-yl)methanone;
(1-ethyl-5-(trifluoromethyl)-1H-pyrazol-3-yl)(4-(6-(2,2,2-trifluoroethoxyl)pyrimidin-4-yl)piperazin-1-yl)methanone;
(4-(6-isobutoxypyrimidin-4-yl)piperazin-1-yl)(1-(pyridin-2-yl)-1H-pyrazol-4-yl)methanone;
(6-ethoxypyridin-2-yl)(4-(6-isobutoxypyrimidin-4-yl)piperazin-1-yl)methanone;
(4-(6-isobutoxypyrimidin-4-yl)piperazin-1-yl)(6-(2,2,2-trifluoroethoxyl)pyridin-2-yl)methanone;
(4-(6-isobutoxypyrimidin-4-yl)piperazin-1-yl)(2-isopropylthiazol-4-yl)methanone;
(3-cyclopropyl-1-methyl-1H-pyrazol-5-yl)(4-(6-isobutoxypyrimidin-4-yl)piperazin-1-yl)methanone;
(5-cyclopropyl-1-methyl-1H-pyrazol-3-yl)(4-(6-isobutoxypyrimidin-4-yl)piperazin-1-yl)methanone;
2-(2-(4-(6-isobutoxypyrimidin-4-yl)piperazin-1-yl)-2-oxoethyl)isoquinolin-1 (2H)-one;
2-(2-oxo-2-(4-(6-(2,2,2-trifluoroethoxyl)pyrimidin-4-yl)piperazin-1-yl)ethyl)isoquinolin-1 (2H)-one;
(4-(6-isobutoxypyrimidin-4-yl)piperazin-1-yl)(2-(trifluoromethyl)thiazol-4-yl)methanone;
(4-(6-(2,2,2-trifluoroethoxyl)pyrimidin-4-yl)piperazin-1-yl)(2-(trifluoromethyl)thiazol-4-yl)methanone;
2-(2H-indazol-2-yl)-1-(4-(6-isobutoxypyrimidin-4-yl)piperazin-1-yl)ethanone;
(4-(6-ethoxypyrimidin-4-yl)piperazin-1-yl)(2-(pyridin-2-yl)thiazol-4-yl)methanone;
(5-(2-fluorophenyl)oxazol-4-yl)(4-(6-(2,2,2-trifluoroethoxyl)pyrimidin-4-yl)piperazin-1-yl)methanone;
(4-(6-(2,2,2-trifluoroethoxyl)pyrimidin-4-yl)piperazin-1-yl)(1-(2-(trifluoromethyl)phenyl)-1H-imidazol-5-yl)methanone;
(2-(pyridin-2-yl)thiazol-4-yl)(4-(6-(2,2,2-trifluoroethoxyl)pyrimidin-4-yl)piperazin-1-yl)methanone;
(5-methyl-3-phenylisoxazol-4-yl)(4-(6-(2,2,2-trifluoroethoxyl)pyrimidin-4-yl)piperazin-1-yl)methanone; and
(2-(1H-pyrazol-3-yl)phenyl)(4-(6-(2,2,2-trifluoroethoxyl)pyrimidin-4-yl)piperazin-1-yl)methanone;
or a pharmaceutically acceptable salt thereof.

5. The compound as claimed in claim 1, which is selected from:
(R)-2-hydroxy-1-(4-(6-isobutoxypyrimidin-4-yl)piperazin-1-yl)-3-phenylpropan-1-one;
(4-(6-(cyclopentyloxy)pyrimidin-4-yl)piperazin-1-yl)(3-fluoro-4-methylphenyl)methanone;
(3-fluoro-4-methylphenyl)(4-(6-(2,2,2-trifluoroethoxyl)pyrimidin-4-yl)piperazin-1-yl)methanone;
(1H-indol-4-yl)(4-(6-isobutoxypyrimidin-4-yl)piperazin-1-yl)methanone;
(S)-tert-butyl (2-(4-(6-isobutoxypyrimidin-4-yl)piperazin-1-yl)-2-oxo-1-phenylethyl)carbamate;

(R)-tert-butyl (2-(4-(6-isobutoxypyrimidin-4-yl)piperazin-1-yl)-2-oxo-1-phenylethyl)carbamate;
(4-(6-isobutoxypyrimidin-4-yl)piperazin-1-yl)(1-methyl-3-(trifluoromethyl)-1H-pyrazol-5-yl)methanone;
(4-(6-isobutoxypyrimidin-4-yl)piperazin-1-yl)(3-(trifluoromethoxy)phenyl)methanone;
(4-(6-cyclobutoxypyrimidin-4-yl)piperazin-1-yl)(3-fluoro-4-methylphenyl)methanone;
(4-(6-isobutoxypyrimidin-4-yl)piperazin-1-yl)(quinolin-2-yl)methanone;
(4-(6-isobutoxypyrimidin-4-yl)piperazin-1-yl)(1-methyl-1H-indazol-3-yl)methanone;
(4-(6-isobutoxypyrimidin-4-yl)piperazin-1-yl)(1-methyl-1H-benzo[d]imidazol-2-yl)methanone;
2-(4-fluorophenoxy)-1-(4-(6-isobutoxypyrimidin-4-yl)piperazin-1-yl)ethanone;
(S)-2-amino-1-(4-(6-isobutoxypyrimidin-4-yl)piperazin-1-yl)-2-phenylethanone;
(R)-2-amino-1-(4-(6-isobutoxypyrimidin-4-yl)piperazin-1-yl)-2-phenylethanone;
(1-methyl-5-(trifluoromethyl)-1H-pyrazol-3-yl)(4-(6-(2,2,2-trifluoroethoxy)pyrimidin-4-yl)piperazin-1-yl)methanone;
(1-methyl-1H-indazol-3-yl)(4-(6-(2,2,2-trifluoroethoxy)pyrimidin-4-yl)piperazin-1-yl)methanone;
(8-hydroxyquinolin-2-yl)(4-(6-isobutoxypyrimidin-4-yl)piperazin-1-yl)methanone;
(4-(6-isobutoxypyrimidin-4-yl)piperazin-1-yl)(quinoxalin-2-yl)methanone;
(4-(6-cyclobutoxypyrimidin-4-yl)piperazin-1-yl)(1-methyl-1H-indazol-3-yl)methanone;
(4-chloro-3-fluorophenyl)(4-(6-isobutoxypyrimidin-4-yl)piperazin-1-yl)methanone;
(2-hydroxy-4-(trifluoromethyl)phenyl)(4-(6-isobutoxypyrimidin-4-yl)piperazin-1-yl)methanone;
(4-(6-isobutoxypyrimidin-4-yl)piperazin-1-yl)(1-methyl-1H-indol-2-yl)methanone;
2-(4-fluorophenoxy)-1-(4-(6-isobutoxypyrimidin-4-yl)piperazin-1-yl)propan-1-one;
(4-(6-isobutoxypyrimidin-4-yl)piperazin-1-yl)(6-(pyrrolidin-1-yl)pyridin-2-yl)methanone;
benzyl 4-(6-isobutoxypyrimidin-4-yl)piperazine-1-carboxylate;
4-(2-(4-(6-isobutoxypyrimidin-4-yl)piperazin-1-yl)-2-oxoethyl)-2H-benzo[b][1,4]oxazin-3(4H)-one;
2-(benzo[d]isoxazol-3-yl)-1-(4-(6-isobutoxypyrimidin-4-yl)piperazin-1-yl)ethanone;
3-(1H-indol-1-yl)-1-(4-(6-isobutoxypyrimidin-4-yl)piperazin-1-yl)propan-1-one;
2-(5-fluoro-1H-indol-3-yl)-1-(4-(6-isobutoxypyrimidin-4-yl)piperazin-1-yl)ethanone;
2-(3-(4-(6-isobutoxypyrimidin-4-yl)piperazin-1-yl)-3-oxopropyl)isoindolin-1-one;
(4-(6-isobutoxypyrimidin-4-yl)piperazin-1-yl)(1-(2-methoxyethyl)-1H-indol-2-yl)methanone;
(4-methoxyquinolin-2-yl)(4-(6-(2,2,2-trifluoroethoxy)pyrimidin-4-yl)piperazin-1-yl)methanone;
(8-hydroxyquinolin-2-yl)(4-(6-(2,2,2-trifluoroethoxy)pyrimidin-4-yl)piperazin-1-yl)methanone;
(1H-indazol-3-yl)(4-(6-(2,2,2-trifluoroethoxy)pyrimidin-4-yl)piperazin-1-yl)methanone;
1-(4-(6-isobutoxypyrimidin-4-yl)piperazin-1-yl)-2-(3-methoxyphenoxy)ethanone;
N-(2-(4-(6-isobutoxypyrimidin-4-yl)piperazin-1-yl)-2-oxoethyl)-6-methoxypicolinamide;
N-(2-(4-(6-isobutoxypyrimidin-4-yl)piperazin-1-yl)-2-oxoethyl)-6-(2,2,2-trifluoroethoxy)nicotinamide;
N-(2-(4-(6-isobutoxypyrimidin-4-yl)piperazin-1-yl)-2-oxoethyl)-1H-indole-4-carboxamide;
N-(2-(4-(6-isobutoxypyrimidin-4-yl)piperazin-1-yl)-2-oxoethyl)-1-methyl-1H-indazole-3-carboxamide;
1-(4-(6-isobutoxypyrimidin-4-yl)piperazin-1-yl)-2-(quinolin-8-yloxy)ethanone;
1-(4-(6-isobutoxypyrimidin-4-yl)piperazin-1-yl)-2-(quinolin-5-yloxy)ethanone;
(4-(6-cyclobutoxypyrimidin-4-yl)piperazin-1-yl)(quinoxalin-2-yl)methanone;
(4-(6-cyclobutoxypyrimidin-4-yl)piperazin-1-yl)(8-hydroxyquinolin-2-yl)methanone;
N-(2-(4-(6-cyclobutoxypyrimidin-4-yl)piperazin-1-yl)-2-oxoethyl)benzamide;
benzo[b]thiophen-2-yl(4-(6-isobutoxypyrimidin-4-yl)piperazin-1-yl)methanone;
3-(4-fluorophenoxy)-1-(4-(6-isobutoxypyrimidin-4-yl)piperazin-1-yl)propan-1-one;
(4-(6-isobutoxypyrimidin-4-yl)piperazin-1-yl)(5-phenylisoxazol-3-yl)methanone;
(4-(6-isobutoxypyrimidin-4-yl)piperazin-1-yl)(5-methyl-1-phenyl-1H-pyrazol-3-yl)methanone;
(4-(6-isobutoxypyrimidin-4-yl)piperazin-1-yl)(4-(oxazol-5-yl)phenyl)methanone;
(4-(1H-pyrazol-1-yl)phenyl)(4-(6-isobutoxypyrimidin-4-yl)piperazin-1-yl)methanone;
(3-fluoro-4-methylphenyl)((1S,4S)-5-(6-isobutoxypyrimidin-4-yl)-2,5-diazabicyclo[2.2.1]heptan-2-yl)methanone;
2-(3-fluorophenoxy)-1-(4-(6-isobutoxypyrimidin-4-yl)piperazin-1-yl)ethanone;
2-(3,4-difluorophenoxy)-1-(4-(6-isobutoxypyrimidin-4-yl)piperazin-1-yl)ethanone;
2-(2-(4-(6-isobutoxypyrimidin-4-yl)piperazin-1-yl)-2-oxoethyl)-3,4-dihydroisoquinolin-1(2H)-one;
2-(cyclohexylamino)-1-(4-(6-isobutoxypyrimidin-4-yl)piperazin-1-yl)ethanone;
1-(4-(6-isobutoxypyrimidin-4-yl)piperazin-1-yl)-2-(1-methyl-1H-indol-3-yl)ethanone;
2-(1H-indol-3-yl)-1-(4-(6-isobutoxypyrimidin-4-yl)piperazin-1-yl)ethanone;
2-(2H-benzo[d][1,2,3]triazol-2-yl)-1-(4-(6-isobutoxypyrimidin-4-yl)piperazin-1-yl)ethanone;
2-(benzyloxy)-1-(4-(6-isobutoxypyrimidin-4-yl)piperazin-1-yl)ethanone;
2-(benzo[d]isoxazol-3-yl)-1-(4-(6-(2,2,2-trifluoroethoxy)pyrimidin-4-yl)piperazin-1-yl)ethanone;
2-(5-fluoro-1H-indol-3-yl)-1-(4-(6-(2,2,2-trifluoroethoxy)pyrimidin-4-yl)piperazin-1-yl)ethanone;
2-(benzo[d]isoxazol-3-yl)-1-(4-(6-cyclobutoxypyrimidin-4-yl)piperazin-1-yl)ethanone;
2-(4-fluorophenyl)-1-(4-(6-isobutoxypyrimidin-4-yl)piperazin-1-yl)ethanone;
1-(4-(6-isobutoxypyrimidin-4-yl)piperazin-1-yl)-2-(phenylthio)ethanone;
2-((4-chlorophenyl)sulfonyl)-1-(4-(6-isobutoxypyrimidin-4-yl)piperazin-1-yl)ethanone;
1-(4-(6-isobutoxypyrimidin-4-yl)piperazin-1-yl)-2-(quinolin-7-yloxy)ethanone;
1-(4-(6-isobutoxypyrimidin-4-yl)piperazin-1-yl)-2-(isoquinolin-8-yloxy)ethanone;
2-((5-fluoroquinolin-8-yl)oxy)-1-(4-(6-isobutoxypyrimidin-4-yl)piperazin-1-yl)ethanone;
1-(4-(6-isobutoxypyrimidin-4-yl)piperazin-1-yl)-3-phenoxypropan-1-one;
1-(4-(6-isobutoxypyrimidin-4-yl)piperazin-1-yl)-3-(m-tolyloxy)propan-1-one;

(4-(6-isobutoxypyrimidin-4-yl)piperazin-1-yl)(1-methyl-5-phenyl-1H-pyrazol-3-yl)methanone;
(4-(6-isobutoxypyrimidin-4-yl)piperazin-1-yl)(1-methyl-3-phenyl-1H-pyrazol-5-yl)methanone;
(4-(6-isobutoxypyrimidin-4-yl)piperazin-1-yl)(5-methyl-1-phenyl-1H-pyrazol-4-yl)methanone;
(4-(6-isobutoxypyrimidin-4-yl)piperazin-1-yl)(5-methyl-1-phenyl-1H-1,2,3-triazol-4-yl)methanone;
2-((1H-indol-4-yl)oxy)-1-(4-(6-isobutoxypyrimidin-4-yl)piperazin-1-yl)ethanone;
3-(4-fluorophenoxy)-1-(4-(6-(2,2,2-trifluoroethoxyl)pyrimidin-4-yl)piperazin-1-yl)propan-1-one;
1-(4-(6-cyclobutoxypyrimidin-4-yl)piperazin-1-yl)-3-(4-fluorophenoxyl)propan-1-one;
1-(4-(6-isobutoxypyrimidin-4-yl)piperazin-1-yl)-24(1-methyl-1H-indol-4-yl)oxy)ethanone;
1-(4-(6-isobutoxypyrimidin-4-yl)piperazin-1-yl)-2-(2-(trifluoromethyl)phenoxy)ethanone;
2-((5-chloropyridin-3-yl)oxy)-1-(4-(6-isobutoxypyrimidin-4-yl)piperazin-1-yl)ethanone;
1-(4-(6-isobutoxypyrimidin-4-yl)piperazin-1-yl)-2-(3-(trifluoromethoxy)phenoxy)ethanone;
2-(2H-benzo[d][1,2,3]triazol-2-yl)-1-(4-(6-(2,2,2-trifluoroethoxyl)pyrimidin-4-yl)piperazin-1-yl)ethanone;
(5-methyl-1-phenyl-1H-pyrazol-4-yl)(4-(6-(2,2,2-trifluoroethoxyl)pyrimidin-4-yl)piperazin-1-yl)methanone;
(R)-2-(4-fluorophenoxy)-1-(4-(6-isobutoxypyrimidin-4-yl)piperazin-1-yl)propan-1-one;
2-(quinolin-8-yloxy)-1-(4-(6-(2,2,2-trifluoroethoxyl)pyrimidin-4-yl)piperazin-1-yl)ethanone;
2-(2-oxo-2-(4-(6-(2,2,2-trifluoroethoxyl)pyrimidin-4-yl)piperazin-1-yl)ethyl)-3,4-dihydroisoquinolin-1(2H)-one;
1-(4-(6-isobutoxypyrimidin-4-yl)piperazin-1-yl)-2-(quinolin-2-yloxy)ethanone;
2-(chroman-4-yloxy)-1-(4-(6-(2,2,2-trifluoroethoxyl)pyrimidin-4-yl)piperazin-1-yl)ethanone;
(4-(6-isopropoxypyrimidin-4-yl)piperazin-1-yl)(1-methyl-3-phenyl-1H-pyrazol-5-yl)methanone;
(4-(6-isopropoxypyrimidin-4-yl)piperazin-1-yl)(2-phenylthiazol-4-yl)methanone;
(2-phenylthiazol-4-yl)(4-(6-(2,2,2-trifluoroethoxyl)pyrimidin-4-yl)piperazin-1-yl)methanone;
(2-benzylthiazol-4-yl)(4-(6-isobutoxypyrimidin-4-yl)piperazin-1-yl)methanone;
2-((4-fluorobenzyl)oxy)-1-(4-(6-isobutoxypyrimidin-4-yl)piperazin-1-yl)ethanone;
(1-(4-fluorophenyl)-5-methyl-1H-pyrazol-4-yl)(4-(6-isobutoxypyrimidin-4-yl)piperazin-1-yl)methanone;
(1-benzyl-1H-pyrazol-4-yl)(4-(6-isobutoxypyrimidin-4-yl)piperazin-1-yl)methanone;
(4-(6-isobutoxypyrimidin-4-yl)piperazin-1-yl)(3-(2-methoxyphenyl)-1H-pyrazol-5-yl)methanone;
(4-(6-isobutoxypyrimidin-4-yl)piperazin-1-yl)(5-methyl-2-phenyl-2H-1,2,3-triazol-4-yl)methanone;
(4-(6-isobutoxypyrimidin-4-yl)piperazin-1-yl)(1-(2-methoxyphenyl)-1H-pyrazol-4-yl)methanone;
(5-amino-1-phenyl-1H-pyrazol-4-yl)(4-(6-isobutoxypyrimidin-4-yl)piperazin-1-yl)methanone;
(4-(6-isobutoxypyrimidin-4-yl)piperazin-1-yl)(6-phenylpyrimidin-4-yl)methanone;
(4-(6-isobutoxypyrimidin-4-yl)piperazin-1-yl)(3-(2-methylthiazol-4-yl)phenyl)methanone;
(4-(6-isobutoxypyrimidin-4-yl)piperazin-1-yl)(1-methyl-3-(pyridin-3-yl)-1H-pyrazol-5-yl)methanone;
(4-(6-isobutoxypyrimidin-4-yl)piperazin-1-yl)(2-(pyridin-3-yl)thiazol-4-yl)methanone;
(4-(6-isobutoxypyrimidin-4-yl)piperazin-1-yl)(2-(pyridin-2-yl)thiazol-4-yl)methanone;
(4-(6-isopropoxypyrimidin-4-yl)piperazin-1-yl)(2-(pyridin-2-yl)thiazol-4-yl)methanone;
(1-(4-fluorophenyl)-5-methyl-1H-1,2,3-triazol-4-yl)(4-(6-isobutoxypyrimidin-4-yl)piperazin-1-yl)methanone;
(1-(4-fluorophenyl)-5-methyl-1H-1,2,3-triazol-4-yl)(4-(6-isopropoxypyrimidin-4-yl)piperazin-1-yl)methanone;
(4-(6-cyclobutoxypyrimidin-4-yl)piperazin-1-yl)(1-(4-fluorophenyl)-5-methyl-1H-1,2,3-triazol-4-yl)methanone;
(1-(4-fluorophenyl)-5-methyl-1H-1,2,3-triazol-4-yl)(4-(6-(2,2,2-trifluoroethoxyl)pyrimidin-4-yl)piperazin-1-yl)methanone;
(4-(6-isobutoxypyrimidin-4-yl)piperazin-1-yl)(1-phenyl-1H-1,2,3-triazol-4-yl)methanone;
(4-(6-isobutoxypyrimidin-4-yl)piperazin-1-yl)(4-methyl-2-phenyloxazol-5-yl)methanone;
(5-fluoro-1-methyl-1H-indazol-3-yl)(4-(6-isobutoxypyrimidin-4-yl)piperazin-1-yl)methanone;
(5-fluoro-1-methyl-1H-indazol-3-yl)(4-(6-isopropoxypyrimidin-4-yl)piperazin-1-yl)methanone;
(5-fluoro-1-methyl-1H-indazol-3-yl)(4-(6-(2,2,2-trifluoroethoxyl)pyrimidin-4-yl)piperazin-1-yl)methanone;
(4-(6-isobutoxypyrimidin-4-yl)piperazin-1-yl)(2-phenylthiazol-4-yl)methanone;
(6-(1H-pyrazol-1-yl)pyridin-3-yl)(4-(6-isobutoxypyrimidin-4-yl)piperazin-1-yl)methanone;
(4-(6-isobutoxypyrimidin-4-yl)piperazin-1-yl)(1-phenyl-1H-pyrazol-4-yl)methanone;
(1-ethyl-3-(trifluoromethyl)-1H-pyrazol-5-yl)(4-(6-isobutoxypyrimidin-4-yl)piperazin-1-yl)methanone;
(4-(6-cyclobutoxypyrimidin-4-yl)piperazin-1-yl)(5-methyl-1-phenyl-1H-1,2,3-triazol-4-yl)methanone;
2-(2H-benzo[d][1,2,3]triazol-2-yl)-1-(4-(6-cyclobutoxypyrimidin-4-yl)piperazin-1-yl)ethanone;
(1-ethyl-5-(trifluoromethyl)-1H-pyrazol-3-yl)(4-(6-isobutoxypyrimidin-4-yl)piperazin-1-yl)methanone;
(1-ethyl-5-(trifluoromethyl)-1H-pyrazol-3-yl)(4-(6-(2,2,2-trifluoroethoxyl)pyrimidin-4-yl)piperazin-1-yl)methanone;
(6-ethoxypyridin-2-yl)(4-(6-isobutoxypyrimidin-4-yl)piperazin-1-yl)methanone;
(4-(6-isobutoxypyrimidin-4-yl)piperazin-1-yl)(6-(2,2,2-trifluoroethoxyl)pyridin-2-yl)methanone;
(4-(6-isobutoxypyrimidin-4-yl)piperazin-1-yl)(2-isopropylthiazol-4-yl)methanone;
(4-(6-ethoxypyrimidin-4-yl)piperazin-1-yl)(2-(pyridin-2-yl)thiazol-4-yl)methanone;
(4-(6-(2,2,2-trifluoroethoxyl)pyrimidin-4-yl)piperazin-1-yl)(1-(2-(trifluoromethyl)phenyl)-1H-imidazol-5-yl)methanone;
(2-(pyridin-2-yl)thiazol-4-yl)(4-(6-(2,2,2-trifluoroethoxyl)pyrimidin-4-yl)piperazin-1-yl)methanone; and
(5-methyl-3-phenylisoxazol-4-yl)(4-(6-(2,2,2-trifluoroethoxyl)pyrimidin-4-yl)piperazin-1-yl)methanone;
or a pharmaceutically acceptable salt thereof.

6. A pharmaceutical composition comprising a compound or a pharmaceutically acceptable salt thereof, as claimed in claim 1, and a pharmaceutically acceptable carrier.

7. The pharmaceutical composition as claimed in claim 6, further comprising another pharmacologically active agent.

8. A method for the treatment of neuropathic pain, chronic pain, acute pain, cluster and tension headaches, and migraine in an animal, including a human, which comprises administering to an animal in need of such treatment a therapeutically effective amount of a compound or a pharmaceutically acceptable salt thereof, as claimed in claim 1.

* * * * *